US012799177B2

(12) United States Patent
Lim et al.

(10) Patent No.: US 12,799,177 B2
(45) Date of Patent: Nov. 17, 2026

(54) LONG-ACTING GDF15 FUSION PROTEIN AND PHARMACEUTICAL COMPOSITION COMPRISING SAME

(71) Applicant: YUHAN CORPORATION, Seoul (KR)

(72) Inventors: Seyoung Lim, Seoul (KR); Young Bong Park, Seoul (KR); Sukyung Kim, Seoul (KR); Bo Ra Sim, Seoul (KR); Wonee Chong, Seoul (KR); Hyun Ho Choi, Seoul (KR); Ji Eun Yang, Seoul (KR); Mi Kyeong Ju, Seoul (KR); Won Tae Kim, Seoul (KR); Youn Woo Lee, Seoul (KR); Junhwan Kim, Seoul (KR)

(73) Assignee: YUHAN CORPORATION, Seoul (KR)

( * ) Notice: Subject to any disclaimer, the term of this patent is extended or adjusted under 35 U.S.C. 154(b) by 1155 days.

(21) Appl. No.: 17/779,932

(22) PCT Filed: Nov. 25, 2020

(86) PCT No.: PCT/KR2020/016842
§ 371 (c)(1),
(2) Date: May 25, 2022

(87) PCT Pub. No.: WO2021/107603
PCT Pub. Date: Jun. 3, 2021

(65) Prior Publication Data

US 2023/0002460 A1 Jan. 5, 2023

(30) Foreign Application Priority Data

Nov. 26, 2019 (KR) ........................ 10-2019-0153680

(51) Int. Cl.
*C07K 14/475* (2006.01)
*C12N 15/63* (2006.01)

(52) U.S. Cl.
CPC ............ *C07K 14/475* (2013.01); *C12N 15/63* (2013.01); *C07K 2319/30* (2013.01)

(58) Field of Classification Search
None
See application file for complete search history.

(56) References Cited

U.S. PATENT DOCUMENTS 5,288,931 A * 2/1994 Chang .................. C07K 1/1133 530/825
7,112,660 B1 * 9/2006 Domingues ............. A61P 37/08 424/85.2
8,192,735 B2 6/2012 Breit et al.
2003/0045474 A1 * 3/2003 Sailer ...................... A61P 19/08 514/8.8
2008/0161543 A1 * 7/2008 Steward .................. A61P 17/00 424/234.1
2014/0065648 A1 * 3/2014 Wienhues-Thelen ........................ G01N 33/6893 422/69
2014/0154743 A1 * 6/2014 Levy ...................... C07K 16/00 435/69.6
2014/0213511 A1 7/2014 Matern et al.
2014/0378665 A1 12/2014 Xiong et al.
2016/0031960 A1 * 2/2016 Lindhout ............. C07K 14/495 514/6.9
2016/0120999 A1 5/2016 Shen et al.
2018/0079790 A1 3/2018 Xiong et al.
2019/0315822 A1 10/2019 Xiong et al.

FOREIGN PATENT DOCUMENTS

EA 201690297 A1 6/2016
EP 3 144 320 A1 3/2017
KR 10-1727506 B1 5/2017
RU 2 704 285 C2 10/2019
WO 2014/120619 A2 8/2014
WO 2015/017710 A1 2/2015
WO 2016/069925 A1 5/2016
WO 2017/196647 A1 11/2017

OTHER PUBLICATIONS

Tokuriki et al., 2009, Curr. Opin. Struc. Biol. 19:596-604.*
Fenton et al. (2020, Medicinal Chemistry Research 29:1133-1146).*
Bhattacharya et al. (2017, PloS One 12(3): e0171355, https://doi.org/10.1371/journal.pone.0171355).*
Alaoui-Ismaili (2009, Cytokine Growth Factor Rev. 20(5-6):501-7).*
Guo et al. (2004, PNAS USA 101(25):9205-10).*
Ulloa-Aguirre et al. (2004, Traffic 5:821-837).*
Bernier et al. (2004, Curr. Opin. Pharmacol. 4:528-533).*
Vicky Wang-Wei Tsai, et al., "TGF-b Superfamily Cytokine MIC-1/GDF 15 Is a Physiological Appetite and Body Weight Regulator", PLOS One, Feb. 2013, pp. 1-10, vol. 8, Issue 2.
NCBI Reference Sequence XP_009251261.1, Feb. 28, 2018.
NCBI Reference Sequence XP_030676283.1, Sep. 17, 2019.
International Search Report for PCT/KR2020/016842 dated Mar. 17, 2021 [PCT/ISA/210].
Written Opinion for PCT/KR2020/016842 dated Mar. 17, 2021 [PCT/ISA/237].

* cited by examiner

*Primary Examiner* — Sudhakar Katakam
*Assistant Examiner* — Zachary J Miknis
(74) *Attorney, Agent, or Firm* — Sughrue Mion, PLLC

(57) ABSTRACT

A fusion protein including a GDF15 variant having increased physiological activity and in vivo stability, and a pharmaceutical composition containing the same are disclosed. The GDF15 variant or long-acting GDF15 fusion protein is superior to conventional GDF15 variants in terms of in vitro efficacy, binding affinity for GDF15 receptors, and body weight loss effect. Therefore, a pharmaceutical composition containing, as an active ingredient, the GDF15 variant, the long-acting GDF15 fusion protein, or a dimer of the fusion protein, causes appetite suppression, and thus can be effectively used as a therapeutic agent for metabolic diseases or obesity. Furthermore, the pharmaceutical composition can be used in combination therapy or the like with chemical drugs and other therapeutic agents for metabolic diseases, and can be effectively used in combination therapy with conventional therapeutic agents for metabolic diseases or obesity.

24 Claims, 8 Drawing Sheets

Specification includes a Sequence Listing.

[FIG. 1]
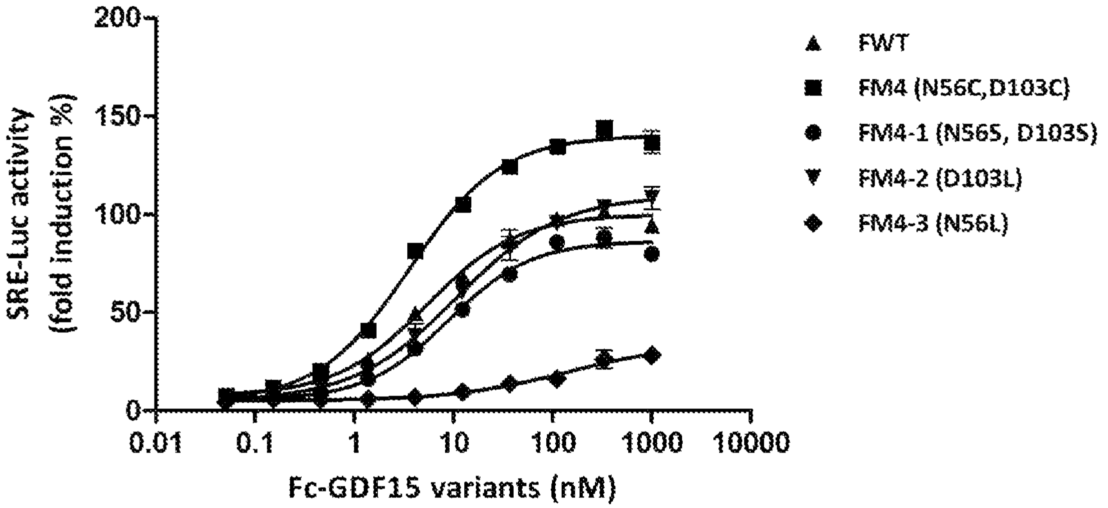
[FIG. 2]
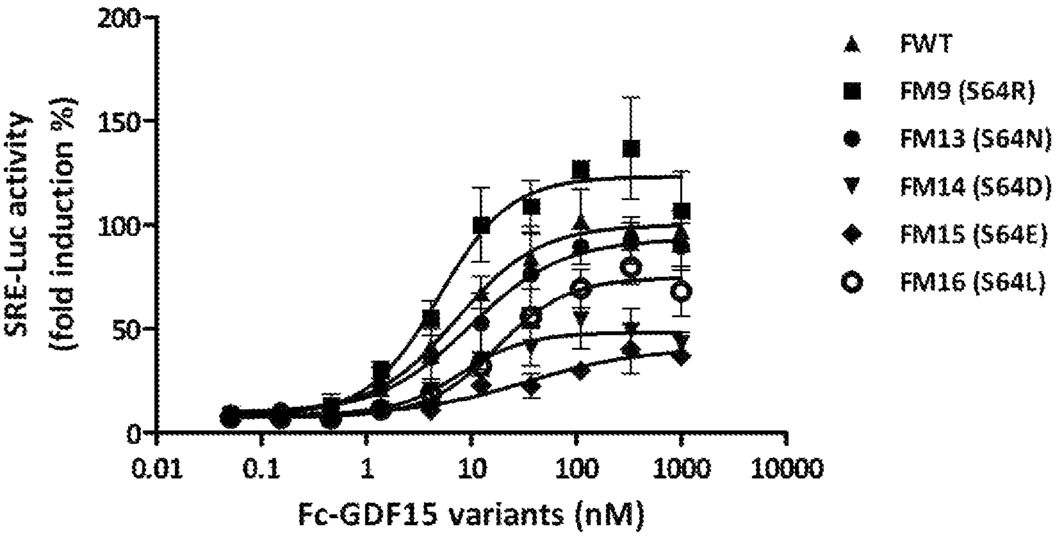

[FIG. 3]
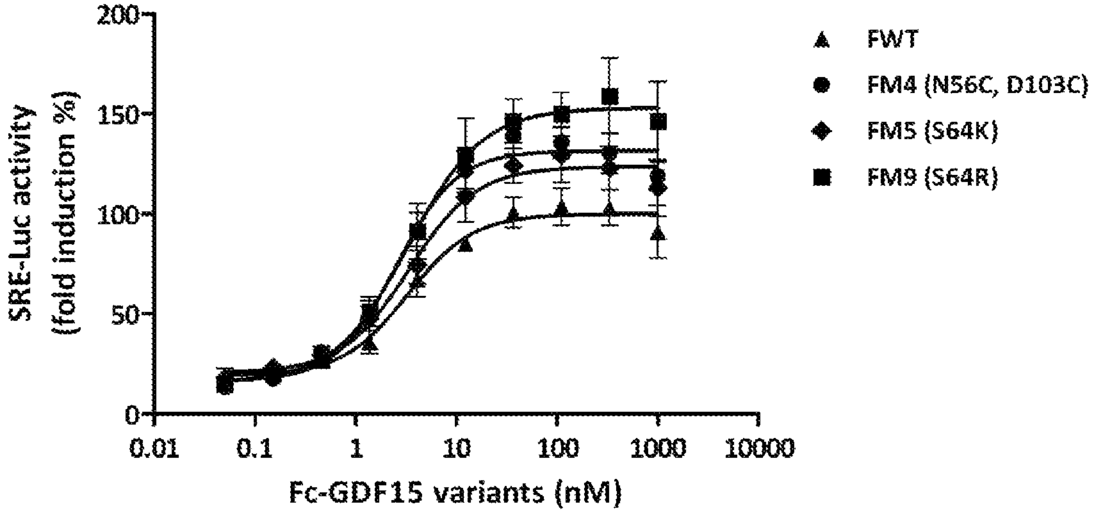
[FIG. 4]
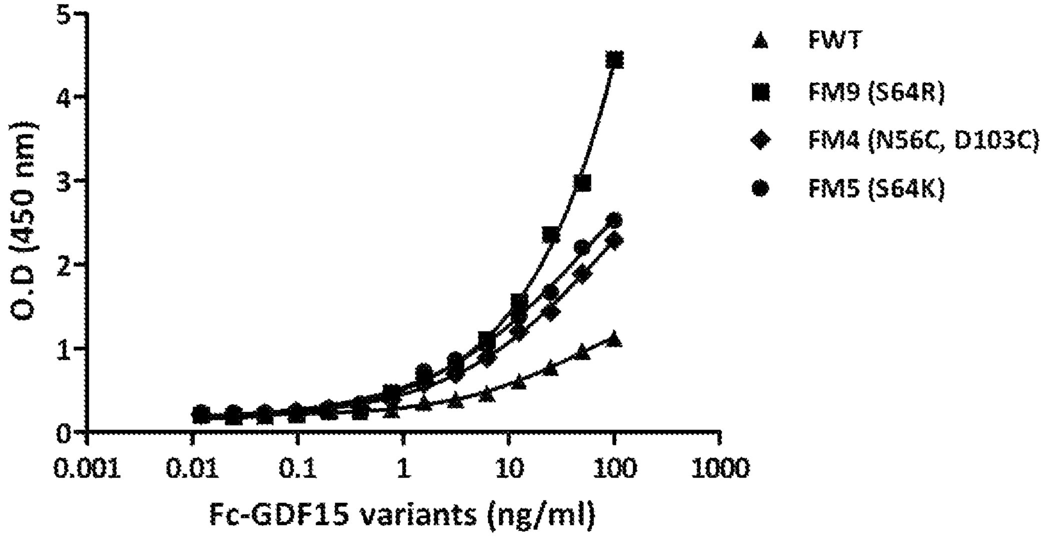

[FIG. 5]
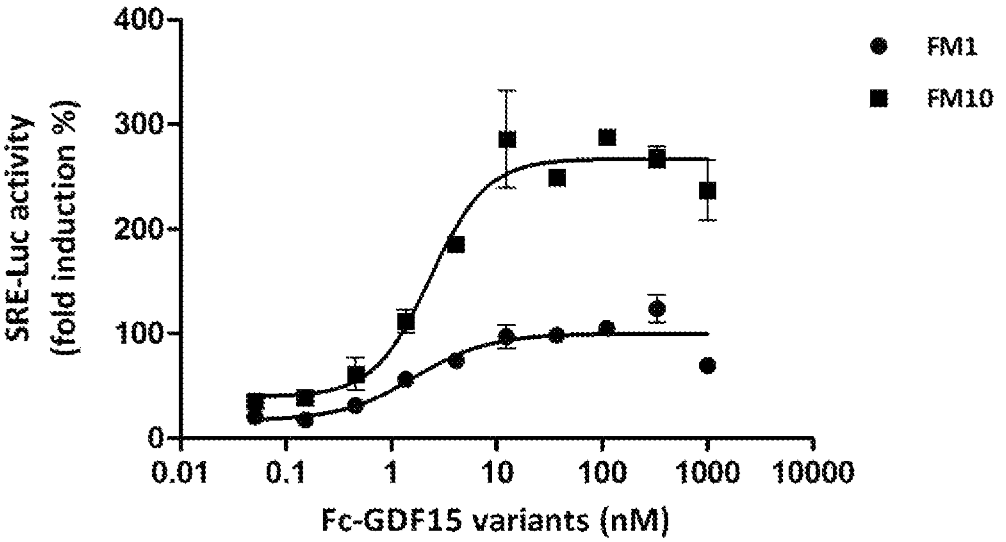
[FIG. 6]
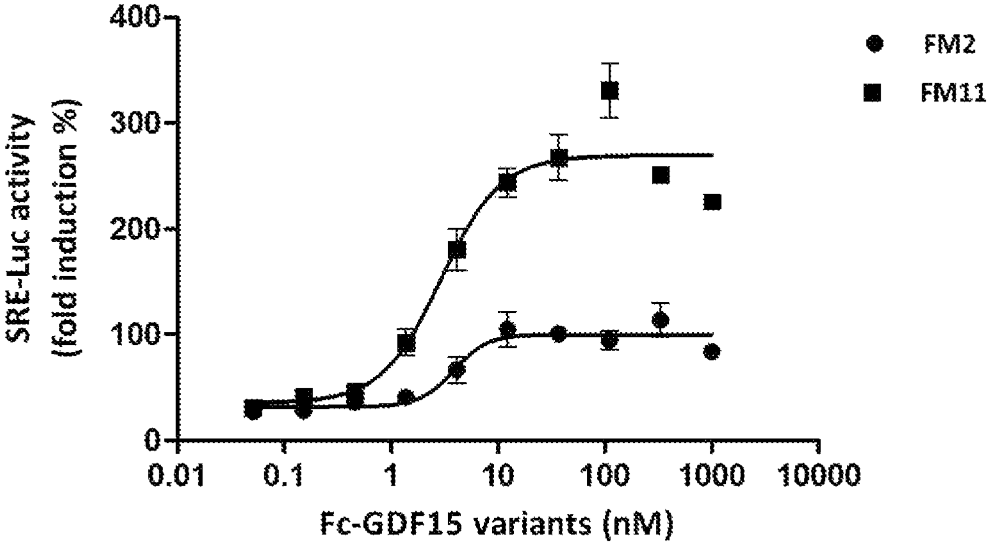

[FIG. 7]
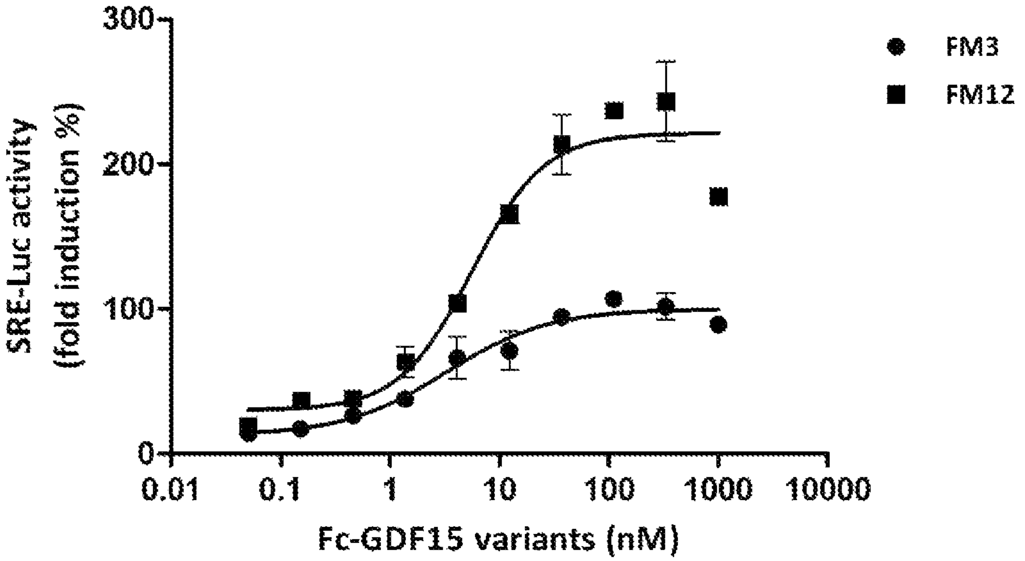
[FIG. 8]
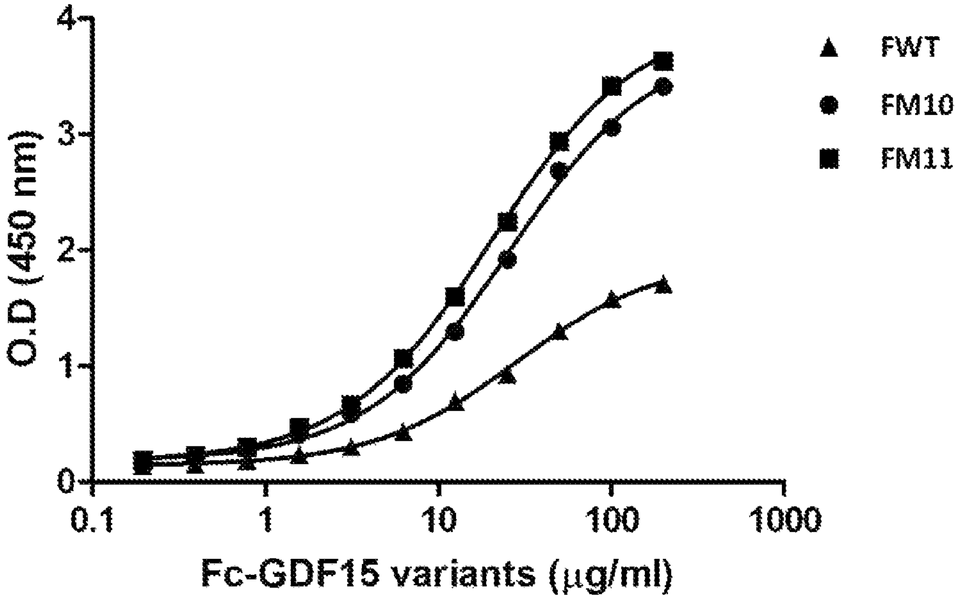

[FIG. 9]
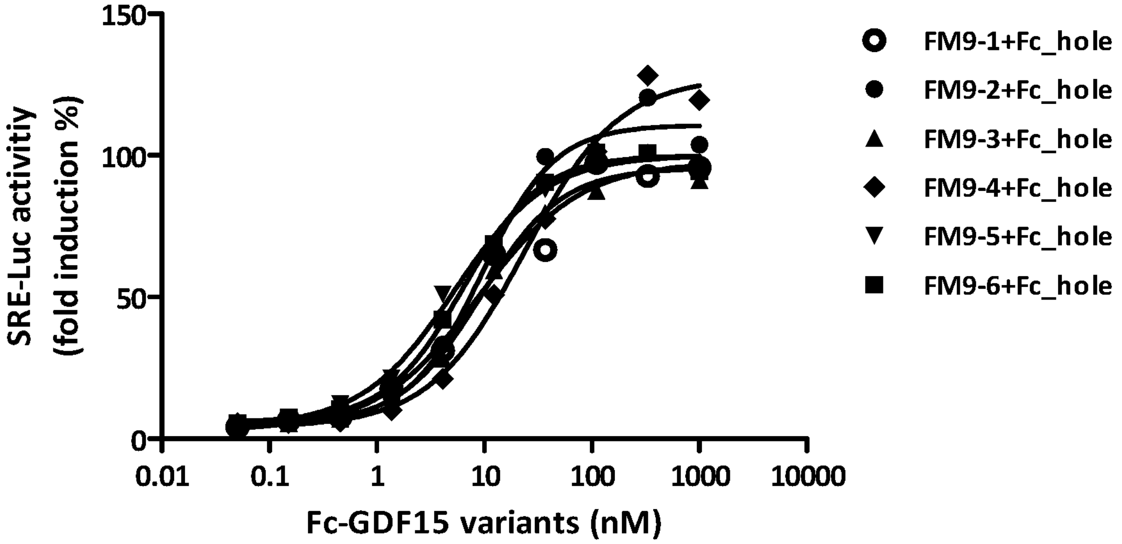
[FIG. 10]
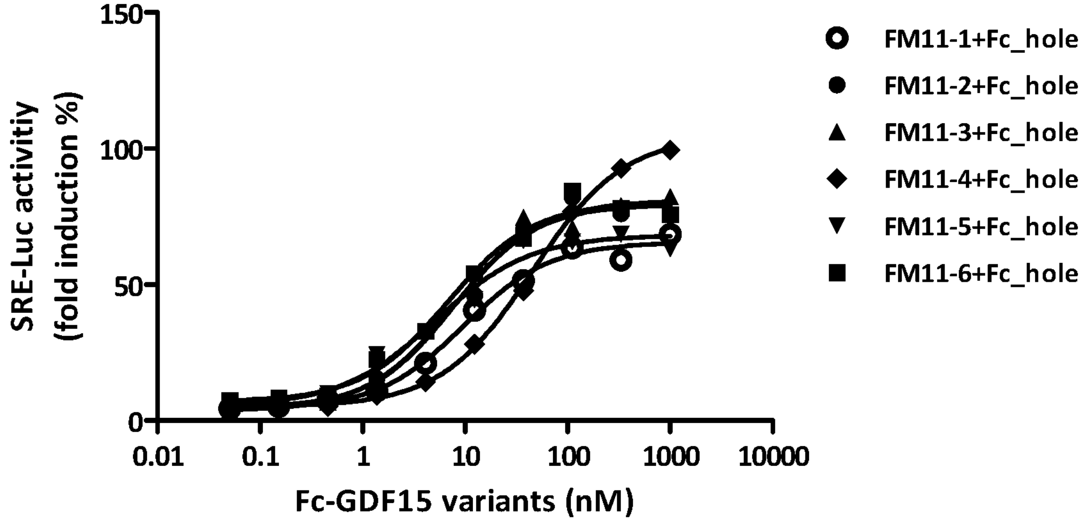

[FIG. 11]
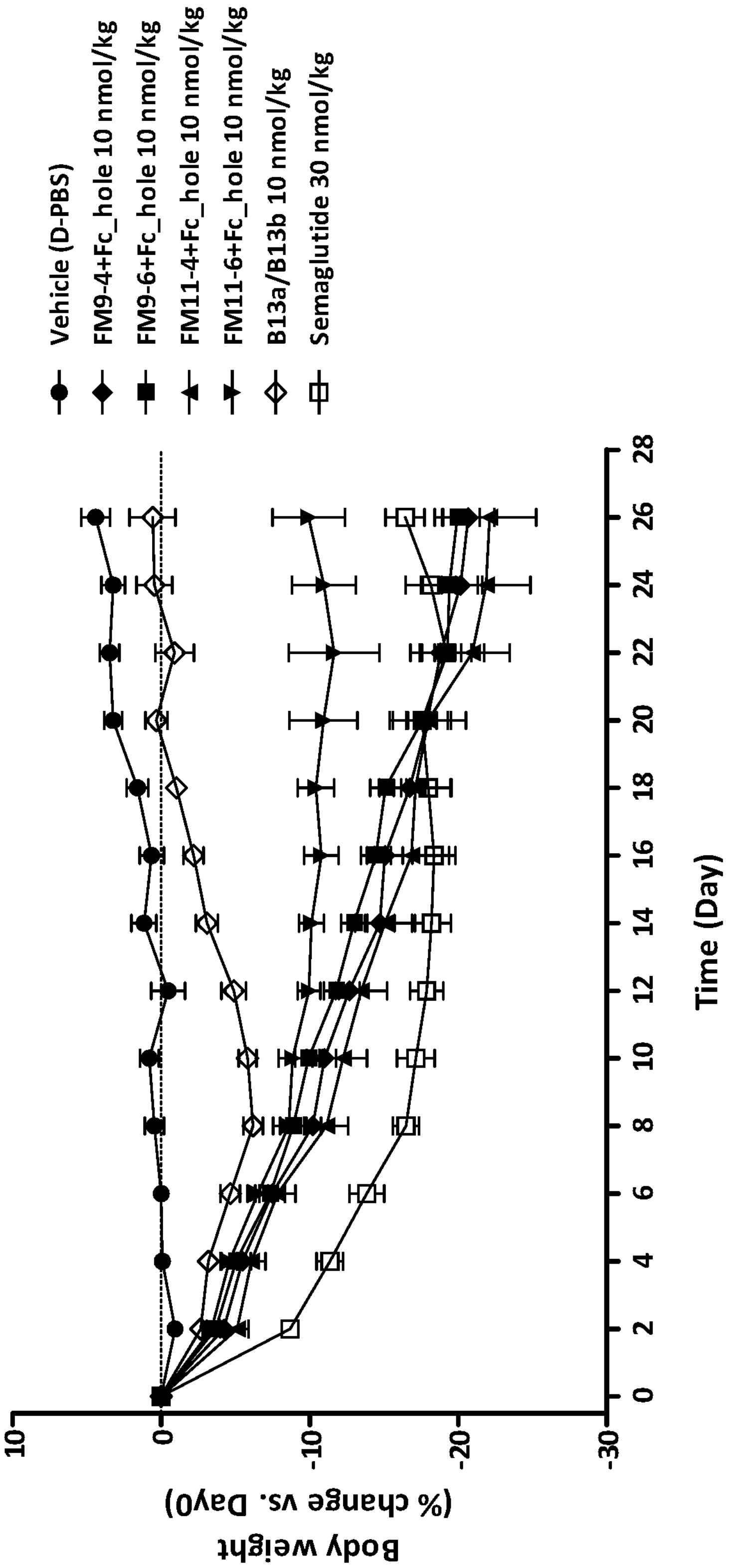

[FIG. 12]
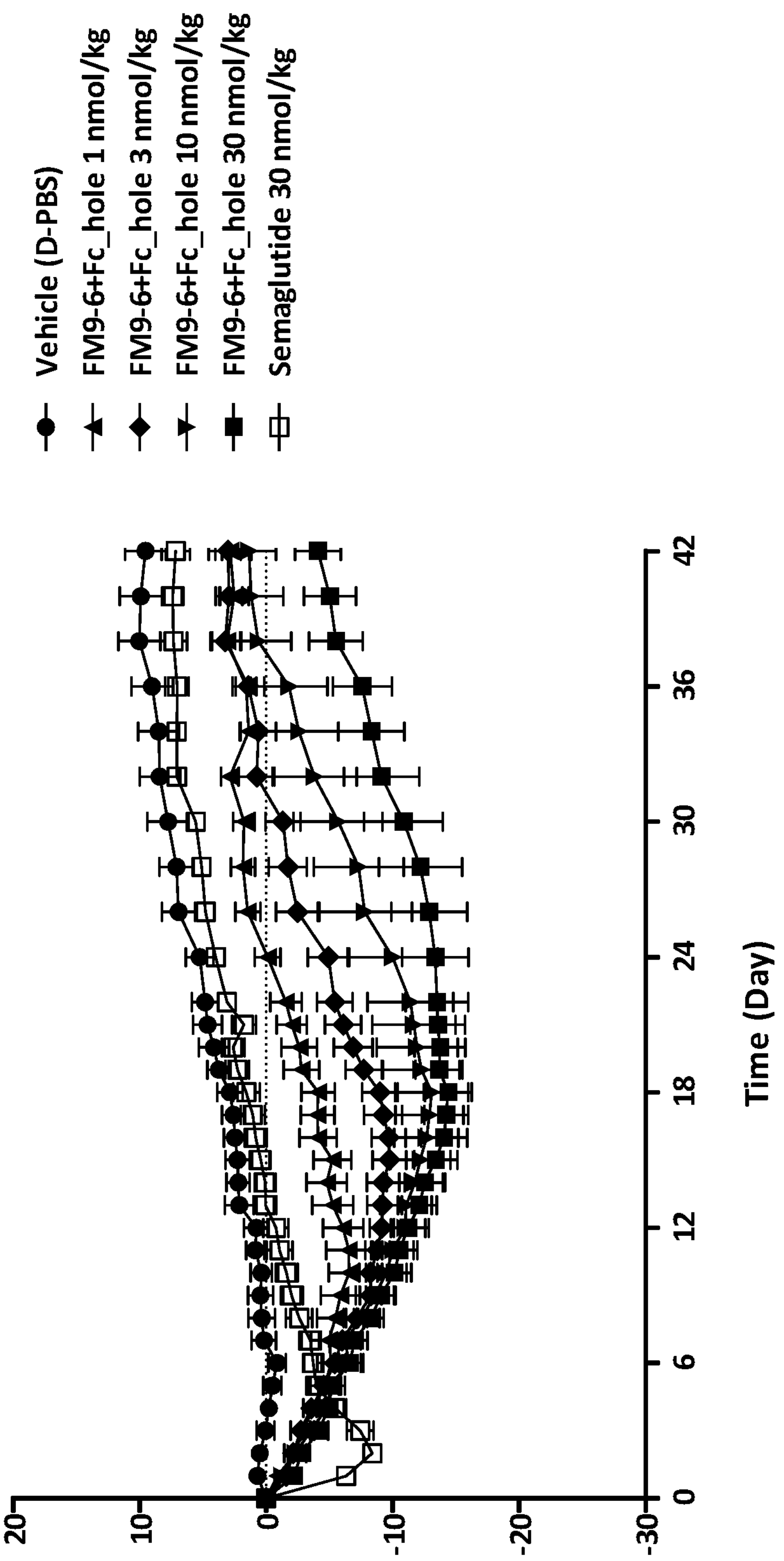

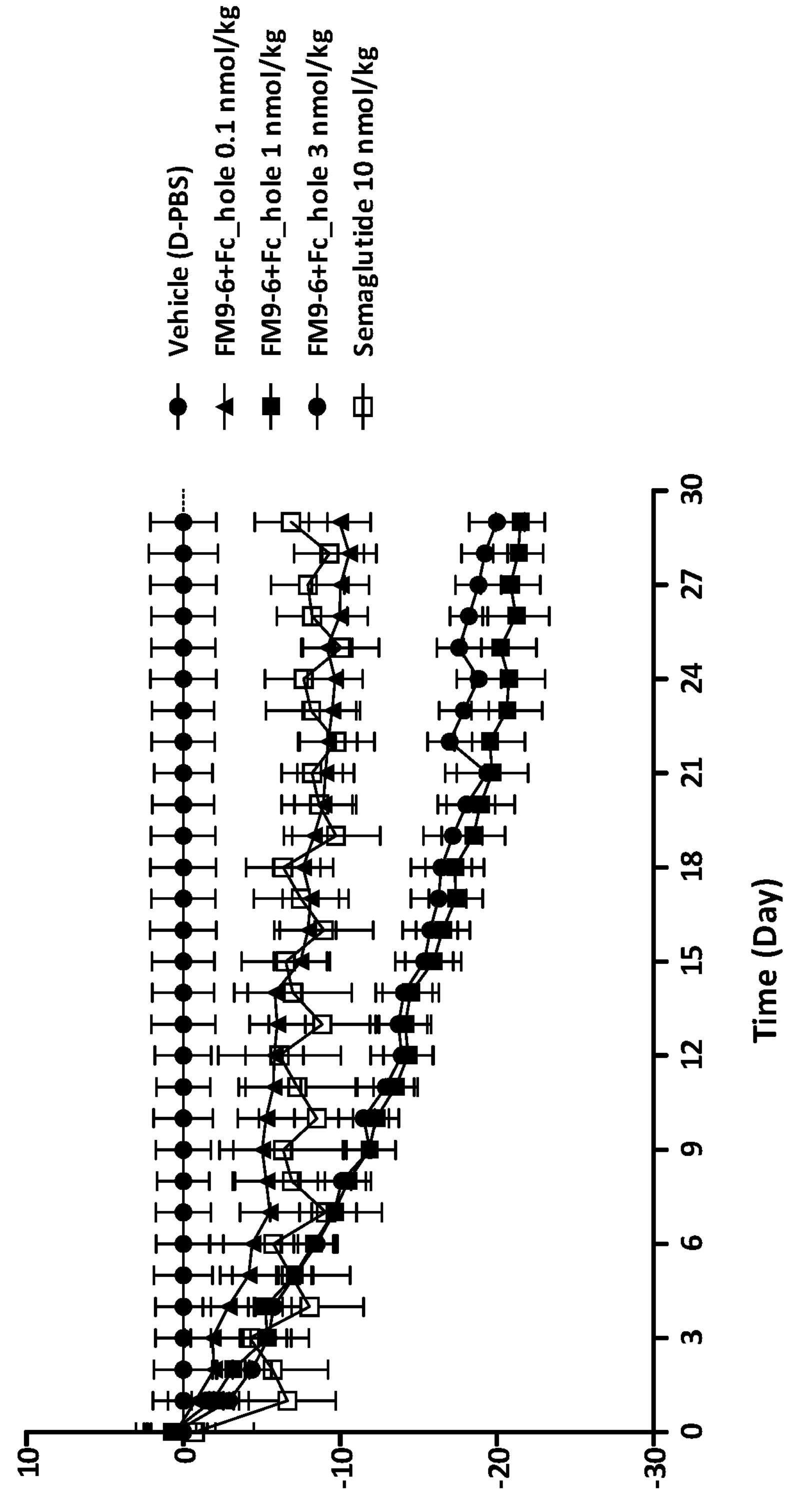
[FIG. 13]

SEQUENCE LISTING

```
<160> NUMBER OF SEQ ID NOS: 113

<210> SEQ ID NO 1
<211> LENGTH: 112
<212> TYPE: PRT
```

<213> ORGANISM: Homo sapiens

<400> SEQUENCE: 1

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 2
<211> LENGTH: 106
<212> TYPE: PRT
<213> ORGANISM: Artificial Sequence
<220> FEATURE:
<223> OTHER INFORMATION: Core Domain (R21X, N56X, S64X, D103X)
<220> FEATURE:
<221> NAME/KEY: MISC_FEATURE
<222> LOCATION: (15)
<223> OTHER INFORMATION: Xaa = Ala, Asp, Asn, Cys, Glu, Gln, Gly, His, Ile, Leu, Lys, Met, Phe, Pro, Ser, Thr, Trp, Tyr, or Val
<220> FEATURE:
<221> NAME/KEY: MISC_FEATURE
<222> LOCATION: (50)
<223> OTHER INFORMATION: Xaa = Ala, Arg, Asp, Cys, Glu, Gln, Gly, His, Ile, Leu, Lys, Met, Phe, Pro, Ser, Thr, Trp, Tyr, or Val
<220> FEATURE:
<221> NAME/KEY: MISC_FEATURE
<222> LOCATION: (58)
<223> OTHER INFORMATION: Xaa = Ala, Arg, Asp, Asn, Cys, Glu, Gln, Gly, His, Ile, Leu, Lys, Met, Phe, Pro, Thr, Trp, Tyr, or Val
<220> FEATURE:
<221> NAME/KEY: MISC_FEATURE
<222> LOCATION: (97)
<223> OTHER INFORMATION: Xaa = Ala, Arg, Asn, Cys, Glu, Gln, Gly, His, Ile, Leu, Lys, Met, Phe, Pro, Ser, Thr, Trp, Tyr, or Val

<400> SEQUENCE: 2

```
Cys Pro Leu Gly Pro Gly Arg Cys Cys Arg Leu His Thr Val Xaa Ala
1               5                   10                  15

Ser Leu Glu Asp Leu Gly Trp Ala Asp Trp Val Leu Ser Pro Arg Glu
            20                  25                  30

Val Gln Val Thr Met Cys Ile Gly Ala Cys Pro Ser Gln Phe Arg Ala
        35                  40                  45

Ala Xaa Met His Ala Gln Ile Lys Thr Xaa Leu His Arg Leu Lys Pro
    50                  55                  60

Asp Thr Val Pro Ala Pro Cys Cys Val Pro Ala Ser Tyr Asn Pro Met
65                  70                  75                  80

Val Leu Ile Gln Lys Thr Asp Thr Gly Val Ser Leu Gln Thr Tyr Asp
                85                  90                  95

Xaa Leu Leu Ala Lys Asp Cys His Cys Ile
            100                 105
```

<210> SEQ ID NO 3
<211> LENGTH: 5

<212> TYPE: PRT
<213> ORGANISM: Artificial Sequence
<220> FEATURE:
<223> OTHER INFORMATION: N-terminal extension domain I

<400> SEQUENCE: 3

Trp Ser Asn Ser Thr
1               5

<210> SEQ ID NO 4
<211> LENGTH: 3
<212> TYPE: PRT
<213> ORGANISM: Artificial Sequence
<220> FEATURE:
<223> OTHER INFORMATION: N-terminal extension domain II

<400> SEQUENCE: 4

Asn Ser Thr
1

<210> SEQ ID NO 5
<211> LENGTH: 4
<212> TYPE: PRT
<213> ORGANISM: Artificial Sequence
<220> FEATURE:
<223> OTHER INFORMATION: N-terminal extension domain III

<400> SEQUENCE: 5

Asn Gly Asp His
1

<210> SEQ ID NO 6
<211> LENGTH: 106
<212> TYPE: PRT
<213> ORGANISM: Artificial Sequence
<220> FEATURE:
<223> OTHER INFORMATION: Core Domain(R21N)

<400> SEQUENCE: 6

Cys Pro Leu Gly Pro Gly Arg Cys Cys Arg Leu His Thr Val Asn Ala
1               5                   10                  15

Ser Leu Glu Asp Leu Gly Trp Ala Asp Trp Val Leu Ser Pro Arg Glu
            20                  25                  30

Val Gln Val Thr Met Cys Ile Gly Ala Cys Pro Ser Gln Phe Arg Ala
        35                  40                  45

Ala Asn Met His Ala Gln Ile Lys Thr Ser Leu His Arg Leu Lys Pro
    50                  55                  60

Asp Thr Val Pro Ala Pro Cys Cys Val Pro Ala Ser Tyr Asn Pro Met
65                  70                  75                  80

Val Leu Ile Gln Lys Thr Asp Thr Gly Val Ser Leu Gln Thr Tyr Asp
                85                  90                  95

Asp Leu Leu Ala Lys Asp Cys His Cys Ile
            100                 105

<210> SEQ ID NO 7
<211> LENGTH: 106
<212> TYPE: PRT
<213> ORGANISM: Artificial Sequence
<220> FEATURE:
<223> OTHER INFORMATION: Core Domain(N56L)

<400> SEQUENCE: 7

Cys Pro Leu Gly Pro Gly Arg Cys Cys Arg Leu His Thr Val Arg Ala
1               5                   10                  15

Ser Leu Glu Asp Leu Gly Trp Ala Asp Trp Val Leu Ser Pro Arg Glu
20 25 30

Val Gln Val Thr Met Cys Ile Gly Ala Cys Pro Ser Gln Phe Arg Ala
35 40 45

Ala Leu Met His Ala Gln Ile Lys Thr Ser Leu His Arg Leu Lys Pro
50 55 60

Asp Thr Val Pro Ala Pro Cys Cys Val Pro Ala Ser Tyr Asn Pro Met
65 70 75 80

Val Leu Ile Gln Lys Thr Asp Thr Gly Val Ser Leu Gln Thr Tyr Asp
85 90 95

Asp Leu Leu Ala Lys Asp Cys His Cys Ile
100 105

<210> SEQ ID NO 8
<211> LENGTH: 106
<212> TYPE: PRT
<213> ORGANISM: Artificial Sequence
<220> FEATURE:
<223> OTHER INFORMATION: Core Domain(S64K)

<400> SEQUENCE: 8

Cys Pro Leu Gly Pro Gly Arg Cys Cys Arg Leu His Thr Val Arg Ala
1 5 10 15

Ser Leu Glu Asp Leu Gly Trp Ala Asp Trp Val Leu Ser Pro Arg Glu
20 25 30

Val Gln Val Thr Met Cys Ile Gly Ala Cys Pro Ser Gln Phe Arg Ala
35 40 45

Ala Asn Met His Ala Gln Ile Lys Thr Lys Leu His Arg Leu Lys Pro
50 55 60

Asp Thr Val Pro Ala Pro Cys Cys Val Pro Ala Ser Tyr Asn Pro Met
65 70 75 80

Val Leu Ile Gln Lys Thr Asp Thr Gly Val Ser Leu Gln Thr Tyr Asp
85 90 95

Asp Leu Leu Ala Lys Asp Cys His Cys Ile
100 105

<210> SEQ ID NO 9
<211> LENGTH: 106
<212> TYPE: PRT
<213> ORGANISM: Artificial Sequence
<220> FEATURE:
<223> OTHER INFORMATION: Core Domain(S64R)

<400> SEQUENCE: 9

Cys Pro Leu Gly Pro Gly Arg Cys Cys Arg Leu His Thr Val Arg Ala
1 5 10 15

Ser Leu Glu Asp Leu Gly Trp Ala Asp Trp Val Leu Ser Pro Arg Glu
20 25 30

Val Gln Val Thr Met Cys Ile Gly Ala Cys Pro Ser Gln Phe Arg Ala
35 40 45

Ala Asn Met His Ala Gln Ile Lys Thr Arg Leu His Arg Leu Lys Pro
50 55 60

Asp Thr Val Pro Ala Pro Cys Cys Val Pro Ala Ser Tyr Asn Pro Met
65 70 75 80

Val Leu Ile Gln Lys Thr Asp Thr Gly Val Ser Leu Gln Thr Tyr Asp
85 90 95

Asp Leu Leu Ala Lys Asp Cys His Cys Ile

```
            100                 105


<210> SEQ ID NO 10
<211> LENGTH: 106
<212> TYPE: PRT
<213> ORGANISM: Artificial Sequence
<220> FEATURE:
<223> OTHER INFORMATION: Core Domain(S64N)

<400> SEQUENCE: 10

Cys Pro Leu Gly Pro Gly Arg Cys Cys Arg Leu His Thr Val Arg Ala
1               5                   10                  15

Ser Leu Glu Asp Leu Gly Trp Ala Asp Trp Val Leu Ser Pro Arg Glu
            20                  25                  30

Val Gln Val Thr Met Cys Ile Gly Ala Cys Pro Ser Gln Phe Arg Ala
        35                  40                  45

Ala Asn Met His Ala Gln Ile Lys Thr Asn Leu His Arg Leu Lys Pro
    50                  55                  60

Asp Thr Val Pro Ala Pro Cys Cys Val Pro Ala Ser Tyr Asn Pro Met
65                  70                  75                  80

Val Leu Ile Gln Lys Thr Asp Thr Gly Val Ser Leu Gln Thr Tyr Asp
                85                  90                  95

Asp Leu Leu Ala Lys Asp Cys His Cys Ile
            100                 105


<210> SEQ ID NO 11
<211> LENGTH: 106
<212> TYPE: PRT
<213> ORGANISM: Artificial Sequence
<220> FEATURE:
<223> OTHER INFORMATION: Core Domain(S64D)

<400> SEQUENCE: 11

Cys Pro Leu Gly Pro Gly Arg Cys Cys Arg Leu His Thr Val Arg Ala
1               5                   10                  15

Ser Leu Glu Asp Leu Gly Trp Ala Asp Trp Val Leu Ser Pro Arg Glu
            20                  25                  30

Val Gln Val Thr Met Cys Ile Gly Ala Cys Pro Ser Gln Phe Arg Ala
        35                  40                  45

Ala Asn Met His Ala Gln Ile Lys Thr Asp Leu His Arg Leu Lys Pro
    50                  55                  60

Asp Thr Val Pro Ala Pro Cys Cys Val Pro Ala Ser Tyr Asn Pro Met
65                  70                  75                  80

Val Leu Ile Gln Lys Thr Asp Thr Gly Val Ser Leu Gln Thr Tyr Asp
                85                  90                  95

Asp Leu Leu Ala Lys Asp Cys His Cys Ile
            100                 105


<210> SEQ ID NO 12
<211> LENGTH: 106
<212> TYPE: PRT
<213> ORGANISM: Artificial Sequence
<220> FEATURE:
<223> OTHER INFORMATION: Core Domain(S64E)

<400> SEQUENCE: 12

Cys Pro Leu Gly Pro Gly Arg Cys Cys Arg Leu His Thr Val Arg Ala
1               5                   10                  15

Ser Leu Glu Asp Leu Gly Trp Ala Asp Trp Val Leu Ser Pro Arg Glu
            20                  25                  30
```

Val Gln Val Thr Met Cys Ile Gly Ala Cys Pro Ser Gln Phe Arg Ala
        35                  40                  45

Ala Asn Met His Ala Gln Ile Lys Thr Glu Leu His Arg Leu Lys Pro
    50                  55                  60

Asp Thr Val Pro Ala Pro Cys Cys Val Pro Ala Ser Tyr Asn Pro Met
65                  70                  75                  80

Val Leu Ile Gln Lys Thr Asp Thr Gly Val Ser Leu Gln Thr Tyr Asp
                85                  90                  95

Asp Leu Leu Ala Lys Asp Cys His Cys Ile
            100                 105

<210> SEQ ID NO 13
<211> LENGTH: 106
<212> TYPE: PRT
<213> ORGANISM: Artificial Sequence
<220> FEATURE:
<223> OTHER INFORMATION: Core Domain(S64C)

<400> SEQUENCE: 13

Cys Pro Leu Gly Pro Gly Arg Cys Cys Arg Leu His Thr Val Arg Ala
1               5                   10                  15

Ser Leu Glu Asp Leu Gly Trp Ala Asp Trp Val Leu Ser Pro Arg Glu
            20                  25                  30

Val Gln Val Thr Met Cys Ile Gly Ala Cys Pro Ser Gln Phe Arg Ala
        35                  40                  45

Ala Asn Met His Ala Gln Ile Lys Thr Cys Leu His Arg Leu Lys Pro
    50                  55                  60

Asp Thr Val Pro Ala Pro Cys Cys Val Pro Ala Ser Tyr Asn Pro Met
65                  70                  75                  80

Val Leu Ile Gln Lys Thr Asp Thr Gly Val Ser Leu Gln Thr Tyr Asp
                85                  90                  95

Asp Leu Leu Ala Lys Asp Cys His Cys Ile
            100                 105

<210> SEQ ID NO 14
<211> LENGTH: 106
<212> TYPE: PRT
<213> ORGANISM: Artificial Sequence
<220> FEATURE:
<223> OTHER INFORMATION: Core Domain(S64L)

<400> SEQUENCE: 14

Cys Pro Leu Gly Pro Gly Arg Cys Cys Arg Leu His Thr Val Arg Ala
1               5                   10                  15

Ser Leu Glu Asp Leu Gly Trp Ala Asp Trp Val Leu Ser Pro Arg Glu
            20                  25                  30

Val Gln Val Thr Met Cys Ile Gly Ala Cys Pro Ser Gln Phe Arg Ala
        35                  40                  45

Ala Asn Met His Ala Gln Ile Lys Thr Leu Leu His Arg Leu Lys Pro
    50                  55                  60

Asp Thr Val Pro Ala Pro Cys Cys Val Pro Ala Ser Tyr Asn Pro Met
65                  70                  75                  80

Val Leu Ile Gln Lys Thr Asp Thr Gly Val Ser Leu Gln Thr Tyr Asp
                85                  90                  95

Asp Leu Leu Ala Lys Asp Cys His Cys Ile
            100                 105

<210> SEQ ID NO 15
<211> LENGTH: 106
<212> TYPE: PRT
<213> ORGANISM: Artificial Sequence
<220> FEATURE:
<223> OTHER INFORMATION: Core Domain(D103L)

<400> SEQUENCE: 15

```
Cys Pro Leu Gly Pro Gly Arg Cys Cys Arg Leu His Thr Val Arg Ala
1               5                   10                  15

Ser Leu Glu Asp Leu Gly Trp Ala Asp Trp Val Leu Ser Pro Arg Glu
            20                  25                  30

Val Gln Val Thr Met Cys Ile Gly Ala Cys Pro Ser Gln Phe Arg Ala
        35                  40                  45

Ala Asn Met His Ala Gln Ile Lys Thr Ser Leu His Arg Leu Lys Pro
    50                  55                  60

Asp Thr Val Pro Ala Pro Cys Cys Val Pro Ala Ser Tyr Asn Pro Met
65                  70                  75                  80

Val Leu Ile Gln Lys Thr Asp Thr Gly Val Ser Leu Gln Thr Tyr Asp
                85                  90                  95

Leu Leu Leu Ala Lys Asp Cys His Cys Ile
            100                 105
```

<210> SEQ ID NO 16
<211> LENGTH: 106
<212> TYPE: PRT
<213> ORGANISM: Artificial Sequence
<220> FEATURE:
<223> OTHER INFORMATION: Core Domain(N56C, D103C)

<400> SEQUENCE: 16

```
Cys Pro Leu Gly Pro Gly Arg Cys Cys Arg Leu His Thr Val Arg Ala
1               5                   10                  15

Ser Leu Glu Asp Leu Gly Trp Ala Asp Trp Val Leu Ser Pro Arg Glu
            20                  25                  30

Val Gln Val Thr Met Cys Ile Gly Ala Cys Pro Ser Gln Phe Arg Ala
        35                  40                  45

Ala Cys Met His Ala Gln Ile Lys Thr Ser Leu His Arg Leu Lys Pro
    50                  55                  60

Asp Thr Val Pro Ala Pro Cys Cys Val Pro Ala Ser Tyr Asn Pro Met
65                  70                  75                  80

Val Leu Ile Gln Lys Thr Asp Thr Gly Val Ser Leu Gln Thr Tyr Asp
                85                  90                  95

Cys Leu Leu Ala Lys Asp Cys His Cys Ile
            100                 105
```

<210> SEQ ID NO 17
<211> LENGTH: 106
<212> TYPE: PRT
<213> ORGANISM: Artificial Sequence
<220> FEATURE:
<223> OTHER INFORMATION: Core Domain(N56S, D103S)

<400> SEQUENCE: 17

```
Cys Pro Leu Gly Pro Gly Arg Cys Cys Arg Leu His Thr Val Arg Ala
1               5                   10                  15

Ser Leu Glu Asp Leu Gly Trp Ala Asp Trp Val Leu Ser Pro Arg Glu
            20                  25                  30

Val Gln Val Thr Met Cys Ile Gly Ala Cys Pro Ser Gln Phe Arg Ala
        35                  40                  45
```

```
Ala Ser Met His Ala Gln Ile Lys Thr Ser Leu His Arg Leu Lys Pro
    50                  55                  60

Asp Thr Val Pro Ala Pro Cys Cys Val Pro Ala Ser Tyr Asn Pro Met
65                  70                  75                  80

Val Leu Ile Gln Lys Thr Asp Thr Gly Val Ser Leu Gln Thr Tyr Asp
                85                  90                  95

Ser Leu Leu Ala Lys Asp Cys His Cys Ile
            100                 105


<210> SEQ ID NO 18
<211> LENGTH: 106
<212> TYPE: PRT
<213> ORGANISM: Artificial Sequence
<220> FEATURE:
<223> OTHER INFORMATION: Core Domain(R21N, S64R)

<400> SEQUENCE: 18

Cys Pro Leu Gly Pro Gly Arg Cys Cys Arg Leu His Thr Val Asn Ala
1               5                   10                  15

Ser Leu Glu Asp Leu Gly Trp Ala Asp Trp Val Leu Ser Pro Arg Glu
            20                  25                  30

Val Gln Val Thr Met Cys Ile Gly Ala Cys Pro Ser Gln Phe Arg Ala
        35                  40                  45

Ala Asn Met His Ala Gln Ile Lys Thr Arg Leu His Arg Leu Lys Pro
    50                  55                  60

Asp Thr Val Pro Ala Pro Cys Cys Val Pro Ala Ser Tyr Asn Pro Met
65                  70                  75                  80

Val Leu Ile Gln Lys Thr Asp Thr Gly Val Ser Leu Gln Thr Tyr Asp
                85                  90                  95

Asp Leu Leu Ala Lys Asp Cys His Cys Ile
            100                 105


<210> SEQ ID NO 19
<211> LENGTH: 106
<212> TYPE: PRT
<213> ORGANISM: Artificial Sequence
<220> FEATURE:
<223> OTHER INFORMATION: Core Domain(R21N, S64K)

<400> SEQUENCE: 19

Cys Pro Leu Gly Pro Gly Arg Cys Cys Arg Leu His Thr Val Asn Ala
1               5                   10                  15

Ser Leu Glu Asp Leu Gly Trp Ala Asp Trp Val Leu Ser Pro Arg Glu
            20                  25                  30

Val Gln Val Thr Met Cys Ile Gly Ala Cys Pro Ser Gln Phe Arg Ala
        35                  40                  45

Ala Asn Met His Ala Gln Ile Lys Thr Lys Leu His Arg Leu Lys Pro
    50                  55                  60

Asp Thr Val Pro Ala Pro Cys Cys Val Pro Ala Ser Tyr Asn Pro Met
65                  70                  75                  80

Val Leu Ile Gln Lys Thr Asp Thr Gly Val Ser Leu Gln Thr Tyr Asp
                85                  90                  95

Asp Leu Leu Ala Lys Asp Cys His Cys Ile
            100                 105


<210> SEQ ID NO 20
<211> LENGTH: 106
<212> TYPE: PRT
```

<213> ORGANISM: Artificial Sequence
<220> FEATURE:
<223> OTHER INFORMATION: Core Domain(human GDF15 7-112aa)

<400> SEQUENCE: 20

```
Cys Pro Leu Gly Pro Gly Arg Cys Cys Arg Leu His Thr Val Arg Ala
1               5                   10                  15

Ser Leu Glu Asp Leu Gly Trp Ala Asp Trp Val Leu Ser Pro Arg Glu
            20                  25                  30

Val Gln Val Thr Met Cys Ile Gly Ala Cys Pro Ser Gln Phe Arg Ala
        35                  40                  45

Ala Asn Met His Ala Gln Ile Lys Thr Ser Leu His Arg Leu Lys Pro
    50                  55                  60

Asp Thr Val Pro Ala Pro Cys Cys Val Pro Ala Ser Tyr Asn Pro Met
65                  70                  75                  80

Val Leu Ile Gln Lys Thr Asp Thr Gly Val Ser Leu Gln Thr Tyr Asp
                85                  90                  95

Asp Leu Leu Ala Lys Asp Cys His Cys Ile
            100                 105
```

<210> SEQ ID NO 21
<211> LENGTH: 111
<212> TYPE: PRT
<213> ORGANISM: Artificial Sequence
<220> FEATURE:
<223> OTHER INFORMATION: GDF15 variant (delta N3, WS insertion, G4N, D5S, H6T/ FM1)

<400> SEQUENCE: 21

```
Trp Ser Asn Ser Thr Cys Pro Leu Gly Pro Gly Arg Cys Cys Arg Leu
1               5                   10                  15

His Thr Val Arg Ala Ser Leu Glu Asp Leu Gly Trp Ala Asp Trp Val
            20                  25                  30

Leu Ser Pro Arg Glu Val Gln Val Thr Met Cys Ile Gly Ala Cys Pro
        35                  40                  45

Ser Gln Phe Arg Ala Ala Asn Met His Ala Gln Ile Lys Thr Ser Leu
    50                  55                  60

His Arg Leu Lys Pro Asp Thr Val Pro Ala Pro Cys Cys Val Pro Ala
65                  70                  75                  80

Ser Tyr Asn Pro Met Val Leu Ile Gln Lys Thr Asp Thr Gly Val Ser
                85                  90                  95

Leu Gln Thr Tyr Asp Asp Leu Leu Ala Lys Asp Cys His Cys Ile
            100                 105                 110
```

<210> SEQ ID NO 22
<211> LENGTH: 109
<212> TYPE: PRT
<213> ORGANISM: Artificial Sequence
<220> FEATURE:
<223> OTHER INFORMATION: GDF15 variant (delta N3, G4N, D5S, H6T / FM2)

<400> SEQUENCE: 22

```
Asn Ser Thr Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Met Cys Ile Gly Ala Cys Pro Ser Gln
        35                  40                  45

Phe Arg Ala Ala Asn Met His Ala Gln Ile Lys Thr Ser Leu His Arg
```

```
    50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105


<210> SEQ ID NO 23
<211> LENGTH: 110
<212> TYPE: PRT
<213> ORGANISM: Artificial Sequence
<220> FEATURE:
<223> OTHER INFORMATION: GDF15 variant (delta N2, R21N / FM3)

<400> SEQUENCE: 23

Asn Gly Asp His Cys Pro Leu Gly Pro Gly Arg Cys Cys Arg Leu His
1               5                   10                  15

Thr Val Asn Ala Ser Leu Glu Asp Leu Gly Trp Ala Asp Trp Val Leu
            20                  25                  30

Ser Pro Arg Glu Val Gln Val Thr Met Cys Ile Gly Ala Cys Pro Ser
        35                  40                  45

Gln Phe Arg Ala Ala Asn Met His Ala Gln Ile Lys Thr Ser Leu His
    50                  55                  60

Arg Leu Lys Pro Asp Thr Val Pro Ala Pro Cys Cys Val Pro Ala Ser
65                  70                  75                  80

Tyr Asn Pro Met Val Leu Ile Gln Lys Thr Asp Thr Gly Val Ser Leu
                85                  90                  95

Gln Thr Tyr Asp Asp Leu Leu Ala Lys Asp Cys His Cys Ile
            100                 105                 110


<210> SEQ ID NO 24
<211> LENGTH: 110
<212> TYPE: PRT
<213> ORGANISM: Artificial Sequence
<220> FEATURE:
<223> OTHER INFORMATION: GDF15 variant (delta N2, N56L / FM4-3)

<400> SEQUENCE: 24

Asn Gly Asp His Cys Pro Leu Gly Pro Gly Arg Cys Cys Arg Leu His
1               5                   10                  15

Thr Val Arg Ala Ser Leu Glu Asp Leu Gly Trp Ala Asp Trp Val Leu
            20                  25                  30

Ser Pro Arg Glu Val Gln Val Thr Met Cys Ile Gly Ala Cys Pro Ser
        35                  40                  45

Gln Phe Arg Ala Ala Leu Met His Ala Gln Ile Lys Thr Ser Leu His
    50                  55                  60

Arg Leu Lys Pro Asp Thr Val Pro Ala Pro Cys Cys Val Pro Ala Ser
65                  70                  75                  80

Tyr Asn Pro Met Val Leu Ile Gln Lys Thr Asp Thr Gly Val Ser Leu
                85                  90                  95

Gln Thr Tyr Asp Asp Leu Leu Ala Lys Asp Cys His Cys Ile
            100                 105                 110


<210> SEQ ID NO 25
<211> LENGTH: 110
<212> TYPE: PRT
<213> ORGANISM: Artificial Sequence
<220> FEATURE:
```

<223> OTHER INFORMATION: GDF15 variant (delta N2, S64K / FM5)

<400> SEQUENCE: 25

Asn Gly Asp His Cys Pro Leu Gly Pro Gly Arg Cys Cys Arg Leu His
1               5                   10                  15

Thr Val Arg Ala Ser Leu Glu Asp Leu Gly Trp Ala Asp Trp Val Leu
            20                  25                  30

Ser Pro Arg Glu Val Gln Val Thr Met Cys Ile Gly Ala Cys Pro Ser
        35                  40                  45

Gln Phe Arg Ala Ala Asn Met His Ala Gln Ile Lys Thr Lys Leu His
    50                  55                  60

Arg Leu Lys Pro Asp Thr Val Pro Ala Pro Cys Cys Val Pro Ala Ser
65                  70                  75                  80

Tyr Asn Pro Met Val Leu Ile Gln Lys Thr Asp Thr Gly Val Ser Leu
                85                  90                  95

Gln Thr Tyr Asp Asp Leu Leu Ala Lys Asp Cys His Cys Ile
            100                 105                 110

<210> SEQ ID NO 26
<211> LENGTH: 111
<212> TYPE: PRT
<213> ORGANISM: Artificial Sequence
<220> FEATURE:
<223> OTHER INFORMATION: GDF15 variant (delta N3, WS insertion, G4N, D5S, H6T, S64K / FM6)

<400> SEQUENCE: 26

Trp Ser Asn Ser Thr Cys Pro Leu Gly Pro Gly Arg Cys Cys Arg Leu
1               5                   10                  15

His Thr Val Arg Ala Ser Leu Glu Asp Leu Gly Trp Ala Asp Trp Val
            20                  25                  30

Leu Ser Pro Arg Glu Val Gln Val Thr Met Cys Ile Gly Ala Cys Pro
        35                  40                  45

Ser Gln Phe Arg Ala Ala Asn Met His Ala Gln Ile Lys Thr Lys Leu
    50                  55                  60

His Arg Leu Lys Pro Asp Thr Val Pro Ala Pro Cys Cys Val Pro Ala
65                  70                  75                  80

Ser Tyr Asn Pro Met Val Leu Ile Gln Lys Thr Asp Thr Gly Val Ser
                85                  90                  95

Leu Gln Thr Tyr Asp Asp Leu Leu Ala Lys Asp Cys His Cys Ile
            100                 105                 110

<210> SEQ ID NO 27
<211> LENGTH: 109
<212> TYPE: PRT
<213> ORGANISM: Artificial Sequence
<220> FEATURE:
<223> OTHER INFORMATION: GDF15 variant (delta N3, G4N, D5S, H6T, S64K / FM7)

<400> SEQUENCE: 27

Asn Ser Thr Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Met Cys Ile Gly Ala Cys Pro Ser Gln
        35                  40                  45

Phe Arg Ala Ala Asn Met His Ala Gln Ile Lys Thr Lys Leu His Arg
    50                  55                  60

```
Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105


<210> SEQ ID NO 28
<211> LENGTH: 110
<212> TYPE: PRT
<213> ORGANISM: Artificial Sequence
<220> FEATURE:
<223> OTHER INFORMATION: GDF15 variant (delta N2, S64R / FM9)

<400> SEQUENCE: 28

Asn Gly Asp His Cys Pro Leu Gly Pro Gly Arg Cys Cys Arg Leu His
1               5                   10                  15

Thr Val Arg Ala Ser Leu Glu Asp Leu Gly Trp Ala Asp Trp Val Leu
            20                  25                  30

Ser Pro Arg Glu Val Gln Val Thr Met Cys Ile Gly Ala Cys Pro Ser
        35                  40                  45

Gln Phe Arg Ala Ala Asn Met His Ala Gln Ile Lys Thr Arg Leu His
    50                  55                  60

Arg Leu Lys Pro Asp Thr Val Pro Ala Pro Cys Cys Val Pro Ala Ser
65                  70                  75                  80

Tyr Asn Pro Met Val Leu Ile Gln Lys Thr Asp Thr Gly Val Ser Leu
                85                  90                  95

Gln Thr Tyr Asp Asp Leu Leu Ala Lys Asp Cys His Cys Ile
            100                 105                 110


<210> SEQ ID NO 29
<211> LENGTH: 111
<212> TYPE: PRT
<213> ORGANISM: Artificial Sequence
<220> FEATURE:
<223> OTHER INFORMATION: GDF15 variant (delta N3, WS insertion, G4N,
      D5S, H6T, S64R/ FM10)

<400> SEQUENCE: 29

Trp Ser Asn Ser Thr Cys Pro Leu Gly Pro Gly Arg Cys Cys Arg Leu
1               5                   10                  15

His Thr Val Arg Ala Ser Leu Glu Asp Leu Gly Trp Ala Asp Trp Val
            20                  25                  30

Leu Ser Pro Arg Glu Val Gln Val Thr Met Cys Ile Gly Ala Cys Pro
        35                  40                  45

Ser Gln Phe Arg Ala Ala Asn Met His Ala Gln Ile Lys Thr Arg Leu
    50                  55                  60

His Arg Leu Lys Pro Asp Thr Val Pro Ala Pro Cys Cys Val Pro Ala
65                  70                  75                  80

Ser Tyr Asn Pro Met Val Leu Ile Gln Lys Thr Asp Thr Gly Val Ser
                85                  90                  95

Leu Gln Thr Tyr Asp Asp Leu Leu Ala Lys Asp Cys His Cys Ile
            100                 105                 110


<210> SEQ ID NO 30
<211> LENGTH: 109
<212> TYPE: PRT
<213> ORGANISM: Artificial Sequence
<220> FEATURE:
```

<223> OTHER INFORMATION: GDF15 variant (delta N3, G4N, D5S, H6T, S64R/ FM11)

<400> SEQUENCE: 30

```
Asn Ser Thr Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Met Cys Ile Gly Ala Cys Pro Ser Gln
        35                  40                  45

Phe Arg Ala Ala Asn Met His Ala Gln Ile Lys Thr Arg Leu His Arg
    50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105
```

<210> SEQ ID NO 31
<211> LENGTH: 110
<212> TYPE: PRT
<213> ORGANISM: Artificial Sequence
<220> FEATURE:
<223> OTHER INFORMATION: GDF15 variant (delta N2, S64N/ FM13)

<400> SEQUENCE: 31

```
Asn Gly Asp His Cys Pro Leu Gly Pro Gly Arg Cys Cys Arg Leu His
1               5                   10                  15

Thr Val Arg Ala Ser Leu Glu Asp Leu Gly Trp Ala Asp Trp Val Leu
            20                  25                  30

Ser Pro Arg Glu Val Gln Val Thr Met Cys Ile Gly Ala Cys Pro Ser
        35                  40                  45

Gln Phe Arg Ala Ala Asn Met His Ala Gln Ile Lys Thr Asn Leu His
    50                  55                  60

Arg Leu Lys Pro Asp Thr Val Pro Ala Pro Cys Cys Val Pro Ala Ser
65                  70                  75                  80

Tyr Asn Pro Met Val Leu Ile Gln Lys Thr Asp Thr Gly Val Ser Leu
                85                  90                  95

Gln Thr Tyr Asp Asp Leu Leu Ala Lys Asp Cys His Cys Ile
            100                 105                 110
```

<210> SEQ ID NO 32
<211> LENGTH: 110
<212> TYPE: PRT
<213> ORGANISM: Artificial Sequence
<220> FEATURE:
<223> OTHER INFORMATION: GDF15 variant (delta N2,S64D/ FM14)

<400> SEQUENCE: 32

```
Asn Gly Asp His Cys Pro Leu Gly Pro Gly Arg Cys Cys Arg Leu His
1               5                   10                  15

Thr Val Arg Ala Ser Leu Glu Asp Leu Gly Trp Ala Asp Trp Val Leu
            20                  25                  30

Ser Pro Arg Glu Val Gln Val Thr Met Cys Ile Gly Ala Cys Pro Ser
        35                  40                  45

Gln Phe Arg Ala Ala Asn Met His Ala Gln Ile Lys Thr Asp Leu His
    50                  55                  60
```

```
Arg Leu Lys Pro Asp Thr Val Pro Ala Pro Cys Cys Val Pro Ala Ser
65                  70                  75                  80

Tyr Asn Pro Met Val Leu Ile Gln Lys Thr Asp Thr Gly Val Ser Leu
                85                  90                  95

Gln Thr Tyr Asp Asp Leu Leu Ala Lys Asp Cys His Cys Ile
            100                 105                 110


<210> SEQ ID NO 33
<211> LENGTH: 110
<212> TYPE: PRT
<213> ORGANISM: Artificial Sequence
<220> FEATURE:
<223> OTHER INFORMATION: GDF15 variant (delta N2,S64E/ FM15)

<400> SEQUENCE: 33

Asn Gly Asp His Cys Pro Leu Gly Pro Gly Arg Cys Cys Arg Leu His
1               5                   10                  15

Thr Val Arg Ala Ser Leu Glu Asp Leu Gly Trp Ala Asp Trp Val Leu
            20                  25                  30

Ser Pro Arg Glu Val Gln Val Thr Met Cys Ile Gly Ala Cys Pro Ser
        35                  40                  45

Gln Phe Arg Ala Ala Asn Met His Ala Gln Ile Lys Thr Glu Leu His
    50                  55                  60

Arg Leu Lys Pro Asp Thr Val Pro Ala Pro Cys Cys Val Pro Ala Ser
65                  70                  75                  80

Tyr Asn Pro Met Val Leu Ile Gln Lys Thr Asp Thr Gly Val Ser Leu
                85                  90                  95

Gln Thr Tyr Asp Asp Leu Leu Ala Lys Asp Cys His Cys Ile
            100                 105                 110


<210> SEQ ID NO 34
<211> LENGTH: 110
<212> TYPE: PRT
<213> ORGANISM: Artificial Sequence
<220> FEATURE:
<223> OTHER INFORMATION: GDF15 variant (delta N2,S64L / FM16)

<400> SEQUENCE: 34

Asn Gly Asp His Cys Pro Leu Gly Pro Gly Arg Cys Cys Arg Leu His
1               5                   10                  15

Thr Val Arg Ala Ser Leu Glu Asp Leu Gly Trp Ala Asp Trp Val Leu
            20                  25                  30

Ser Pro Arg Glu Val Gln Val Thr Met Cys Ile Gly Ala Cys Pro Ser
        35                  40                  45

Gln Phe Arg Ala Ala Asn Met His Ala Gln Ile Lys Thr Leu Leu His
    50                  55                  60

Arg Leu Lys Pro Asp Thr Val Pro Ala Pro Cys Cys Val Pro Ala Ser
65                  70                  75                  80

Tyr Asn Pro Met Val Leu Ile Gln Lys Thr Asp Thr Gly Val Ser Leu
                85                  90                  95

Gln Thr Tyr Asp Asp Leu Leu Ala Lys Asp Cys His Cys Ile
            100                 105                 110


<210> SEQ ID NO 35
<211> LENGTH: 110
<212> TYPE: PRT
<213> ORGANISM: Artificial Sequence
<220> FEATURE:
<223> OTHER INFORMATION: GDF15 variant (delta N2, D103L / FM4-2)
```

```
<400> SEQUENCE: 35

Asn Gly Asp His Cys Pro Leu Gly Pro Gly Arg Cys Cys Arg Leu His
1               5                   10                  15

Thr Val Arg Ala Ser Leu Glu Asp Leu Gly Trp Ala Asp Trp Val Leu
            20                  25                  30

Ser Pro Arg Glu Val Gln Val Thr Met Cys Ile Gly Ala Cys Pro Ser
        35                  40                  45

Gln Phe Arg Ala Ala Asn Met His Ala Gln Ile Lys Thr Ser Leu His
    50                  55                  60

Arg Leu Lys Pro Asp Thr Val Pro Ala Pro Cys Cys Val Pro Ala Ser
65                  70                  75                  80

Tyr Asn Pro Met Val Leu Ile Gln Lys Thr Asp Thr Gly Val Ser Leu
                85                  90                  95

Gln Thr Tyr Asp Leu Leu Leu Ala Lys Asp Cys His Cys Ile
            100                 105                 110


<210> SEQ ID NO 36
<211> LENGTH: 110
<212> TYPE: PRT
<213> ORGANISM: Artificial Sequence
<220> FEATURE:
<223> OTHER INFORMATION: GDF15 variant (delta N2, N56C, D103C / FM4)

<400> SEQUENCE: 36

Asn Gly Asp His Cys Pro Leu Gly Pro Gly Arg Cys Cys Arg Leu His
1               5                   10                  15

Thr Val Arg Ala Ser Leu Glu Asp Leu Gly Trp Ala Asp Trp Val Leu
            20                  25                  30

Ser Pro Arg Glu Val Gln Val Thr Met Cys Ile Gly Ala Cys Pro Ser
        35                  40                  45

Gln Phe Arg Ala Ala Cys Met His Ala Gln Ile Lys Thr Ser Leu His
    50                  55                  60

Arg Leu Lys Pro Asp Thr Val Pro Ala Pro Cys Cys Val Pro Ala Ser
65                  70                  75                  80

Tyr Asn Pro Met Val Leu Ile Gln Lys Thr Asp Thr Gly Val Ser Leu
                85                  90                  95

Gln Thr Tyr Asp Cys Leu Leu Ala Lys Asp Cys His Cys Ile
            100                 105                 110


<210> SEQ ID NO 37
<211> LENGTH: 110
<212> TYPE: PRT
<213> ORGANISM: Artificial Sequence
<220> FEATURE:
<223> OTHER INFORMATION: GDF15 variant (delta N2, N56S, D103S/ FM4-1)

<400> SEQUENCE: 37

Asn Gly Asp His Cys Pro Leu Gly Pro Gly Arg Cys Cys Arg Leu His
1               5                   10                  15

Thr Val Arg Ala Ser Leu Glu Asp Leu Gly Trp Ala Asp Trp Val Leu
            20                  25                  30

Ser Pro Arg Glu Val Gln Val Thr Met Cys Ile Gly Ala Cys Pro Ser
        35                  40                  45

Gln Phe Arg Ala Ala Ser Met His Ala Gln Ile Lys Thr Ser Leu His
    50                  55                  60

Arg Leu Lys Pro Asp Thr Val Pro Ala Pro Cys Cys Val Pro Ala Ser
65                  70                  75                  80
```

```
Tyr Asn Pro Met Val Leu Ile Gln Lys Thr Asp Thr Gly Val Ser Leu
                85                  90                  95

Gln Thr Tyr Asp Ser Leu Leu Ala Lys Asp Cys His Cys Ile
            100                 105                 110


<210> SEQ ID NO 38
<211> LENGTH: 110
<212> TYPE: PRT
<213> ORGANISM: Artificial Sequence
<220> FEATURE:
<223> OTHER INFORMATION: GDF15 variant (delta N2, R21N, S64K / FM8)

<400> SEQUENCE: 38

Asn Gly Asp His Cys Pro Leu Gly Pro Gly Arg Cys Cys Arg Leu His
1               5                   10                  15

Thr Val Asn Ala Ser Leu Glu Asp Leu Gly Trp Ala Asp Trp Val Leu
            20                  25                  30

Ser Pro Arg Glu Val Gln Val Thr Met Cys Ile Gly Ala Cys Pro Ser
        35                  40                  45

Gln Phe Arg Ala Ala Asn Met His Ala Gln Ile Lys Thr Lys Leu His
    50                  55                  60

Arg Leu Lys Pro Asp Thr Val Pro Ala Pro Cys Cys Val Pro Ala Ser
65                  70                  75                  80

Tyr Asn Pro Met Val Leu Ile Gln Lys Thr Asp Thr Gly Val Ser Leu
                85                  90                  95

Gln Thr Tyr Asp Asp Leu Leu Ala Lys Asp Cys His Cys Ile
            100                 105                 110


<210> SEQ ID NO 39
<211> LENGTH: 110
<212> TYPE: PRT
<213> ORGANISM: Artificial Sequence
<220> FEATURE:
<223> OTHER INFORMATION: GDF15 variant (delta N2, R21N, S64R / FM12)

<400> SEQUENCE: 39

Asn Gly Asp His Cys Pro Leu Gly Pro Gly Arg Cys Cys Arg Leu His
1               5                   10                  15

Thr Val Asn Ala Ser Leu Glu Asp Leu Gly Trp Ala Asp Trp Val Leu
            20                  25                  30

Ser Pro Arg Glu Val Gln Val Thr Met Cys Ile Gly Ala Cys Pro Ser
        35                  40                  45

Gln Phe Arg Ala Ala Asn Met His Ala Gln Ile Lys Thr Arg Leu His
    50                  55                  60

Arg Leu Lys Pro Asp Thr Val Pro Ala Pro Cys Cys Val Pro Ala Ser
65                  70                  75                  80

Tyr Asn Pro Met Val Leu Ile Gln Lys Thr Asp Thr Gly Val Ser Leu
                85                  90                  95

Gln Thr Tyr Asp Asp Leu Leu Ala Lys Asp Cys His Cys Ile
            100                 105                 110


<210> SEQ ID NO 40
<211> LENGTH: 110
<212> TYPE: PRT
<213> ORGANISM: Artificial Sequence
<220> FEATURE:
<223> OTHER INFORMATION: GDF15 (delta N2)

<400> SEQUENCE: 40

Asn Gly Asp His Cys Pro Leu Gly Pro Gly Arg Cys Cys Arg Leu His
```

-continued

```
1               5                   10                  15

Thr Val Arg Ala Ser Leu Glu Asp Leu Gly Trp Ala Asp Trp Val Leu
            20                  25                  30

Ser Pro Arg Glu Val Gln Val Thr Met Cys Ile Gly Ala Cys Pro Ser
        35                  40                  45

Gln Phe Arg Ala Ala Asn Met His Ala Gln Ile Lys Thr Ser Leu His
    50                  55                  60

Arg Leu Lys Pro Asp Thr Val Pro Ala Pro Cys Cys Val Pro Ala Ser
65                  70                  75                  80

Tyr Asn Pro Met Val Leu Ile Gln Lys Thr Asp Thr Gly Val Ser Leu
                85                  90                  95

Gln Thr Tyr Asp Asp Leu Leu Ala Lys Asp Cys His Cys Ile
            100                 105                 110


<210> SEQ ID NO 41
<211> LENGTH: 227
<212> TYPE: PRT
<213> ORGANISM: Artificial Sequence
<220> FEATURE:
<223> OTHER INFORMATION: Human IgG1 Fc

<400> SEQUENCE: 41

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 42
<211> LENGTH: 217
<212> TYPE: PRT
```

<213> ORGANISM: Artificial Sequence
<220> FEATURE:
<223> OTHER INFORMATION: Hinge deleted human IgG1-Fc(E233A, L235A)(T366W)-(A-1)

<400> SEQUENCE: 42

```
Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 43
<211> LENGTH: 217
<212> TYPE: PRT
<213> ORGANISM: Artificial Sequence
<220> FEATURE:
<223> OTHER INFORMATION: Hinge deleted human IgG1-Fc(E233A, L235A)(T366S, L368A, Y407V)-(A-2)

<400> SEQUENCE: 43

```
Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
```

```
            100                 105                 110

Pro Arg Glu Pro Gln Val Tyr Thr Leu Pro Pro Ser Arg Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215


<210> SEQ ID NO 44
<211> LENGTH: 217
<212> TYPE: PRT
<213> ORGANISM: Artificial Sequence
<220> FEATURE:
<223> OTHER INFORMATION: Hinge deleted human IgG1-Fc(E233A, L235A,
      N297A)(T366W)-(B-1)

<400> SEQUENCE: 44

Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Ala Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215


<210> SEQ ID NO 45
<211> LENGTH: 217
```

<212> TYPE: PRT
<213> ORGANISM: Artificial Sequence
<220> FEATURE:
<223> OTHER INFORMATION: Hinge deleted human IgG1-Fc(E233A, L235A, N297A)(T366S, L368A, Y407V)-(B-2)

<400> SEQUENCE: 45

```
Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Ala Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 46
<211> LENGTH: 217
<212> TYPE: PRT
<213> ORGANISM: Artificial Sequence
<220> FEATURE:
<223> OTHER INFORMATION: Hinge deleted human IgG1-Fc(L234A, L235A, N297A)(T366W)-(C-1)

<400> SEQUENCE: 46

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Ala Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95
```

```
Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215


<210> SEQ ID NO 47
<211> LENGTH: 217
<212> TYPE: PRT
<213> ORGANISM: Artificial Sequence
<220> FEATURE:
<223> OTHER INFORMATION: Hinge deleted human IgG1-Fc(L234A, L235A,
      N297A)(T366S, L368A, Y407V)-(C-2)

<400> SEQUENCE: 47

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Ala Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215


<210> SEQ ID NO 48
```

<211> LENGTH: 25
<212> TYPE: PRT
<213> ORGANISM: Artificial Sequence
<220> FEATURE:
<223> OTHER INFORMATION: linker-(G4S)5

<400> SEQUENCE: 48

```
Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

<210> SEQ ID NO 49
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)(T366W)-(G4S)5-GDF15(delta N2) - FWT

<400> SEQUENCE: 49

```
Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255

Leu His Thr Val Arg Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285
```

```
Pro Ser Gln Phe Arg Ala Ala Asn Met His Ala Gln Ile Lys Thr Ser
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Thr Asp Thr Gly Val
                325                 330                 335

Ser Leu Gln Thr Tyr Asp Asp Leu Leu Ala Lys Asp Cys His Cys Ile
            340                 345                 350


<210> SEQ ID NO 50
<211> LENGTH: 353
<212> TYPE: PRT
<213> ORGANISM: Artificial Sequence
<220> FEATURE:
<223> OTHER INFORMATION: Hinge deleted human IgG1-Fc(E233A, L235A)
      (T366W)-(G4S)5-GDF15 variant (delta N3, WS insertion, G4N, D5S,
      H6T)-FM1

<400> SEQUENCE: 50

Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Trp Ser Asn Ser Thr Cys Pro Leu Gly Pro Gly Arg Cys Cys
                245                 250                 255

Arg Leu His Thr Val Arg Ala Ser Leu Glu Asp Leu Gly Trp Ala Asp
            260                 265                 270

Trp Val Leu Ser Pro Arg Glu Val Gln Val Thr Met Cys Ile Gly Ala
        275                 280                 285

Cys Pro Ser Gln Phe Arg Ala Ala Asn Met His Ala Gln Ile Lys Thr
```

```
    290                 295                 300

Ser Leu His Arg Leu Lys Pro Asp Thr Val Pro Ala Pro Cys Cys Val
305                 310                 315                 320

Pro Ala Ser Tyr Asn Pro Met Val Leu Ile Gln Lys Thr Asp Thr Gly
                325                 330                 335

Val Ser Leu Gln Thr Tyr Asp Asp Leu Leu Ala Lys Asp Cys His Cys
            340                 345                 350

Ile


<210> SEQ ID NO 51
<211> LENGTH: 351
<212> TYPE: PRT
<213> ORGANISM: Artificial Sequence
<220> FEATURE:
<223> OTHER INFORMATION: Hinge deleted human IgG1-Fc(E233A, L235A)
      (T366W)-(G4S)5-GDF15 variant (delta N3, G4N, D5S, H6T)-FM2

<400> SEQUENCE: 51

Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Ser Thr Cys Pro Leu Gly Pro Gly Arg Cys Cys Arg Leu
                245                 250                 255

His Thr Val Arg Ala Ser Leu Glu Asp Leu Gly Trp Ala Asp Trp Val
            260                 265                 270

Leu Ser Pro Arg Glu Val Gln Val Thr Met Cys Ile Gly Ala Cys Pro
        275                 280                 285

Ser Gln Phe Arg Ala Ala Asn Met His Ala Gln Ile Lys Thr Ser Leu
```

```
    290                 295                 300

His Arg Leu Lys Pro Asp Thr Val Pro Ala Pro Cys Cys Val Pro Ala
305                 310                 315                 320

Ser Tyr Asn Pro Met Val Leu Ile Gln Lys Thr Asp Thr Gly Val Ser
                325                 330                 335

Leu Gln Thr Tyr Asp Asp Leu Leu Ala Lys Asp Cys His Cys Ile
            340                 345                 350


<210> SEQ ID NO 52
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
      (T366W)-(G4S)5-GDF15 variant (delta N2, R21N)-FM3

<400> SEQUENCE: 52

Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255

Leu His Thr Val Asn Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser Gln Phe Arg Ala Ala Asn Met His Ala Gln Ile Lys Thr Ser
    290                 295                 300
```

Leu His Arg Leu Lys Pro Asp Thr Val Pro Ala Pro Cys Cys Val Pro
305 310 315 320

Ala Ser Tyr Asn Pro Met Val Leu Ile Gln Lys Thr Asp Thr Gly Val
325 330 335

Ser Leu Gln Thr Tyr Asp Asp Leu Leu Ala Lys Asp Cys His Cys Ile
340 345 350

<210> SEQ ID NO 53
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
(T366W)-(G4S)5-GDF15 variant (delta N2, N56L)-FM4-3

<400> SEQUENCE: 53

Ala Pro Ala Leu Ala Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Trp Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys Gly Gly Gly Gly Ser Gly Gly
210 215 220

Gly Gly Ser Gly Gly Gly Gly Ser Gly Gly Gly Gly Ser Gly Gly Gly
225 230 235 240

Gly Ser Asn Gly Asp His Cys Pro Leu Gly Pro Gly Arg Cys Cys Arg
245 250 255

Leu His Thr Val Arg Ala Ser Leu Glu Asp Leu Gly Trp Ala Asp Trp
260 265 270

Val Leu Ser Pro Arg Glu Val Gln Val Thr Met Cys Ile Gly Ala Cys
275 280 285

Pro Ser Gln Phe Arg Ala Ala Leu Met His Ala Gln Ile Lys Thr Ser
290 295 300

Leu His Arg Leu Lys Pro Asp Thr Val Pro Ala Pro Cys Cys Val Pro
305 310 315 320

```
Ala Ser Tyr Asn Pro Met Val Leu Ile Gln Lys Thr Asp Thr Gly Val
                325                 330                 335

Ser Leu Gln Thr Tyr Asp Asp Leu Leu Ala Lys Asp Cys His Cys Ile
            340                 345                 350


<210> SEQ ID NO 54
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
      (T366W)-(G4S)5-GDF15 variant (delta N2, S64K)-FM5

<400> SEQUENCE: 54

Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255

Leu His Thr Val Arg Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser Gln Phe Arg Ala Ala Asn Met His Ala Gln Ile Lys Thr Lys
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Thr Asp Thr Gly Val
```

325 330 335

Ser Leu Gln Thr Tyr Asp Asp Leu Leu Ala Lys Asp Cys His Cys Ile
340 345 350

<210> SEQ ID NO 55
<211> LENGTH: 353
<212> TYPE: PRT
<213> ORGANISM: Artificial Sequence
<220> FEATURE:
<223> OTHER INFORMATION: Hinge deleted human IgG1-Fc(E233A, L235A)
(T366W)-(G4S)5-GDF15 variant (delta N3, WS insertion, G4N, D5S,
H6T, S64K)-FM6

<400> SEQUENCE: 55

Ala Pro Ala Leu Ala Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Trp Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys Gly Gly Gly Gly Ser Gly Gly
210 215 220

Gly Gly Ser Gly Gly Gly Gly Ser Gly Gly Gly Gly Ser Gly Gly Gly
225 230 235 240

Gly Ser Trp Ser Asn Ser Thr Cys Pro Leu Gly Pro Gly Arg Cys Cys
245 250 255

Arg Leu His Thr Val Arg Ala Ser Leu Glu Asp Leu Gly Trp Ala Asp
260 265 270

Trp Val Leu Ser Pro Arg Glu Val Gln Val Thr Met Cys Ile Gly Ala
275 280 285

Cys Pro Ser Gln Phe Arg Ala Ala Asn Met His Ala Gln Ile Lys Thr
290 295 300

Lys Leu His Arg Leu Lys Pro Asp Thr Val Pro Ala Pro Cys Cys Val
305 310 315 320

Pro Ala Ser Tyr Asn Pro Met Val Leu Ile Gln Lys Thr Asp Thr Gly
325 330 335

```
Val Ser Leu Gln Thr Tyr Asp Asp Leu Leu Ala Lys Asp Cys His Cys
            340                 345                 350

Ile


<210> SEQ ID NO 56
<211> LENGTH: 351
<212> TYPE: PRT
<213> ORGANISM: Artificial Sequence
<220> FEATURE:
<223> OTHER INFORMATION: Hinge deleted human IgG1-Fc(E233A, L235A)
      (T366W)-(G4S)5-GDF15 variant (delta N3, G4N, D5S, H6T, S64K)-FM7

<400> SEQUENCE: 56

Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Ser Thr Cys Pro Leu Gly Pro Gly Arg Cys Cys Arg Leu
                245                 250                 255

His Thr Val Arg Ala Ser Leu Glu Asp Leu Gly Trp Ala Asp Trp Val
            260                 265                 270

Leu Ser Pro Arg Glu Val Gln Val Thr Met Cys Ile Gly Ala Cys Pro
        275                 280                 285

Ser Gln Phe Arg Ala Ala Asn Met His Ala Gln Ile Lys Thr Lys Leu
    290                 295                 300

His Arg Leu Lys Pro Asp Thr Val Pro Ala Pro Cys Cys Val Pro Ala
305                 310                 315                 320

Ser Tyr Asn Pro Met Val Leu Ile Gln Lys Thr Asp Thr Gly Val Ser
                325                 330                 335
```

Leu Gln Thr Tyr Asp Asp Leu Leu Ala Lys Asp Cys His Cys Ile
340 345 350

<210> SEQ ID NO 57
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A) (T366W)-(G4S)5-GDF15 variant (delta N2, S64R)-FM9

<400> SEQUENCE: 57

Ala Pro Ala Leu Ala Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Trp Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys Gly Gly Gly Gly Ser Gly Gly
210 215 220

Gly Gly Ser Gly Gly Gly Gly Ser Gly Gly Gly Gly Ser Gly Gly Gly
225 230 235 240

Gly Ser Asn Gly Asp His Cys Pro Leu Gly Pro Gly Arg Cys Cys Arg
245 250 255

Leu His Thr Val Arg Ala Ser Leu Glu Asp Leu Gly Trp Ala Asp Trp
260 265 270

Val Leu Ser Pro Arg Glu Val Gln Val Thr Met Cys Ile Gly Ala Cys
275 280 285

Pro Ser Gln Phe Arg Ala Ala Asn Met His Ala Gln Ile Lys Thr Arg
290 295 300

Leu His Arg Leu Lys Pro Asp Thr Val Pro Ala Pro Cys Cys Val Pro
305 310 315 320

Ala Ser Tyr Asn Pro Met Val Leu Ile Gln Lys Thr Asp Thr Gly Val
325 330 335

Ser Leu Gln Thr Tyr Asp Asp Leu Leu Ala Lys Asp Cys His Cys Ile 340 345 350

<210> SEQ ID NO 58
<211> LENGTH: 353
<212> TYPE: PRT
<213> ORGANISM: Artificial Sequence
<220> FEATURE:
<223> OTHER INFORMATION: Hinge deleted human IgG1-Fc(E233A, L235A) (T366W)-(G4S)5-GDF15 variant (delta N3, WS insertion, G4N, D5S, H6T, S64R)-FM10

<400> SEQUENCE: 58

```
Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Trp Ser Asn Ser Thr Cys Pro Leu Gly Pro Gly Arg Cys Cys
                245                 250                 255

Arg Leu His Thr Val Arg Ala Ser Leu Glu Asp Leu Gly Trp Ala Asp
            260                 265                 270

Trp Val Leu Ser Pro Arg Glu Val Gln Val Thr Met Cys Ile Gly Ala
        275                 280                 285

Cys Pro Ser Gln Phe Arg Ala Ala Asn Met His Ala Gln Ile Lys Thr
    290                 295                 300

Arg Leu His Arg Leu Lys Pro Asp Thr Val Pro Ala Pro Cys Cys Val
305                 310                 315                 320

Pro Ala Ser Tyr Asn Pro Met Val Leu Ile Gln Lys Thr Asp Thr Gly
                325                 330                 335

Val Ser Leu Gln Thr Tyr Asp Asp Leu Leu Ala Lys Asp Cys His Cys
            340                 345                 350
```

Ile

<210> SEQ ID NO 59
<211> LENGTH: 351
<212> TYPE: PRT
<213> ORGANISM: Artificial Sequence
<220> FEATURE:
<223> OTHER INFORMATION: Hinge deleted human IgG1-Fc(E233A, L235A)
(T366W)-(G4S)5-GDF15 variant (delta N3, G4N, D5S, H6T, S64R)-FM11

<400> SEQUENCE: 59

Ala Pro Ala Leu Ala Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Trp Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys Gly Gly Gly Gly Ser Gly Gly
210 215 220

Gly Gly Ser Gly Gly Gly Gly Ser Gly Gly Gly Gly Ser Gly Gly Gly
225 230 235 240

Gly Ser Asn Ser Thr Cys Pro Leu Gly Pro Gly Arg Cys Cys Arg Leu
245 250 255

His Thr Val Arg Ala Ser Leu Glu Asp Leu Gly Trp Ala Asp Trp Val
260 265 270

Leu Ser Pro Arg Glu Val Gln Val Thr Met Cys Ile Gly Ala Cys Pro
275 280 285

Ser Gln Phe Arg Ala Ala Asn Met His Ala Gln Ile Lys Thr Arg Leu
290 295 300

His Arg Leu Lys Pro Asp Thr Val Pro Ala Pro Cys Cys Val Pro Ala
305 310 315 320

Ser Tyr Asn Pro Met Val Leu Ile Gln Lys Thr Asp Thr Gly Val Ser
325 330 335

Leu Gln Thr Tyr Asp Asp Leu Leu Ala Lys Asp Cys His Cys Ile
340 345 350

<210> SEQ ID NO 60
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A) (T366W)-(G4S)5-GDF15 variant (delta N2, S64N/ FM13)

<400> SEQUENCE: 60

```
Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255

Leu His Thr Val Arg Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser Gln Phe Arg Ala Ala Asn Met His Ala Gln Ile Lys Thr Asn
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Thr Asp Thr Gly Val
                325                 330                 335

Ser Leu Gln Thr Tyr Asp Asp Leu Leu Ala Lys Asp Cys His Cys Ile
            340                 345                 350
```

<210> SEQ ID NO 61
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
(T366W)-(G4S)5-GDF15 variant (delta N2,S64D)-FM14

<400> SEQUENCE: 61

```
Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255

Leu His Thr Val Arg Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser Gln Phe Arg Ala Ala Asn Met His Ala Gln Ile Lys Thr Asp
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Thr Asp Thr Gly Val
                325                 330                 335

Ser Leu Gln Thr Tyr Asp Asp Leu Leu Ala Lys Asp Cys His Cys Ile
            340                 345                 350
```

<210> SEQ ID NO 62
<211> LENGTH: 352

<212> TYPE: PRT
<213> ORGANISM: Artificial Sequence
<220> FEATURE:
<223> OTHER INFORMATION: Hinge deleted human IgG1-Fc(E233A, L235A)
(T366W)-(G4S)5-GDF15 variant (delta N2,S64E)-FM15

<400> SEQUENCE: 62

```
Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255

Leu His Thr Val Arg Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser Gln Phe Arg Ala Ala Asn Met His Ala Gln Ile Lys Thr Glu
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Thr Asp Thr Gly Val
                325                 330                 335

Ser Leu Gln Thr Tyr Asp Asp Leu Leu Ala Lys Asp Cys His Cys Ile
            340                 345                 350
```

<210> SEQ ID NO 63
<211> LENGTH: 352
<212> TYPE: PRT
<213> ORGANISM: Artificial Sequence

```
<220> FEATURE:
<223> OTHER INFORMATION: Hinge deleted human IgG1-Fc(E233A, L235A)
      (T366W)-(G4S)5-GDF15 variant (delta N2,S64L)-FM16

<400> SEQUENCE: 63

Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255

Leu His Thr Val Arg Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser Gln Phe Arg Ala Ala Asn Met His Ala Gln Ile Lys Thr Leu
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Thr Asp Thr Gly Val
                325                 330                 335

Ser Leu Gln Thr Tyr Asp Asp Leu Leu Ala Lys Asp Cys His Cys Ile
            340                 345                 350


<210> SEQ ID NO 64
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
```

(T366W)-(G4S)5-GDF15 variant (delta N2, D103L)-FM4-2

<400> SEQUENCE: 64

```
Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255

Leu His Thr Val Arg Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser Gln Phe Arg Ala Ala Asn Met His Ala Gln Ile Lys Thr Ser
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Thr Asp Thr Gly Val
                325                 330                 335

Ser Leu Gln Thr Tyr Asp Leu Leu Leu Ala Lys Asp Cys His Cys Ile
            340                 345                 350
```

<210> SEQ ID NO 65
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
(T366W)-(G4S)5-GDF15 variant (delta N2, N56C, D103C)-FM4

<400> SEQUENCE: 65

Ala Pro Ala Leu Ala Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Trp Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys Gly Gly Gly Gly Ser Gly Gly
210 215 220

Gly Gly Ser Gly Gly Gly Gly Ser Gly Gly Gly Gly Ser Gly Gly Gly
225 230 235 240

Gly Ser Asn Gly Asp His Cys Pro Leu Gly Pro Gly Arg Cys Cys Arg
245 250 255

Leu His Thr Val Arg Ala Ser Leu Glu Asp Leu Gly Trp Ala Asp Trp
260 265 270

Val Leu Ser Pro Arg Glu Val Gln Val Thr Met Cys Ile Gly Ala Cys
275 280 285

Pro Ser Gln Phe Arg Ala Ala Cys Met His Ala Gln Ile Lys Thr Ser
290 295 300

Leu His Arg Leu Lys Pro Asp Thr Val Pro Ala Pro Cys Cys Val Pro
305 310 315 320

Ala Ser Tyr Asn Pro Met Val Leu Ile Gln Lys Thr Asp Thr Gly Val
325 330 335

Ser Leu Gln Thr Tyr Asp Cys Leu Leu Ala Lys Asp Cys His Cys Ile
340 345 350

<210> SEQ ID NO 66
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
(T366W)-(G4S)5-GDF15 variant (delta N2, N56S, D103S)-FM4-1

<400> SEQUENCE: 66

```
Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255

Leu His Thr Val Arg Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser Gln Phe Arg Ala Ala Ser Met His Ala Gln Ile Lys Thr Ser
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Thr Asp Thr Gly Val
                325                 330                 335

Ser Leu Gln Thr Tyr Asp Ser Leu Leu Ala Lys Asp Cys His Cys Ile
            340                 345                 350
```

<210> SEQ ID NO 67
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A) (T366W)-(G4S)5-GDF15 variant (delta N2, R21N, S64K)-FM8

<400> SEQUENCE: 67

```
Ala Pro Ala Leu Ala Gly Gly Pro Ser Val Phe Leu Phe Pro Pro Lys
1               5                   10                  15
```

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Trp Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys Gly Gly Gly Gly Ser Gly Gly
210 215 220

Gly Gly Ser Gly Gly Gly Gly Ser Gly Gly Gly Gly Ser Gly Gly Gly
225 230 235 240

Gly Ser Asn Gly Asp His Cys Pro Leu Gly Pro Gly Arg Cys Cys Arg
245 250 255

Leu His Thr Val Asn Ala Ser Leu Glu Asp Leu Gly Trp Ala Asp Trp
260 265 270

Val Leu Ser Pro Arg Glu Val Gln Val Thr Met Cys Ile Gly Ala Cys
275 280 285

Pro Ser Gln Phe Arg Ala Ala Asn Met His Ala Gln Ile Lys Thr Lys
290 295 300

Leu His Arg Leu Lys Pro Asp Thr Val Pro Ala Pro Cys Cys Val Pro
305 310 315 320

Ala Ser Tyr Asn Pro Met Val Leu Ile Gln Lys Thr Asp Thr Gly Val
325 330 335

Ser Leu Gln Thr Tyr Asp Asp Leu Leu Ala Lys Asp Cys His Cys Ile
340 345 350

<210> SEQ ID NO 68
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
(T366W)-(G4S)5-GDF15 variant (delta N2, R21N, S64R)-FM12

<400> SEQUENCE: 68

Ala Pro Ala Leu Ala Gly Gly Pro Ser Val Phe Leu Phe Pro Pro Lys
1 5 10 15

Pro Lys Asp Thr Leu Met Ile Ser Arg Thr Pro Glu Val Thr Cys Val

```
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255

Leu His Thr Val Asn Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser Gln Phe Arg Ala Ala Asn Met His Ala Gln Ile Lys Thr Arg
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Thr Asp Thr Gly Val
                325                 330                 335

Ser Leu Gln Thr Tyr Asp Asp Leu Leu Ala Lys Asp Cys His Cys Ile
            340                 345                 350
```

<210> SEQ ID NO 69
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A) (T366W)-(G4S)5-GDF15 variant (delta N2, W32F)

<400> SEQUENCE: 69

```
Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30
```

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Trp Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys Gly Gly Gly Gly Ser Gly Gly
210 215 220

Gly Gly Ser Gly Gly Gly Gly Ser Gly Gly Gly Gly Ser Gly Gly Gly
225 230 235 240

Gly Ser Asn Gly Asp His Cys Pro Leu Gly Pro Gly Arg Cys Cys Arg
245 250 255

Leu His Thr Val Arg Ala Ser Leu Glu Asp Leu Gly Trp Ala Asp Phe
260 265 270

Val Leu Ser Pro Arg Glu Val Gln Val Thr Met Cys Ile Gly Ala Cys
275 280 285

Pro Ser Gln Phe Arg Ala Ala Asn Met His Ala Gln Ile Lys Thr Ser
290 295 300

Leu His Arg Leu Lys Pro Asp Thr Val Pro Ala Pro Cys Cys Val Pro
305 310 315 320

Ala Ser Tyr Asn Pro Met Val Leu Ile Gln Lys Thr Asp Thr Gly Val
325 330 335

Ser Leu Gln Thr Tyr Asp Asp Leu Leu Ala Lys Asp Cys His Cys Ile
340 345 350

<210> SEQ ID NO 70
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A) (T366W)-(G4S)5-GDF15 variant (delta N2, W32H)

<400> SEQUENCE: 70

Ala Pro Ala Leu Ala Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Trp Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys Gly Gly Gly Gly Ser Gly Gly
210 215 220

Gly Gly Ser Gly Gly Gly Gly Ser Gly Gly Gly Gly Ser Gly Gly Gly
225 230 235 240

Gly Ser Asn Gly Asp His Cys Pro Leu Gly Pro Gly Arg Cys Cys Arg
245 250 255

Leu His Thr Val Arg Ala Ser Leu Glu Asp Leu Gly Trp Ala Asp His
260 265 270

Val Leu Ser Pro Arg Glu Val Gln Val Thr Met Cys Ile Gly Ala Cys
275 280 285

Pro Ser Gln Phe Arg Ala Ala Asn Met His Ala Gln Ile Lys Thr Ser
290 295 300

Leu His Arg Leu Lys Pro Asp Thr Val Pro Ala Pro Cys Cys Val Pro
305 310 315 320

Ala Ser Tyr Asn Pro Met Val Leu Ile Gln Lys Thr Asp Thr Gly Val
325 330 335

Ser Leu Gln Thr Tyr Asp Asp Leu Leu Ala Lys Asp Cys His Cys Ile
340 345 350

<210> SEQ ID NO 71
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A) (T366W)-(G4S)5-GDF15 variant (delta N2, W32Y)

<400> SEQUENCE: 71

Ala Pro Ala Leu Ala Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu

```
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255

Leu His Thr Val Arg Ala Ser Leu Glu Asp Leu Gly Trp Ala Asp Tyr
            260                 265                 270

Val Leu Ser Pro Arg Glu Val Gln Val Thr Met Cys Ile Gly Ala Cys
        275                 280                 285

Pro Ser Gln Phe Arg Ala Ala Asn Met His Ala Gln Ile Lys Thr Ser
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Thr Asp Thr Gly Val
                325                 330                 335

Ser Leu Gln Thr Tyr Asp Asp Leu Leu Ala Lys Asp Cys His Cys Ile
            340                 345                 350


<210> SEQ ID NO 72
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
      (T366W)-(G4S)5-GDF15 variant (delta N2, Q51H)

<400> SEQUENCE: 72

Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60
```

-continued

```
Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255

Leu His Thr Val Arg Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser His Phe Arg Ala Ala Asn Met His Ala Gln Ile Lys Thr Ser
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Thr Asp Thr Gly Val
                325                 330                 335

Ser Leu Gln Thr Tyr Asp Asp Leu Leu Ala Lys Asp Cys His Cys Ile
            340                 345                 350


<210> SEQ ID NO 73
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
      (T366W)-(G4S)5-GDF15 variant (delta N2, Q51L)

<400> SEQUENCE: 73

Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80
```

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Trp Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys Gly Gly Gly Gly Ser Gly Gly
210 215 220

Gly Gly Ser Gly Gly Gly Gly Ser Gly Gly Gly Gly Ser Gly Gly Gly
225 230 235 240

Gly Ser Asn Gly Asp His Cys Pro Leu Gly Pro Gly Arg Cys Cys Arg
245 250 255

Leu His Thr Val Arg Ala Ser Leu Glu Asp Leu Gly Trp Ala Asp Trp
260 265 270

Val Leu Ser Pro Arg Glu Val Gln Val Thr Met Cys Ile Gly Ala Cys
275 280 285

Pro Ser Leu Phe Arg Ala Ala Asn Met His Ala Gln Ile Lys Thr Ser
290 295 300

Leu His Arg Leu Lys Pro Asp Thr Val Pro Ala Pro Cys Cys Val Pro
305 310 315 320

Ala Ser Tyr Asn Pro Met Val Leu Ile Gln Lys Thr Asp Thr Gly Val
325 330 335

Ser Leu Gln Thr Tyr Asp Asp Leu Leu Ala Lys Asp Cys His Cys Ile
340 345 350

<210> SEQ ID NO 74
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
(T366W)-(G4S)5-GDF15 variant (delta N2, Q51E)

<400> SEQUENCE: 74

Ala Pro Ala Leu Ala Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys

```
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255

Leu His Thr Val Arg Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser Glu Phe Arg Ala Ala Asn Met His Ala Gln Ile Lys Thr Ser
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Thr Asp Thr Gly Val
                325                 330                 335

Ser Leu Gln Thr Tyr Asp Asp Leu Leu Ala Lys Asp Cys His Cys Ile
            340                 345                 350


<210> SEQ ID NO 75
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
      (T366W)-(G4S)5-GDF15 variant (delta N2, Q51N)

<400> SEQUENCE: 75

Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95
```

```
Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255

Leu His Thr Val Arg Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser Asn Phe Arg Ala Ala Asn Met His Ala Gln Ile Lys Thr Ser
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Thr Asp Thr Gly Val
                325                 330                 335

Ser Leu Gln Thr Tyr Asp Asp Leu Leu Ala Lys Asp Cys His Cys Ile
            340                 345                 350
```

<210> SEQ ID NO 76
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A) (T366W)-(G4S)5-GDF15 variant (delta N2, Q90H)

<400> SEQUENCE: 76

```
Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110
```

```
Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255

Leu His Thr Val Arg Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser Gln Phe Arg Ala Ala Asn Met His Ala Gln Ile Lys Thr Ser
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile His Lys Thr Asp Thr Gly Val
                325                 330                 335

Ser Leu Gln Thr Tyr Asp Asp Leu Leu Ala Lys Asp Cys His Cys Ile
            340                 345                 350


<210> SEQ ID NO 77
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
      (T366W)-(G4S)5-GDF15 variant (delta N2, Q90E)

<400> SEQUENCE: 77

Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
```

```
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255

Leu His Thr Val Arg Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser Gln Phe Arg Ala Ala Asn Met His Ala Gln Ile Lys Thr Ser
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Glu Lys Thr Asp Thr Gly Val
                325                 330                 335

Ser Leu Gln Thr Tyr Asp Asp Leu Leu Ala Lys Asp Cys His Cys Ile
            340                 345                 350


<210> SEQ ID NO 78
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
      (T366W)-(G4S)5-GDF15 variant (delta N2, Q90K)

<400> SEQUENCE: 78

Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125
```

Thr Lys Asn Gln Val Ser Leu Trp Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys Gly Gly Gly Gly Ser Gly Gly
210 215 220

Gly Gly Ser Gly Gly Gly Gly Ser Gly Gly Gly Gly Ser Gly Gly Gly
225 230 235 240

Gly Ser Asn Gly Asp His Cys Pro Leu Gly Pro Gly Arg Cys Cys Arg
245 250 255

Leu His Thr Val Arg Ala Ser Leu Glu Asp Leu Gly Trp Ala Asp Trp
260 265 270

Val Leu Ser Pro Arg Glu Val Gln Val Thr Met Cys Ile Gly Ala Cys
275 280 285

Pro Ser Gln Phe Arg Ala Ala Asn Met His Ala Gln Ile Lys Thr Ser
290 295 300

Leu His Arg Leu Lys Pro Asp Thr Val Pro Ala Pro Cys Cys Val Pro
305 310 315 320

Ala Ser Tyr Asn Pro Met Val Leu Ile Lys Lys Thr Asp Thr Gly Val
325 330 335

Ser Leu Gln Thr Tyr Asp Asp Leu Leu Ala Lys Asp Cys His Cys Ile
340 345 350

<210> SEQ ID NO 79
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A) (T366W)-(G4S)5-GDF15 variant (delta N2, D93E)

<400> SEQUENCE: 79

Ala Pro Ala Leu Ala Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Trp Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys Gly Gly Gly Gly Ser Gly Gly
210 215 220

Gly Gly Ser Gly Gly Gly Gly Ser Gly Gly Gly Gly Ser Gly Gly Gly
225 230 235 240

Gly Ser Asn Gly Asp His Cys Pro Leu Gly Pro Gly Arg Cys Cys Arg
245 250 255

Leu His Thr Val Arg Ala Ser Leu Glu Asp Leu Gly Trp Ala Asp Trp
260 265 270

Val Leu Ser Pro Arg Glu Val Gln Val Thr Met Cys Ile Gly Ala Cys
275 280 285

Pro Ser Gln Phe Arg Ala Ala Asn Met His Ala Gln Ile Lys Thr Ser
290 295 300

Leu His Arg Leu Lys Pro Asp Thr Val Pro Ala Pro Cys Cys Val Pro
305 310 315 320

Ala Ser Tyr Asn Pro Met Val Leu Ile Gln Lys Thr Glu Thr Gly Val
325 330 335

Ser Leu Gln Thr Tyr Asp Asp Leu Leu Ala Lys Asp Cys His Cys Ile
340 345 350

<210> SEQ ID NO 80
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
(T366W)-(G4S)5-GDF15 variant (delta N2, D93L)

<400> SEQUENCE: 80

Ala Pro Ala Leu Ala Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Trp Cys Leu Val Lys Gly Phe Tyr Pro
130 135 140

Ser Asp Ile Ala Val Glu Trp Glu Ser Asn Gly Gln Pro Glu Asn Asn

```
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255

Leu His Thr Val Arg Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser Gln Phe Arg Ala Ala Asn Met His Ala Gln Ile Lys Thr Ser
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Thr Leu Thr Gly Val
                325                 330                 335

Ser Leu Gln Thr Tyr Asp Asp Leu Leu Ala Lys Asp Cys His Cys Ile
            340                 345                 350


<210> SEQ ID NO 81
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
      (T366W)-(G4S)5-GDF15 variant (delta N2, D93N)

<400> SEQUENCE: 81

Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160
```

-continued

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys Gly Gly Gly Gly Ser Gly Gly
210 215 220

Gly Gly Ser Gly Gly Gly Gly Ser Gly Gly Gly Gly Ser Gly Gly Gly
225 230 235 240

Gly Ser Asn Gly Asp His Cys Pro Leu Gly Pro Gly Arg Cys Cys Arg
245 250 255

Leu His Thr Val Arg Ala Ser Leu Glu Asp Leu Gly Trp Ala Asp Trp
260 265 270

Val Leu Ser Pro Arg Glu Val Gln Val Thr Met Cys Ile Gly Ala Cys
275 280 285

Pro Ser Gln Phe Arg Ala Ala Asn Met His Ala Gln Ile Lys Thr Ser
290 295 300

Leu His Arg Leu Lys Pro Asp Thr Val Pro Ala Pro Cys Cys Val Pro
305 310 315 320

Ala Ser Tyr Asn Pro Met Val Leu Ile Gln Lys Thr Asn Thr Gly Val
325 330 335

Ser Leu Gln Thr Tyr Asp Asp Leu Leu Ala Lys Asp Cys His Cys Ile
340 345 350

<210> SEQ ID NO 82
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
(T366W)-(G4S)5-GDF15 variant (delta N2, D93Q)

<400> SEQUENCE: 82

Ala Pro Ala Leu Ala Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Trp Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

```
Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255

Leu His Thr Val Arg Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser Gln Phe Arg Ala Ala Asn Met His Ala Gln Ile Lys Thr Ser
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Thr Gln Thr Gly Val
                325                 330                 335

Ser Leu Gln Thr Tyr Asp Asp Leu Leu Ala Lys Asp Cys His Cys Ile
            340                 345                 350


<210> SEQ ID NO 83
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
      (T366W)-(G4S)5-GDF15 variant (delta N2, Q60L)

<400> SEQUENCE: 83

Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
```

```
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255

Leu His Thr Val Arg Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser Gln Phe Arg Ala Ala Asn Met His Ala Leu Ile Lys Thr Ser
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Thr Asp Thr Gly Val
                325                 330                 335

Ser Leu Gln Thr Tyr Asp Asp Leu Leu Ala Lys Asp Cys His Cys Ile
            340                 345                 350


<210> SEQ ID NO 84
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
      (T366W)-(G4S)5-GDF15 variant (delta N2,Q60N)

<400> SEQUENCE: 84

Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190
```

```
Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255

Leu His Thr Val Arg Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser Gln Phe Arg Ala Ala Asn Met His Ala Asn Ile Lys Thr Ser
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Thr Asp Thr Gly Val
                325                 330                 335

Ser Leu Gln Thr Tyr Asp Asp Leu Leu Ala Lys Asp Cys His Cys Ile
            340                 345                 350
```

<210> SEQ ID NO 85
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A) (T366W)-(G4S)5-GDF15 variant (delta N2, S64Q)

<400> SEQUENCE: 85

```
Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205
```

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255

Leu His Thr Val Arg Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser Gln Phe Arg Ala Ala Asn Met His Ala Gln Ile Lys Thr Gln
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Thr Asp Thr Gly Val
                325                 330                 335

Ser Leu Gln Thr Tyr Asp Asp Leu Leu Ala Lys Asp Cys His Cys Ile
            340                 345                 350

<210> SEQ ID NO 86
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A) (T366W)-(G4S)5-GDF15 variant (delta N2, T92S)

<400> SEQUENCE: 86

Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly

```
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255

Leu His Thr Val Arg Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser Gln Phe Arg Ala Ala Asn Met His Ala Gln Ile Lys Thr Ser
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Ser Asp Thr Gly Val
                325                 330                 335

Ser Leu Gln Thr Tyr Asp Asp Leu Leu Ala Lys Asp Cys His Cys Ile
            340                 345                 350


<210> SEQ ID NO 87
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
      (T366W)-(G4S)5-GDF15 variant (delta N2, T92E)

<400> SEQUENCE: 87

Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220
```

Gly Gly Ser Gly Gly Gly Gly Ser Gly Gly Gly Gly Ser Gly Gly Gly
225 230 235 240

Gly Ser Asn Gly Asp His Cys Pro Leu Gly Pro Gly Arg Cys Cys Arg
245 250 255

Leu His Thr Val Arg Ala Ser Leu Glu Asp Leu Gly Trp Ala Asp Trp
260 265 270

Val Leu Ser Pro Arg Glu Val Gln Val Thr Met Cys Ile Gly Ala Cys
275 280 285

Pro Ser Gln Phe Arg Ala Ala Asn Met His Ala Gln Ile Lys Thr Ser
290 295 300

Leu His Arg Leu Lys Pro Asp Thr Val Pro Ala Pro Cys Cys Val Pro
305 310 315 320

Ala Ser Tyr Asn Pro Met Val Leu Ile Gln Lys Glu Asp Thr Gly Val
325 330 335

Ser Leu Gln Thr Tyr Asp Asp Leu Leu Ala Lys Asp Cys His Cys Ile
340 345 350

<210> SEQ ID NO 88
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
(T366W)-(G4S)5-GDF15 variant (delta N2, S97N)

<400> SEQUENCE: 88

Ala Pro Ala Leu Ala Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Trp Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys Gly Gly Gly Gly Ser Gly Gly
210 215 220

Gly Gly Ser Gly Gly Gly Gly Ser Gly Gly Gly Gly Ser Gly Gly Gly
225 230 235 240

```
Gly Ser Asn Gly Asp His Cys Pro Leu Gly Pro Gly Arg Cys Cys Arg
                245                 250                 255

Leu His Thr Val Arg Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser Gln Phe Arg Ala Ala Asn Met His Ala Gln Ile Lys Thr Ser
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Thr Asp Thr Gly Val
                325                 330                 335

Asn Leu Gln Thr Tyr Asp Asp Leu Leu Ala Lys Asp Cys His Cys Ile
            340                 345                 350


<210> SEQ ID NO 89
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
      (T366W)-(G4S)5-GDF15 variant (delta N2, S97Q)

<400> SEQUENCE: 89

Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Ser Gly Gly Gly
225                 230                 235                 240

Gly Ser Asn Gly Asp His Cys Pro Leu Gly Pro Gly Arg Cys Cys Arg
```

```
                245                 250                 255

Leu His Thr Val Arg Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser Gln Phe Arg Ala Ala Asn Met His Ala Gln Ile Lys Thr Ser
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Thr Asp Thr Gly Val
                325                 330                 335

Gln Leu Gln Thr Tyr Asp Asp Leu Leu Ala Lys Asp Cys His Cys Ile
            340                 345                 350


<210> SEQ ID NO 90
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A)
      (T366W)-(G4S)5-GDF15 variant (delta N2,Y101F)

<400> SEQUENCE: 90

Ala Pro Ala Leu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Asn Gly Asp His Cys Pro Leu Gly Pro Gly Arg Cys Cys Arg
                245                 250                 255
```

Leu His Thr Val Arg Ala Ser Leu Glu Asp Leu Gly Trp Ala Asp Trp
260 265 270

Val Leu Ser Pro Arg Glu Val Gln Val Thr Met Cys Ile Gly Ala Cys
275 280 285

Pro Ser Gln Phe Arg Ala Ala Asn Met His Ala Gln Ile Lys Thr Ser
290 295 300

Leu His Arg Leu Lys Pro Asp Thr Val Pro Ala Pro Cys Cys Val Pro
305 310 315 320

Ala Ser Tyr Asn Pro Met Val Leu Ile Gln Lys Thr Asp Thr Gly Val
325 330 335

Ser Leu Gln Thr Phe Asp Asp Leu Leu Ala Lys Asp Cys His Cys Ile
340 345 350

<210> SEQ ID NO 91
<211> LENGTH: 352
<212> TYPE: PRT
<213> ORGANISM: Artificial Sequence
<220> FEATURE:
<223> OTHER INFORMATION: Hinge deleted human IgG1-Fc(E233A, L235A) (T366W)-(G4S)5-GDF15 variant (delta N2, Y101Q)

<400> SEQUENCE: 91

Ala Pro Ala Leu Ala Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Trp Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys Gly Gly Gly Gly Ser Gly Gly
210 215 220

Gly Gly Ser Gly Gly Gly Gly Ser Gly Gly Gly Gly Ser Gly Gly Gly
225 230 235 240

Gly Ser Asn Gly Asp His Cys Pro Leu Gly Pro Gly Arg Cys Cys Arg
245 250 255

Leu His Thr Val Arg Ala Ser Leu Glu Asp Leu Gly Trp Ala Asp Trp
260 265 270

Val Leu Ser Pro Arg Glu Val Gln Val Thr Met Cys Ile Gly Ala Cys
        275                 280                 285

Pro Ser Gln Phe Arg Ala Ala Asn Met His Ala Gln Ile Lys Thr Ser
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Thr Asp Thr Gly Val
                325                 330                 335

Ser Leu Gln Thr Gln Asp Asp Leu Leu Ala Lys Asp Cys His Cys Ile
            340                 345                 350

<210> SEQ ID NO 92
<211> LENGTH: 17
<212> TYPE: PRT
<213> ORGANISM: Artificial Sequence
<220> FEATURE:
<223> OTHER INFORMATION: linker-GS(G4S)3

<400> SEQUENCE: 92

Gly Ser Gly Gly Gly Gly Ser Gly Gly Gly Gly Ser Gly Gly Gly Gly
1               5                   10                  15

Ser

<210> SEQ ID NO 93
<211> LENGTH: 27
<212> TYPE: PRT
<213> ORGANISM: Artificial Sequence
<220> FEATURE:
<223> OTHER INFORMATION: linker-GS(G4S)5

<400> SEQUENCE: 93

Gly Ser Gly Gly Gly Gly Ser Gly Gly Gly Gly Ser Gly Gly Gly Gly
1               5                   10                  15

Ser Gly Gly Gly Gly Ser Gly Gly Gly Gly Ser
            20                  25

<210> SEQ ID NO 94
<211> LENGTH: 37
<212> TYPE: PRT
<213> ORGANISM: Artificial Sequence
<220> FEATURE:
<223> OTHER INFORMATION: linker-GS(G4S)7

<400> SEQUENCE: 94

Gly Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser
        35

<210> SEQ ID NO 95
<211> LENGTH: 26
<212> TYPE: PRT
<213> ORGANISM: Artificial Sequence
<220> FEATURE:
<223> OTHER INFORMATION: linker-GS(EEEA)6

<400> SEQUENCE: 95

Gly Ser Glu Glu Glu Ala Glu Glu Glu Ala Glu Glu Glu Ala Glu Glu
1               5                   10                  15

Glu Ala Glu Glu Glu Ala Glu Glu Glu Ala
20 25

<210> SEQ ID NO 96
<211> LENGTH: 26
<212> TYPE: PRT
<213> ORGANISM: Artificial Sequence
<220> FEATURE:
<223> OTHER INFORMATION: linker-GSGGSS(PT)10

<400> SEQUENCE: 96

Gly Ser Gly Gly Ser Ser Pro Thr Pro Thr Pro Thr Pro Thr Pro Thr
1 5 10 15

Pro Thr Pro Thr Pro Thr Pro Thr Pro Thr
20 25

<210> SEQ ID NO 97
<211> LENGTH: 27
<212> TYPE: PRT
<213> ORGANISM: Artificial Sequence
<220> FEATURE:
<223> OTHER INFORMATION: linker-GS(EAAAK)5

<400> SEQUENCE: 97

Gly Ser Glu Ala Ala Ala Lys Glu Ala Ala Ala Lys Glu Ala Ala Ala
1 5 10 15

Lys Glu Ala Ala Ala Lys Glu Ala Ala Ala Lys
20 25

<210> SEQ ID NO 98
<211> LENGTH: 344
<212> TYPE: PRT
<213> ORGANISM: Artificial Sequence
<220> FEATURE:
<223> OTHER INFORMATION: Hinge deleted human IgG1-Fc(L234A, L235A, N297A)(T366W)-GS(G4S)3-GDF15 variant (delta N2, S64R / FM9-1)

<400> SEQUENCE: 98

Ala Pro Glu Ala Ala Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Ala Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Trp Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

```
Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Ser Gly Gly Gly Gly Ser
    210                 215                 220

Gly Gly Gly Gly Ser Gly Gly Gly Gly Ser Asn Gly Asp His Cys Pro
225                 230                 235                 240

Leu Gly Pro Gly Arg Cys Cys Arg Leu His Thr Val Arg Ala Ser Leu
                245                 250                 255

Glu Asp Leu Gly Trp Ala Asp Trp Val Leu Ser Pro Arg Glu Val Gln
            260                 265                 270

Val Thr Met Cys Ile Gly Ala Cys Pro Ser Gln Phe Arg Ala Ala Asn
        275                 280                 285

Met His Ala Gln Ile Lys Thr Arg Leu His Arg Leu Lys Pro Asp Thr
    290                 295                 300

Val Pro Ala Pro Cys Cys Val Pro Ala Ser Tyr Asn Pro Met Val Leu
305                 310                 315                 320

Ile Gln Lys Thr Asp Thr Gly Val Ser Leu Gln Thr Tyr Asp Asp Leu
                325                 330                 335

Leu Ala Lys Asp Cys His Cys Ile
            340


<210> SEQ ID NO 99
<211> LENGTH: 354
<212> TYPE: PRT
<213> ORGANISM: Artificial Sequence
<220> FEATURE:
<223> OTHER INFORMATION: Hinge deleted human IgG1-Fc(L234A, L235A,
      N297A)(T366W)-GS(G4S)5-GDF15 variant (delta N2, S64R / FM9-2)

<400> SEQUENCE: 99

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Ala Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190
```

```
Phe Ser Cys Ser Val Met His Glu Ala Leu His Asn His Tyr Thr Gln
        195                 200                 205

Lys Ser Leu Ser Leu Ser Pro Gly Lys Gly Ser Gly Gly Gly Gly Ser
    210                 215                 220

Gly Gly Gly Gly Ser Gly Gly Gly Gly Ser Gly Gly Gly Gly Ser Gly
225                 230                 235                 240

Gly Gly Gly Ser Asn Gly Asp His Cys Pro Leu Gly Pro Gly Arg Cys
                245                 250                 255

Cys Arg Leu His Thr Val Arg Ala Ser Leu Glu Asp Leu Gly Trp Ala
            260                 265                 270

Asp Trp Val Leu Ser Pro Arg Glu Val Gln Val Thr Met Cys Ile Gly
        275                 280                 285

Ala Cys Pro Ser Gln Phe Arg Ala Ala Asn Met His Ala Gln Ile Lys
    290                 295                 300

Thr Arg Leu His Arg Leu Lys Pro Asp Thr Val Pro Ala Pro Cys Cys
305                 310                 315                 320

Val Pro Ala Ser Tyr Asn Pro Met Val Leu Ile Gln Lys Thr Asp Thr
                325                 330                 335

Gly Val Ser Leu Gln Thr Tyr Asp Asp Leu Leu Ala Lys Asp Cys His
            340                 345                 350

Cys Ile


<210> SEQ ID NO 100
<211> LENGTH: 364
<212> TYPE: PRT
<213> ORGANISM: Artificial Sequence
<220> FEATURE:
<223> OTHER INFORMATION: Hinge deleted human IgG1-Fc(L234A, L235A,
      N297A)(T366W)-GS(G4S)7-GDF15 variant (delta N2, S64R / FM9-3)

<400> SEQUENCE: 100

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Ala Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190
```

Phe Ser Cys Ser Val Met His Glu Ala Leu His Asn His Tyr Thr Gln
195 200 205

Lys Ser Leu Ser Leu Ser Pro Gly Lys Gly Ser Gly Gly Gly Gly Ser
210 215 220

Gly Gly Gly Gly Ser Gly Gly Gly Gly Ser Gly Gly Gly Gly Ser Gly
225 230 235 240

Gly Gly Gly Ser Gly Gly Gly Gly Ser Gly Gly Gly Gly Ser Asn Gly
245 250 255

Asp His Cys Pro Leu Gly Pro Gly Arg Cys Cys Arg Leu His Thr Val
260 265 270

Arg Ala Ser Leu Glu Asp Leu Gly Trp Ala Asp Trp Val Leu Ser Pro
275 280 285

Arg Glu Val Gln Val Thr Met Cys Ile Gly Ala Cys Pro Ser Gln Phe
290 295 300

Arg Ala Ala Asn Met His Ala Gln Ile Lys Thr Arg Leu His Arg Leu
305 310 315 320

Lys Pro Asp Thr Val Pro Ala Pro Cys Cys Val Pro Ala Ser Tyr Asn
325 330 335

Pro Met Val Leu Ile Gln Lys Thr Asp Thr Gly Val Ser Leu Gln Thr
340 345 350

Tyr Asp Asp Leu Leu Ala Lys Asp Cys His Cys Ile
355 360

<210> SEQ ID NO 101
<211> LENGTH: 353
<212> TYPE: PRT
<213> ORGANISM: Artificial Sequence
<220> FEATURE:
<223> OTHER INFORMATION: Hinge deleted human IgG1-Fc(L234A, L235A, N297A)(T366W)-GS(EEEA)6-GDF15 variant (delta N2, S64R / FM9-4)

<400> SEQUENCE: 101

Ala Pro Glu Ala Ala Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Ala Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Trp Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val

```
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Ser Glu Glu Glu Ala Glu
    210                 215                 220

Glu Glu Ala Glu Glu Glu Ala Glu Glu Glu Ala Glu Glu Glu Ala Glu
225                 230                 235                 240

Glu Glu Ala Asn Gly Asp His Cys Pro Leu Gly Pro Gly Arg Cys Cys
                245                 250                 255

Arg Leu His Thr Val Arg Ala Ser Leu Glu Asp Leu Gly Trp Ala Asp
            260                 265                 270

Trp Val Leu Ser Pro Arg Glu Val Gln Val Thr Met Cys Ile Gly Ala
        275                 280                 285

Cys Pro Ser Gln Phe Arg Ala Ala Asn Met His Ala Gln Ile Lys Thr
    290                 295                 300

Arg Leu His Arg Leu Lys Pro Asp Thr Val Pro Ala Pro Cys Cys Val
305                 310                 315                 320

Pro Ala Ser Tyr Asn Pro Met Val Leu Ile Gln Lys Thr Asp Thr Gly
                325                 330                 335

Val Ser Leu Gln Thr Tyr Asp Asp Leu Leu Ala Lys Asp Cys His Cys
            340                 345                 350

Ile


<210> SEQ ID NO 102
<211> LENGTH: 353
<212> TYPE: PRT
<213> ORGANISM: Artificial Sequence
<220> FEATURE:
<223> OTHER INFORMATION: Hinge deleted human IgG1-Fc(L234A, L235A,
      N297A)(T366W)-GSGGSS(PT)10-GDF15 variant (delta N2, S64R / FM9-5)

<400> SEQUENCE: 102

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Ala Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
```

```
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Ser Gly Gly Ser Ser Pro
    210                 215                 220

Thr Pro Thr Pro Thr Pro Thr Pro Thr Pro Thr Pro Thr Pro Thr Pro
225                 230                 235                 240

Thr Pro Thr Asn Gly Asp His Cys Pro Leu Gly Pro Gly Arg Cys Cys
                245                 250                 255

Arg Leu His Thr Val Arg Ala Ser Leu Glu Asp Leu Gly Trp Ala Asp
            260                 265                 270

Trp Val Leu Ser Pro Arg Glu Val Gln Val Thr Met Cys Ile Gly Ala
        275                 280                 285

Cys Pro Ser Gln Phe Arg Ala Ala Asn Met His Ala Gln Ile Lys Thr
    290                 295                 300

Arg Leu His Arg Leu Lys Pro Asp Thr Val Pro Ala Pro Cys Cys Val
305                 310                 315                 320

Pro Ala Ser Tyr Asn Pro Met Val Leu Ile Gln Lys Thr Asp Thr Gly
                325                 330                 335

Val Ser Leu Gln Thr Tyr Asp Asp Leu Leu Ala Lys Asp Cys His Cys
            340                 345                 350

Ile
```

<210> SEQ ID NO 103
<211> LENGTH: 354
<212> TYPE: PRT
<213> ORGANISM: Artificial Sequence
<220> FEATURE:
<223> OTHER INFORMATION: Hinge deleted human IgG1-Fc(L234A, L235A, N297A)(T366W)-GS(EAAAK)5-GDF15 variant (delta N2, S64R / FM9-6)

<400> SEQUENCE: 103

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Ala Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
```

```
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Ser Glu Ala Ala Ala Lys
    210                 215                 220

Glu Ala Ala Ala Lys Glu Ala Ala Ala Lys Glu Ala Ala Ala Lys Glu
225                 230                 235                 240

Ala Ala Ala Lys Asn Gly Asp His Cys Pro Leu Gly Pro Gly Arg Cys
                245                 250                 255

Cys Arg Leu His Thr Val Arg Ala Ser Leu Glu Asp Leu Gly Trp Ala
            260                 265                 270

Asp Trp Val Leu Ser Pro Arg Glu Val Gln Val Thr Met Cys Ile Gly
        275                 280                 285

Ala Cys Pro Ser Gln Phe Arg Ala Ala Asn Met His Ala Gln Ile Lys
    290                 295                 300

Thr Arg Leu His Arg Leu Lys Pro Asp Thr Val Pro Ala Pro Cys Cys
305                 310                 315                 320

Val Pro Ala Ser Tyr Asn Pro Met Val Leu Ile Gln Lys Thr Asp Thr
                325                 330                 335

Gly Val Ser Leu Gln Thr Tyr Asp Asp Leu Leu Ala Lys Asp Cys His
            340                 345                 350

Cys Ile


<210> SEQ ID NO 104
<211> LENGTH: 343
<212> TYPE: PRT
<213> ORGANISM: Artificial Sequence
<220> FEATURE:
<223> OTHER INFORMATION: Hinge deleted human IgG1-Fc(L234A, L235A,
      N297A)(T366W)-GS(G4S)3-GDF15 variant (delta N3, G4N, D5S, H6T,
      S64R/ FM11-1)

<400> SEQUENCE: 104

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Ala Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175
```

```
Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Ser Gly Gly Gly Gly Ser
    210                 215                 220

Gly Gly Gly Gly Ser Gly Gly Gly Gly Ser Asn Ser Thr Cys Pro Leu
225                 230                 235                 240

Gly Pro Gly Arg Cys Cys Arg Leu His Thr Val Arg Ala Ser Leu Glu
                245                 250                 255

Asp Leu Gly Trp Ala Asp Trp Val Leu Ser Pro Arg Glu Val Gln Val
            260                 265                 270

Thr Met Cys Ile Gly Ala Cys Pro Ser Gln Phe Arg Ala Ala Asn Met
        275                 280                 285

His Ala Gln Ile Lys Thr Arg Leu His Arg Leu Lys Pro Asp Thr Val
    290                 295                 300

Pro Ala Pro Cys Cys Val Pro Ala Ser Tyr Asn Pro Met Val Leu Ile
305                 310                 315                 320

Gln Lys Thr Asp Thr Gly Val Ser Leu Gln Thr Tyr Asp Asp Leu Leu
                325                 330                 335

Ala Lys Asp Cys His Cys Ile
            340


<210> SEQ ID NO 105
<211> LENGTH: 353
<212> TYPE: PRT
<213> ORGANISM: Artificial Sequence
<220> FEATURE:
<223> OTHER INFORMATION: Hinge deleted human IgG1-Fc(L234A, L235A,
      N297A)(T366W)-GS(G4S)5-GDF15 variant (delta N3, G4N, D5S, H6T,
      S64R/ FM11-2)

<400> SEQUENCE: 105

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Ala Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
```

180 185 190

Phe Ser Cys Ser Val Met His Glu Ala Leu His Asn His Tyr Thr Gln
195 200 205

Lys Ser Leu Ser Leu Ser Pro Gly Lys Gly Ser Gly Gly Gly Gly Ser
210 215 220

Gly Gly Gly Gly Ser Gly Gly Gly Gly Ser Gly Gly Gly Gly Ser Gly
225 230 235 240

Gly Gly Gly Ser Asn Ser Thr Cys Pro Leu Gly Pro Gly Arg Cys Cys
245 250 255

Arg Leu His Thr Val Arg Ala Ser Leu Glu Asp Leu Gly Trp Ala Asp
260 265 270

Trp Val Leu Ser Pro Arg Glu Val Gln Val Thr Met Cys Ile Gly Ala
275 280 285

Cys Pro Ser Gln Phe Arg Ala Ala Asn Met His Ala Gln Ile Lys Thr
290 295 300

Arg Leu His Arg Leu Lys Pro Asp Thr Val Pro Ala Pro Cys Cys Val
305 310 315 320

Pro Ala Ser Tyr Asn Pro Met Val Leu Ile Gln Lys Thr Asp Thr Gly
325 330 335

Val Ser Leu Gln Thr Tyr Asp Asp Leu Leu Ala Lys Asp Cys His Cys
340 345 350

Ile

<210> SEQ ID NO 106
<211> LENGTH: 363
<212> TYPE: PRT
<213> ORGANISM: Artificial Sequence
<220> FEATURE:
<223> OTHER INFORMATION: Hinge deleted human IgG1-Fc(L234A, L235A, N297A)(T366W)-GS(G4S)7-GDF15 variant (delta N3, G4N, D5S, H6T, S64R/ FM11-3)

<400> SEQUENCE: 106

Ala Pro Glu Ala Ala Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Ala Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Trp Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

-continued

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys Gly Ser Gly Gly Gly Gly Ser
210 215 220

Gly Gly Gly Gly Ser Gly Gly Gly Gly Ser Gly Gly Gly Gly Ser Gly
225 230 235 240

Gly Gly Gly Ser Gly Gly Gly Gly Ser Gly Gly Gly Gly Ser Asn Ser
245 250 255

Thr Cys Pro Leu Gly Pro Gly Arg Cys Cys Arg Leu His Thr Val Arg
260 265 270

Ala Ser Leu Glu Asp Leu Gly Trp Ala Asp Trp Val Leu Ser Pro Arg
275 280 285

Glu Val Gln Val Thr Met Cys Ile Gly Ala Cys Pro Ser Gln Phe Arg
290 295 300

Ala Ala Asn Met His Ala Gln Ile Lys Thr Arg Leu His Arg Leu Lys
305 310 315 320

Pro Asp Thr Val Pro Ala Pro Cys Cys Val Pro Ala Ser Tyr Asn Pro
325 330 335

Met Val Leu Ile Gln Lys Thr Asp Thr Gly Val Ser Leu Gln Thr Tyr
340 345 350

Asp Asp Leu Leu Ala Lys Asp Cys His Cys Ile
355 360

<210> SEQ ID NO 107
<211> LENGTH: 352
<212> TYPE: PRT
<213> ORGANISM: Artificial Sequence
<220> FEATURE:
<223> OTHER INFORMATION: Hinge deleted human IgG1-Fc(L234A, L235A, N297A)(T366W)-GS(EEEA)6-GDF15 variant (delta N3, G4N, D5S, H6T, S64R/ FM11-4)

<400> SEQUENCE: 107

Ala Pro Glu Ala Ala Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Ala Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Trp Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu

```
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Ser Glu Glu Glu Ala Glu
    210                 215                 220

Glu Glu Ala Glu Glu Glu Ala Glu Glu Glu Ala Glu Glu Glu Ala Glu
225                 230                 235                 240

Glu Glu Ala Asn Ser Thr Cys Pro Leu Gly Pro Gly Arg Cys Cys Arg
                245                 250                 255

Leu His Thr Val Arg Ala Ser Leu Glu Asp Leu Gly Trp Ala Asp Trp
            260                 265                 270

Val Leu Ser Pro Arg Glu Val Gln Val Thr Met Cys Ile Gly Ala Cys
        275                 280                 285

Pro Ser Gln Phe Arg Ala Ala Asn Met His Ala Gln Ile Lys Thr Arg
    290                 295                 300

Leu His Arg Leu Lys Pro Asp Thr Val Pro Ala Pro Cys Cys Val Pro
305                 310                 315                 320

Ala Ser Tyr Asn Pro Met Val Leu Ile Gln Lys Thr Asp Thr Gly Val
                325                 330                 335

Ser Leu Gln Thr Tyr Asp Asp Leu Leu Ala Lys Asp Cys His Cys Ile
            340                 345                 350
```

<210> SEQ ID NO 108
<211> LENGTH: 352
<212> TYPE: PRT
<213> ORGANISM: Artificial Sequence
<220> FEATURE:
<223> OTHER INFORMATION: Hinge deleted human IgG1-Fc(L234A, L235A, N297A)(T366W)-GSGGSS(PT)10-GDF15 variant (delta N3, G4N, D5S, H6T, S64R/ FM11-5)

<400> SEQUENCE: 108

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Ala Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175
```

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys Gly Ser Gly Gly Ser Ser Pro
210 215 220

Thr Pro Thr Pro Thr Pro Thr Pro Thr Pro Thr Pro Thr Pro Thr Pro
225 230 235 240

Thr Pro Thr Asn Ser Thr Cys Pro Leu Gly Pro Gly Arg Cys Cys Arg
245 250 255

Leu His Thr Val Arg Ala Ser Leu Glu Asp Leu Gly Trp Ala Asp Trp
260 265 270

Val Leu Ser Pro Arg Glu Val Gln Val Thr Met Cys Ile Gly Ala Cys
275 280 285

Pro Ser Gln Phe Arg Ala Ala Asn Met His Ala Gln Ile Lys Thr Arg
290 295 300

Leu His Arg Leu Lys Pro Asp Thr Val Pro Ala Pro Cys Cys Val Pro
305 310 315 320

Ala Ser Tyr Asn Pro Met Val Leu Ile Gln Lys Thr Asp Thr Gly Val
325 330 335

Ser Leu Gln Thr Tyr Asp Asp Leu Leu Ala Lys Asp Cys His Cys Ile
340 345 350

<210> SEQ ID NO 109
<211> LENGTH: 353
<212> TYPE: PRT
<213> ORGANISM: Artificial Sequence
<220> FEATURE:
<223> OTHER INFORMATION: Hinge deleted human IgG1-Fc(L234A, L235A, N297A)(T366W)-GS(EAAAK)5-GDF15 variant (delta N3, G4N, D5S, H6T, S64R/ FM11-6)

<400> SEQUENCE: 109

Ala Pro Glu Ala Ala Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Ala Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Trp Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

```
Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Ser Glu Ala Ala Ala Lys
    210                 215                 220

Glu Ala Ala Ala Lys Glu Ala Ala Ala Lys Glu Ala Ala Ala Lys Glu
225                 230                 235                 240

Ala Ala Ala Lys Asn Ser Thr Cys Pro Leu Gly Pro Gly Arg Cys Cys
                245                 250                 255

Arg Leu His Thr Val Arg Ala Ser Leu Glu Asp Leu Gly Trp Ala Asp
            260                 265                 270

Trp Val Leu Ser Pro Arg Glu Val Gln Val Thr Met Cys Ile Gly Ala
        275                 280                 285

Cys Pro Ser Gln Phe Arg Ala Ala Asn Met His Ala Gln Ile Lys Thr
    290                 295                 300

Arg Leu His Arg Leu Lys Pro Asp Thr Val Pro Ala Pro Cys Cys Val
305                 310                 315                 320

Pro Ala Ser Tyr Asn Pro Met Val Leu Ile Gln Lys Thr Asp Thr Gly
                325                 330                 335

Val Ser Leu Gln Thr Tyr Asp Asp Leu Leu Ala Lys Asp Cys His Cys
            340                 345                 350

Ile
```

<210> SEQ ID NO 110
<211> LENGTH: 4
<212> TYPE: PRT
<213> ORGANISM: Artificial Sequence
<220> FEATURE:
<223> OTHER INFORMATION: linker EEEA

<400> SEQUENCE: 110

```
Glu Glu Glu Ala
1
```

<210> SEQ ID NO 111
<211> LENGTH: 5
<212> TYPE: PRT
<213> ORGANISM: Artificial Sequence
<220> FEATURE:
<223> OTHER INFORMATION: linker - EAAAK

<400> SEQUENCE: 111

```
Glu Ala Ala Ala Lys
1               5
```

<210> SEQ ID NO 112
<211> LENGTH: 4
<212> TYPE: PRT
<213> ORGANISM: Artificial Sequence
<220> FEATURE:
<223> OTHER INFORMATION: NGDH (abbreviation for human GDF15 with delta N2)

<400> SEQUENCE: 112

```
Asn Gly Asp His
1
```

<210> SEQ ID NO 113
<211> LENGTH: 5
<212> TYPE: PRT

-continued

```
<213> ORGANISM: Artificial Sequence
<220> FEATURE:
<223> OTHER INFORMATION: WSNST (abbreviation for human GDF15 with delta
      N3, WS insertion, G4N, D5S, H6T)

<400> SEQUENCE: 113

Trp Ser Asn Ser Thr
1               5
```

LONG-ACTING GDF15 FUSION PROTEIN AND PHARMACEUTICAL COMPOSITION COMPRISING SAME

CROSS REFERENCE TO RELATED APPLICATIONS

This application is a national stage application of PCT/KR2020/016842 filed Nov. 25, 2020, which claims priority based on Korean Patent Application No. 10-2019-0153680 filed Nov. 26, 2019.

SEQUENCE LISTING

The content of the electronically submitted sequence listing, file name: Sequence_Listing_As_Filed.txt; size: 218,630 bytes; and date of creation: Apr. 15, 2022, filed herewith, is incorporated herein by reference in its entirety.

TECHNICAL FIELD

The present invention relates to a fusion protein that includes a GDF15 variant having increased physiological activity and in vivo stability, and a pharmaceutical composition comprising the same.

BACKGROUND ART

Growth differentiation factor-15 (GDF15) is also called macrophage inhibitory cytokine-1 (MIC-1), placental bone morphogenetic protein (PBMP), or nonsteroidal anti-inflammatory drug-activated gene-1 (NAG-1), and is a protein that is a member of the transforming growth factor-beta (TGF-β) superfamily.

Recently, study results have shown that GDF15 inhibits dietary intake through binding to GDNF family receptor alpha-like (GFRAL) and ret proto-oncogene (RET), which are specifically expressed in brain tissue, and thus results in body weight loss (Tsai V W, et al., PLoS One 2013; 8(2): e55174; U.S. Pat. No. 8,192,735). In addition, several studies have demonstrated that GDF15 has an excellent body weight loss effect in a case of being administered to various obese animal models, and have identified that in addition to such an effect, GDF15 further has metabolic advantages such as lowering blood glucose level, improving lipid level, and improving insulin resistance.

However, the wild-type GDF15 is problematic in that in a case where it is used medically, high frequency of administration is needed due to its short in vivo half-life. Accordingly, efforts are being made to develop long-acting formulations that are intended to increase an in vivo half-life of GDF15.

Meanwhile, among several techniques of producing long-acting formulations, an immunoglobulin Fc fusion technique is most widely used in that it results in increased in vivo half-life and there is little concern about adverse effects such as toxicity or induction of immune responses. To develop an immunoglobulin Fc-fused GDF15 protein into a long-acting therapeutic drug, the following several conditions must be satisfied.

First, decrease in in vitro activity caused by fusion should be minimized. It is known that activity of GDF15 fusion proteins varies greatly depending on fusion site. Therefore, activity of Fc-fused GDF15 proteins, in which a mutation has been introduced into the GDF15, may vary depending on whether fusion has occurred or fusion site. Second, fusion should result in increased in vivo half-life, and the increased in vivo half-life should display a pharmacokinetic profile which enables administration at an interval of once a week in humans. Third, considering that most biopharmaceuticals may cause immunogenicity in patients, risk of immunogenicity caused by a fusion linker or mutation should be minimized. Fourth, there should be no stability problems due to fusion site or mutation introduction. Fifth, since an unwanted immune response may occur depending on isotypes of fused immunoglobulin, an alternative thereto is required.

While making efforts to improve physiological activity and stability of GDF15, the present inventors have identified that in a case where a mutation is introduced at a particular location of GDF15 and an immunoglobulin Fc region is bound thereto, the GDF15 has enhanced activity and increased in vivo half-life, and thus have completed the present invention.

DISCLOSURE OF INVENTION

Technical Problem

An object of the present invention is to provide a GDF15 variant having improved physiological activity and stability, and a long-acting GDF15 fusion protein.

Another object of the present invention is to provide a pharmaceutical composition for preventing or treating diabetes, obesity, dyslipidemia, or metabolic syndrome, comprising, as an active ingredient, the GDF15 variant or the long-acting GDF15 fusion protein.

Solution to Problem

To achieve the above objects, in an aspect of the present invention, there is provided a GDF15 variant represented by Formula (I).

N-terminal extension domain-core domain (I)

In another aspect of the present invention, there is provided a long-acting GDF15 fusion protein, in which the GDF15 variant is bound to human IgG Fc or a variant thereof.

In yet another aspect of the present invention, there is provided a fusion protein dimer, comprising two of the long-acting GDF15 fusion protein.

In still yet another aspect of the present invention, there is provided an isolated nucleic acid molecule, encoding the GDF15 variant or the GDF15 fusion protein.

In still yet another aspect of the present invention, there is provided an expression vector, comprising the nucleic acid molecule.

In still yet another aspect of the present invention, there is provided a host cell, comprising the expression vector.

In still yet another aspect of the present invention, there is provided a pharmaceutical composition for preventing or treating diabetes, obesity, dyslipidemia, or metabolic syndrome, comprising, as an active ingredient, the GDF15 variant, the long-acting GDF15 fusion protein, or the fusion protein dimer.

Advantageous Effects of Invention

The GDF15 variant or the long-acting GDF15 fusion protein, according to the present invention, is superior to conventional GDF15 variants in terms of in vitro efficacy, binding affinity for GDF15 receptors, and body weight loss effect.

Therefore, a pharmaceutical composition, which comprises, as an active ingredient, the GDF15 variant, the long-acting GDF15 fusion protein, or the fusion protein dimer, of the present invention, causes appetite suppression, and thus can be effectively used as a therapeutic agent for metabolic diseases or obesity.

Furthermore, the pharmaceutical composition, which comprises, as an active ingredient, the GDF15 variant, the long-acting GDF15 fusion protein, or the fusion protein dimer, can be used in combination therapy or the like with chemical drugs and other therapeutic agents for metabolic diseases, and can be effectively used in combination therapy with conventional therapeutic agents for metabolic diseases or obesity.

BRIEF DESCRIPTION OF DRAWINGS

FIG. 1 illustrates results obtained by comparing, in terms of activity, long-acting GDF15 fusion proteins (dimers: FM4, FM4-1, FM4-2, and FM4-3) in which asparagine (N), which is the amino acid at position 56 in mature GDF15, and/or aspartic acid (D), which is the amino acid at position 103 in mature GDF15, is substituted with another amino acid.

FIG. 2 illustrates results obtained by comparing, in terms of activity, long-acting GDF15 fusion proteins (dimers: FM9, FM13, FM14, FM15, and FM16) in which serine (S), which is the amino acid at position 64 in mature GDF15 is substituted with another amino acid.

FIG. 3 illustrates results obtained by comparing, in terms of activity, long-acting GDF15 fusion proteins (dimers: FM4, FM5, and FM9).

FIG. 4 illustrates results obtained by comparing, in terms of binding affinity for GDF15 receptors (GFRAL and RET), long-acting GDF15 fusion proteins (dimers: FM4, FM5, and FM9).

FIG. 5 illustrates results obtained by comparing, in terms of activity, long-acting GDF15 fusion proteins (dimers: FM1, and FM10).

FIG. 6 illustrates results obtained by comparing, in terms of activity, long-acting GDF15 fusion proteins (dimers: FM2, and FM11).

FIG. 7 illustrates results obtained by comparing, in terms of activity, long-acting GDF15 fusion proteins (dimers: FM3, and FM12).

FIG. 8 illustrates results obtained by comparing, in terms of binding affinity for GDF15 receptors (GFRAL and RET), long-acting GDF15 fusion proteins (dimers: FM10 and FM11).

FIG. 9 illustrates results obtained by comparing, in terms of activity depending on linker type and length, long-acting GDF15 fusion proteins (dimers: FM9-1, FM9-2, FM9-3, FM9-4, FM9-5, and FM9-6).

FIG. 10 illustrates results obtained by comparing, in terms of activity depending on linker type and length, long-acting GDF15 fusion proteins (dimers: FM11-1, FM11-2, FM11-3, FM11-4, FM11-5, and FM11-6).

FIG. 11 illustrates results obtained by comparing long-acting GDF15 fusion proteins (dimers; FM9-4, FM9-6, FM11-4, and FM11-6) in terms of change of body weight (%) in diet-induced obese mice (DIO mice), by repeated administration.

FIG. 12 illustrates results obtained by comparing long-acting GDF15 fusion proteins (dimers; FM9-6) in terms of change of body weight (%) in diet-induced obese mice (DIO mice), by single administration.

FIG. 13 illustrates results obtained by comparing long-acting GDF15 fusion proteins (dimers; FM9-6) in terms of change of body weight (%) in ob/ob mice, by repeated administration.

BEST MODE FOR CARRYING OUT THE INVENTION

Hereinafter, the present invention will be described in more detail.

GDF15 Variant

In an aspect of the present invention, there is provided a GDF15 variant represented by Formula (I):

N-terminal extension domain-core domain (I).

In Formula (I), the N-terminal extension domain is a polypeptide consisting of any one amino acid sequence of SEQ ID NOs: 3 to 5; and the core domain is a polypeptide represented by SEQ ID NO: 20, or a polypeptide derived from SEQ ID NO: 20 in which any one amino acid selected from the group consisting of amino acids at positions 15, 50, 58, 97, and combinations thereof in the amino acid sequence of SEQ ID NO: 20 is substituted with another amino acid;

wherein arginine (R), which is the amino acid at position 15, may be substituted with alanine (A), aspartic acid (D), asparagine (N), cysteine (C), glutamic acid (E), glutamine (Q), glycine (G), histidine (H), isoleucine (I), leucine (L), lysine (K), methionine (M), phenylalanine (F), proline (P), serine (S), threonine (T), tryptophan (W), tyrosine (Y), or valine (V), asparagine (N), which is the amino acid at position 50, may be substituted with alanine, arginine (R), aspartic acid, cysteine, glutamic acid, glutamine, glycine, histidine, isoleucine, leucine, lysine, methionine, phenylalanine, proline, serine, threonine, tryptophan, tyrosine, or valine, serine (S), which is the amino acid at position 58, may be substituted with alanine, arginine, aspartic acid, asparagine, cysteine, glutamic acid, glutamine, glycine, histidine, isoleucine, leucine, lysine, methionine, phenylalanine, proline, threonine, tryptophan, tyrosine, or valine, and aspartic acid (D), which is the amino acid at position 97, may be substituted with alanine, arginine, asparagine, cysteine, glutamic acid, glutamine, glycine, histidine, isoleucine, leucine, lysine, methionine, phenylalanine, proline, serine, threonine, tryptophan, tyrosine, or valine.

As used herein, the term "core domain" refers to a polypeptide having an amino acid sequence from positions 7 to 112 in the amino acid sequence of GDF15 of SEQ ID NO: 1, including a polypeptide represented by SEQ ID NO: 20, or a polypeptide derived from SEQ ID NO: 20 in which any one amino acid selected from the group consisting of amino acids at positions 15, 50, 58, 97, and combinations thereof in the amino acid sequence of SEQ ID NO: 20 is substituted with another amino acid. The first core domain may consist of the amino acid sequence of SEQ ID NO: 2.

Specifically, the core domain may include any one variation selected from the group consisting of the following variations (1) to (6):

(1) a variation in which arginine (R), which is the amino acid at position 15 in the amino acid sequence of SEQ ID NO: 20, is substituted with asparagine (N);

(2) a variation in which asparagine (N), which is the amino acid at position 50 in the amino acid sequence of SEQ ID NO: 20, is substituted with leucine (L);
(3) a variation in which serine (S), which is the amino acid at position 58 in the amino acid sequence of SEQ ID NO: 20, is substituted with lysine (K), arginine (R), asparagine (N), aspartic acid (D), glutamic acid (E), cysteine (C), or leucine (L);
(4) a variation in which aspartic acid (D), which is the amino acid at position 97 in the amino acid sequence of SEQ ID NO: 20, is substituted with leucine (L);
(5) a variation in which asparagine (N), which is the amino acid at position 50 in the amino acid sequence of SEQ ID NO: 20, and aspartic acid (D), which is the amino acid at position 97 in the amino acid sequence of SEQ ID NO: 20, are each substituted with cysteine (C) or serine (S); and
(6) a variation in which arginine (R), which is the amino acid at position 15 in the amino acid sequence of SEQ ID NO: 20, is substituted with asparagine (N), and serine (S), which is the amino acid at position 58 in the amino acid sequence of SEQ ID NO: 20, is substituted with lysine (K) or arginine (R).

Here, the core domain may consist of any one amino acid sequence selected from SEQ ID NOs: 6 to 19.

The N-terminal extension domain is a domain bound to the N-terminus of the above-described core domain, and may be a polypeptide consisting of any one amino acid sequence of SEQ ID NOs: 3 to 5.

As used herein, the expression "ΔN2" may also be indicated as "delta N2", meaning that in the amino acid sequence of human GDF15 represented by SEQ ID NO: 1, the amino acids at positions 1 and 2 are deleted. In a case where ΔN2 is expressed as an N-terminal extension domain, it may be expressed as "NGDH" (SEQ ID NO: 112).

As used herein, the expression "ΔN3, WS insertion, G4N, D5S, H6T" may also be indicated as "delta N3, WS insertion, G4N, D5S, H6T", meaning that in the amino acid sequence of human GDF15 represented by SEQ ID NO: 1, the amino acids at positions 1 to 3 are deleted, and tryptophan and serine are inserted therein; glycine, which is the amino acid at position 4, is substituted with asparagine; aspartic acid, which is the amino acid at position 5, is substituted with serine; and histidine, which is the amino acid at position 6, is substituted with threonine. In a case where the ΔN3, WS insertion, G4N, D5S, H6T is expressed as an N-terminal extension domain, it may be indicated as "WSNST" (SEQ ID NO: 113).

As used herein, the expression "ΔN3, G4N, D5S, H6T" may also be indicated as "delta N3, G4N, D5S, H6T", meaning that in the amino acid sequence of human GDF15 represented by SEQ ID NO: 1, the amino acids at positions 1 to 3 are deleted; glycine, which is the amino acid at position 4, is substituted with asparagine; aspartic acid, which is the amino acid at position 5, is substituted with serine; and histidine, which is the amino acid at position 6, is substituted with threonine. In a case where the "ΔN3, G4N, D5S, H6T" is expressed as an N-terminal extension domain, it may be expressed as "NST."

The GDF15 variant may include an N-terminal extension domain consisting of an amino acid sequence represented by SEQ ID NO: 3 and a core domain consisting of any one amino acid sequence selected from SEQ ID NOs: 6 to 20. In addition, the GDF15 variant may include an N-terminal extension domain consisting of an amino acid sequence represented by SEQ ID NO: 4 and a core domain consisting of any one amino acid sequence selected from SEQ ID NOs: 6 to 20. Furthermore, the GDF15 variant may include an N-terminal extension domain consisting of an amino acid sequence represented by SEQ ID NO: 5 and a core domain consisting of any one amino acid sequence selected from SEQ ID NO: 6 to 19.

Preferably, the GDF15 variant may include an N-terminal extension domain consisting of an amino acid sequence represented by SEQ ID NO: 3 and a core domain consisting of an amino acid sequence represented by SEQ ID NO: 8, 9, or 20. In addition, the GDF15 variant may include an N-terminal extension domain consisting of an amino acid sequence represented by SEQ ID NO: 4 and a core domain consisting of an amino acid sequence represented by SEQ ID NO: 8, 9, or 20. Furthermore, the GDF15 variant may include an N-terminal extension domain consisting of an amino acid sequence represented by SEQ ID NO: 5 and a core domain consisting of any one amino acid sequence selected from SEQ ID NOs: 6, 7, and 10 to 19. Here, the GDF15 variant may consist of any one amino acid sequence selected from SEQ ID NOs: 21 to 39.

Long-Acting GDF15 Fusion Protein

In another aspect of the present invention, there is provided a long-acting GDF15 fusion protein, in which the GDF15 variant is bound to human IgG Fc or a variant thereof.

The human IgG Fc or a variant thereof may be Fc of IgG1, IgG2, IgG3, or IgG4, or a variant thereof. Specifically, the human IgG Fc or a variant thereof may be human IgG1 Fc or a variant thereof, and the human IgG1 Fc may consist of an amino acid sequence represented by SEQ ID NO: 41.

The human IgG Fc or a variant thereof may be a contiguous amino acid sequence that is 90%, 92%, 95%, 96%, 97%, 98%, 99%, or 100% identical to SEQ ID NO: 41, or a fragment of the Fc including a CH3 domain. In certain embodiments, the human IgG Fc or a variant thereof may be a contiguous amino acid sequence that is 90%, 92%, 95%, 96%, 97%, 98%, 99%, or 100% identical to SEQ ID NO: 41, or a fragment of the Fc including a CH2 domain and a CH3 domain. In certain embodiments, the human IgG Fc or a variant thereof may be a contiguous amino acid sequence that is 90%, 92%, 95%, 96%, 97%, 98%, 99%, or 100% identical to SEQ ID NO: 41, or a fragment of the Fc including a partial hinge region, a CH2 domain, and a CH3 domain. In certain embodiments, the human IgG Fc or a variant thereof may have an amino acid sequence that is 90%, 92%, 95%, 96%, 97%, 98%, 99%, or 100% identical to SEQ ID NO: 41.

The IgG Fc or a variant thereof includes a first polypeptide including an IgG1 Fc sequence, the IgG Fc sequence including a CH3 sequence that includes at least one engineered protuberance; and a second polypeptide including an IgG1 Fc sequence, the IgG Fc sequence including a CH3 sequence that includes at least one engineered cavity, in which the first polypeptide dimerizes with the second polypeptide via positioning of the protuberance of the first polypeptide into the cavity of the second polypeptide.

Specifically, the first polypeptide may include an engineered protuberance that allows binding to another IgG Fc polypeptide (for example, second polypeptide) including an engineered cavity. The second polypeptide may include an engineered cavity that allows binding to another IgG Fc polypeptide (for example, first polypeptide) including an engineered protuberance. In addition, the protuberance of the first polypeptide and the cavity of the second polypeptide may be each engineered into a CH3 domain of IgG Fc. Here, the protuberance of the first polypeptide and the cavity of the second polypeptide are neither connected nor bound to the GDF15 variant.

The engineered protuberance may include at least one substitution in the amino acid sequence of human IgG1 Fc having an amino acid sequence represented by SEQ ID NO: 41. Here, the amino acid positions are numbered according to EU numbering. The substitution may be present at a position selected from the group consisting of amino acid residues 347, 366, and 394. For example, the substitution may be any one selected from the group consisting of Q347W/Y, T366W/Y, T394W/Y, and combinations thereof. In addition, the engineered cavity may include at least one substitution in corresponding amino acids in the human IgG1 Fc sequence, and the substitution may be present at a position selected from the group consisting of amino acid residues 366, 368, 394, 405, and 407. For example, the substitution may be any one selected from the group consisting of T366S, L368A, T394S, F405T/V/A, Y407T/V/A, and combinations thereof.

Preferably, the protuberance may include the substitution T366W/Y, and the cavity may include any one substitution selected from the group consisting of T366S, L368A, Y407T/V/A, and combinations thereof. For example, the protuberance may include the substitution T366W/Y, and the cavity may include the substitution Y407T/V/A. In addition, the protuberance may include the substitution T366Y, and the cavity may include the substitution Y407T. In addition, the protuberance may include the substitution T366W, and the cavity may include the substitution Y407A. In addition, the protuberance may include the substitution T394Y, and the cavity may include the substitution Y407T.

The first polypeptide may consist of any one amino acid sequence selected from SEQ ID NOs: 42, 44, and 46, and the second polypeptide may consist of any one amino acid sequence selected from SEQ ID NOs: 43, 45, and 47.

The protuberance is referred to as “knob” and the cavity is referred to as “hole”.

The first polypeptide is Fc ‘knob’ including an engineered protuberance, and the second polypeptide is Fc ‘hole’ including an engineered protuberance. The first and second polypeptides may be physically associated with each other via non-covalent interactions (for example, hydrophobic effects, such as hydrophobic interaction between the knob and hole regions of the Fc), covalent bonds (for example, disulfide bonds such as one or two or more disulfide bonds between hinge regions of the Fc in the first and second polypeptides), or both.

As used herein, the term “dimer” refers to a protein complex including at least two polypeptides. Each of these polypeptides includes an N-terminus and a C-terminus. At least two polypeptides may be associated with each other via one or both of covalent and non-covalent (for example, electrostatic, π-effects, van der Waals forces, and hydrophobic effects) interactions. The two polypeptides may have the same amino acid sequence or may be different from each other. In a case where the two polypeptides are identical to each other, the dimer is referred to as a (homo)dimer; and in a case where the two polypeptides are different from each other, the dimer is referred to as a heterodimer.

The human IgG Fc or a variant thereof may be a heterodimer including a first polypeptide and a second polypeptide; and the heterodimer may be a heterodimer formed of A-1 (SEQ ID NO: 42) and A-2 (SEQ ID NO: 43), a heterodimer formed of B-1 (SEQ ID NO: 44) and B-2 (SEQ ID NO: 45), or a heterodimer formed of C-1 (SEQ ID NO: 46) and C-2 (SEQ ID NO: 47).

In addition, the IgG Fc or a variant thereof may include an additional mutation, to improve properties of a long-acting GDF15 fusion protein. Specifically, a heterodimer consisting of the first polypeptide and the second polypeptide may include an additional mutation.

For example, the IgG Fc or a variant thereof may include mutation(s) that abolish (for example, decrease or eliminate) IgG effector function. Specifically, an Fc partner sequence may include mutation(s) that abolish effector functions such as complement-dependent cytotoxicity (CDC), antibody-dependent cellular cytotoxicity (ADCC), and antibody-dependent cellular phagocytosis (ADCP). For example, the mutations E233A and L235A may be introduced into the IgG Fc formed of A-1 and A-2 or a variant thereof (which is a heterodimer), to eliminate IgG1 effector function. The heterodimer formed of B-1 and B-2, which includes the mutation N297A, can be used to eliminate N-linked glycans. Into the heterodimer formed of C-1 and C-2 may be introduced the mutations L234A, L235A, and N297A, to eliminate IgG1 effector function and N-linked glycans.

Binding between the GDF15 variant and the IgG Fc or a variant thereof may be such that the C-terminus of the first polypeptide or the C-terminus of the second polypeptide, in the IgG Fc or a variant thereof, is bound to the N-terminus of the GDF15 variant. In addition, binding between the GDF15 variant and the IgG Fc or a variant thereof may be such that the N-terminus of the first polypeptide or the N-terminus of the second polypeptide, in the IgG Fc or a variant thereof, is bound to the C-terminus of the GDF15 variant. Preferably, binding between the GDF15 variant and the IgG Fc or a variant thereof may be such that the C-terminus of the first polypeptide in the IgG Fc or a variant thereof is bound to the N-terminus of the GDF15 variant.

In addition, binding between the GDF15 variant and the IgG Fc or a variant thereof may be made through a linker. The linker may be a peptide that consists of 10 to 50 amino acid residues, including glycine, serine, alanine, and glutamic acid residues. The linker may include $(G4S)_n$, where n may be an integer of 1 to 10 or an integer of 2 to 7. For example, n may be 2, 3, 4, 5, 6, or 7. In an embodiment of the present invention, a linker including $(G4S)_5$, which is a case where n is an integer of 5, was used.

As an example of a suitable linker other than the linker including $(G4S)_n$ (SEQ ID NO: 48), a linker including $GS(G4S)_n$ (SEQ ID NO: 92, SEQ ID NO: 93, SEQ ID NO: 94), $GS(EEEA)_n$ (SEQ ID NO: 95), $(EEEA)_n$ (SEQ ID NO: 110), $GS(EAAAK)_n$ (SEQ ID NO: 97), $(EAAAK)_n$ (SEQ ID NO: 111), or $GSGGSS(PT)_n$ (SEQ ID NO: 96) may be mentioned, where n may be an integer of 1 to 10. However, the suitable linker is not limited thereto. In an embodiment of the present invention, a linker including $GS(EEEA)_6$, which is a case where n is an integer of 6, or a linker including $GS(EAAAK)_5$, which is a case where n is an integer of 5, was used.

```
Specifically, the linker may be
                                          (SEQ ID NO: 48)
GGGGSGGGGSGGGGSGGGGSGGGGS,

                                          (SEQ ID NO: 92)
GSGGGGSGGGGSGGGGS,

                                          (SEQ ID NO: 93)
GSGGGGSGGGGSGGGGSGGGGSGGGGS,

                                          (SEQ ID NO: 94)
GSGGGGSGGGGSGGGGSGGGGSGGGGSGGGGSGGGGS,
```

-continued (SEQ ID NO: 95)
GSEEEAEEEAEEEAEEEAEEEAEEEA, (SEQ ID NO: 96)
GSGGSSPTPTPTPTPTPTPTPTPTPT,
or (SEQ ID NO: 97)
GSEAAAKEAAAKEAAAKEAAAKEAAAK.

Preferably, the linker may be (SEQ ID NO: 48)
GGGGSGGGGSGGGGSGGGGSGGGGS, (SEQ ID NO: 95)
GSEEEAEEEAEEEAEEEAEEEAEEEA,
or (SEQ ID NO: 97)
GSEAAAKEAAAKEAAAKEAAAKEAAAK.

The long-acting GDF15 fusion protein includes one GDF15 variant per heterodimer consisting of a first polypeptide and a second polypeptide. The GDF15 variant may include at least one N-linked glycan.

The long-acting GDF15 fusion protein may include i) a GDF15 variant consisting of any one amino acid sequence selected from SEQ ID NOs: 21 to 39, ii) a first polypeptide consisting of any one amino acid sequence selected from SEQ ID NOs: 42, 44, and 46, and iii) a second polypeptide consisting of any one amino acid sequence selected from SEQ ID NOs: 43, 45, and 47.

Preferably, the long-acting GDF15 fusion protein may include i) a GDF15 variant consisting of any one amino acid sequence selected from SEQ ID NOs: 21 to 39, ii) a linker consisting of the amino acid sequence of SEQ ID NO: 48, iii) a first polypeptide consisting of the amino acid sequence of SEQ ID NO: 42, and iv) a second polypeptide consisting of the amino acid sequence of SEQ ID NO: 43.

Still preferably, the long-acting GDF15 fusion protein may include i) a GDF15 variant consisting of any one amino acid sequence selected from SEQ ID NOs: 21 to 39, ii) a linker consisting of any one amino acid sequence selected from SEQ ID NOs: 92 to 97, iii) a first polypeptide consisting of the amino acid sequence of SEQ ID NO: 46, and iv) a second polypeptide consisting of the amino acid sequence of SEQ ID NO: 47.

Fusion Protein Dimer

In still yet another aspect of the present invention, there is provided a fusion protein dimer, comprising two of the long-acting GDF15 fusion protein. Specifically, the two long-acting GDF15 fusion proteins are dimerized through GDF15-GDF15 interaction, and this was designated “fusion protein dimer”.

Nucleic Acid Molecule, Expression Vector, and Host Cell

In still yet another aspect of the present invention, there is provided an isolated nucleic acid molecule, encoding the GDF15 variant or the long-acting GDF15 fusion protein.

As used herein, the term “isolated nucleic acid molecule” refers to a nucleic acid molecule of the present invention that has been separated from at least about 50% of proteins, lipids, carbohydrates, or other materials with which it is naturally found when the entire nucleic acid is isolated from source cells; is operably linked to a polynucleotide which it is not linked to in nature; or does not occur in nature as part of a larger polynucleotide sequence. Specifically, the isolated nucleic acid molecule of the present invention is substantially free from any other contaminating nucleic acid molecules, or other contaminants that are found in its natural environment and would interfere with its use in polypeptide production, or its therapeutic, diagnostic, prophylactic, or research application.

Here, the isolated nucleic acid molecule that encodes the GDF15 variant or the long-acting GDF15 fusion protein may have different sequences due to codon redundancy. In addition, the isolated nucleic acid molecule may be appropriately modified or may have a nucleotide added to the N-terminus or C-terminus, depending on purposes, as long as it can produce the GDF15 variant or the long-acting GDF15 fusion protein.

In still yet another aspect of the present invention, there is provided an expression vector, comprising the isolated nucleic acid molecule that encodes the GDF15 variant or the long-acting GDF15 fusion protein.

As used herein, the term “expression vector” refers to a vector which is suitable for transformation of a host cell and contains a nucleic acid sequence that directs or controls expression of an inserted heterologous nucleic acid sequence. The vector includes linear nucleic acids, plasmids, phagemids, cosmids, RNA vectors, viral vectors, and analogs thereof. Examples of the viral vector include, but are not limited to, a retrovirus, an adenovirus, and an adeno-associated virus.

As used herein, the term “expression of a heterologous nucleic acid sequence” or “expression” of a target protein refers to transcription of an inserted DNA sequence, translation of an mRNA transcript, and production of a fusion protein product, an antibody, or an antibody fragment.

A useful expression vector may be RcCMV (Invitrogen, Carlsbad) or a variant thereof. The useful expression vector may include a human cytomegalovirus (CMV) promoter for promoting continuous transcription of a target gene in mammalian cells, and a bovine growth hormone polyadenylation signal sequence for increasing a post-transcriptional RNA stability level.

In still yet another aspect of the present invention, there is provided a host cell, comprising the expression vector.

As used herein, the term “host cell” refers to a prokaryotic or eukaryotic cell into which a recombinant expression vector can be introduced. As used herein, the term “transformed” or “transfected” means that a nucleic acid (for example, vector) is introduced into a cell by a number of techniques known in the art.

The host cell may be transformed or transfected with a DNA sequence of the present invention, and may be used for expression and/or secretion of a target protein. Examples of the host cell that can be used in the present invention may include immortal hybridoma cells, NS/0 myeloma cells, 293 cells, Chinese hamster ovary (CHO) cells, HeLa cells, CAP cells (human amniotic fluid-derived cells), and COS cells.

Pharmaceutical Composition

In a still yet another aspect of the present invention, there is provided a pharmaceutical composition for preventing or treating diabetes, obesity, dyslipidemia, or metabolic syndrome, comprising, as an active ingredient, the GDF15 variant, the long-acting GDF15 fusion protein, or the fusion protein dimer.

The pharmaceutical composition of the present invention can be administered via any route. The composition of the present invention may be provided to an animal either directly (for example, topically, by injection, implantation, or local administration to a tissue site) or systemically (for example, by parenteral or oral administration) using any appropriate means. In a case where the composition of the present invention is parenterally provided, such as by intravenous, subcutaneous, ophthalmic, intraperitoneal, intramuscular, rectal, intraorbital, intracerebral, intracranial, intraspinal, intraventricular, intrathecal, intracisternal, intracapsular, intranasal, or aerosol administration, the composition may be aqueous or include a portion of a physiologically applicable body fluid suspension or solution. Accordingly, since a carrier or vehicle is physiologically acceptable, it may be added to the composition and delivered to a patient. Therefore, physiological saline may be generally included as a body fluid-like carrier for formulations.

In addition, frequency of administration may vary depending on pharmacokinetic parameters of the GDF15 variant in a formulation used. Typically, physicians would administer the pharmaceutical composition until the dose thereof reaches a dose that achieves a desired effect. Thus, the pharmaceutical composition may be administered as a single dose, or two or more doses at time intervals (which may or may not contain an equal amount of a target fusion protein), or may be administered as continuous infusion through an implantable device or catheter. Further refinement of an appropriate dose is routinely made by those skilled in the art and falls within the scope of work which is routinely performed by them.

In addition, a unit dose of the fusion protein in humans is 0.01 μg to 100 mg/kg body weight, and specifically, 1 μg to 10 mg/kg body weight. Although the above-mentioned amount is an optimal amount, the amount may vary depending on a disease to be treated, or presence or absence of adverse effects. An optimal dose may be determined using a conventional experiment. Administration of the fusion protein may be made by periodic bolus injections, or continuous intravenous, subcutaneous, or intraperitoneal administration from an external reservoir (for example, intravenous bag) or an internal reservoir (for example, biodegradable implant).

In addition, the fusion protein of the present invention may be administered to a subject recipient together with other biologically active molecules. However, an optimal combination of the fusion protein and other molecules, and dosage forms and precise doses thereof may be determined by conventional experiments well known in the art.

In still yet another aspect of the present invention, there is provided a use of the GDF15 variant, the long-acting GDF15 fusion protein, or the fusion protein dimer, for prevention or treatment of diabetes, obesity, dyslipidemia, or metabolic syndrome.

In still yet another aspect of the present invention, there is provided a use of the GDF15 variant, the long-acting GDF15 fusion protein, or the fusion protein dimer, for manufacture of a medicament for preventing or treating diabetes, obesity, dyslipidemia, or metabolic syndrome.

In still yet another aspect of the present invention, there is provided a method for preventing or treating diabetes, obesity, dyslipidemia, or metabolic syndrome, comprising a step of administering, to an individual, the GDF15 variant, the long-acting GDF15 fusion protein, or the fusion protein dimer.

Dose, frequency of administration, and route of administration of the GDF15 variant, the long-acting GDF15 fusion protein, or the fusion protein dimer are the same as described above. The individual may be an individual suffering from diabetes, obesity, dyslipidemia, or metabolic syndrome. In addition, the individual may be a mammal, preferably a human.

MODE FOR THE INVENTION

Hereinafter, for better understanding of the present invention, the present invention will be described in detail by way of examples. However, the examples according to the present invention may be modified in a variety of different forms, and the scope of the present invention should not be construed as being limited to the following examples.

Example 1: Production of Long-Acting GDF15 Fusion Protein

Example 1.1: Gene Cloning

In general, in a case where a substance is fused to long-acting Fc or albumin to increase its half-life, the fusion results in a decrease in activity of the substance. To improve this, various GDF15 variants were designed.

First, first polypeptides were prepared by performing substitutions of respective amino acids at positions 32, 51, 56, 60, 64, 90, 92, 93, 97, 101, and 103 in GDF15, which are predicted to have a large effect on protein activity through three-dimensional structure analysis of GDF15, and causing the resulting GDF15's to be bound to IgG1 Fc_knob, and these first polypeptides are shown in Table 1 below.

TABLE 1

| Changes in sequence of GDF15 | Fusion carrier | Linker sequence | SEQ ID NO of fusion protein |
|---|---|---|---|
| ΔN2 | IgG1 Fc_knob (SEQ ID NO: 42) | $(G4S)_5$ (SEQ ID NO: 48) | SEQ ID NO: 49 |
| ΔN2, N56C, D103C | IgG1 Fc_knob (SEQ ID NO: 42) | $(G4S)_5$ (SEQ ID NO: 48) | SEQ ID NO: 65 |
| ΔN2, W32F | IgG1 Fc_knob (SEQ ID NO: 42) | $(G4S)_5$ (SEQ ID NO: 48) | SEQ ID NO: 69 |
| ΔN2, W32H | IgG1 Fc_knob (SEQ ID NO: 42) | $(G4S)_5$ (SEQ ID NO: 48) | SEQ ID NO: 70 |
| ΔN2, W32Y | IgG1 Fc_knob (SEQ ID NO: 42) | $(G4S)_5$ (SEQ ID NO: 48) | SEQ ID NO: 71 |
| ΔN2, Q51H | IgG1 Fc_knob (SEQ ID NO: 42) | $(G4S)_5$ (SEQ ID NO: 48) | SEQ ID NO: 72 |
| ΔN2, Q51L | IgG1 Fc_knob (SEQ ID NO: 42) | $(G4S)_5$ (SEQ ID NO: 48) | SEQ ID NO: 73 |
| ΔN2, Q51E | IgG1 Fc_knob (SEQ ID NO: 42) | $(G4S)_5$ (SEQ ID NO: 48) | SEQ ID NO: 74 |
| ΔN2, Q51N | IgG1 Fc_knob (SEQ ID NO: 42) | $(G4S)_5$ (SEQ ID NO: 48) | SEQ ID NO: 75 |
| ΔN2, Q90H | IgG1 Fc_knob (SEQ ID NO: 42) | $(G4S)_5$ (SEQ ID NO: 48) | SEQ ID NO: 76 |
| ΔN2, Q90E | IgG1 Fc_knob (SEQ ID NO: 42) | $(G4S)_5$ (SEQ ID NO: 48) | SEQ ID NO: 77 |
| ΔN2, Q90K | IgG1 Fc_knob (SEQ ID NO: 42) | $(G4S)_5$ (SEQ ID NO: 48) | SEQ ID NO: 78 |
| ΔN2, D93E | IgG1 Fc_knob (SEQ ID NO: 42) | $(G4S)_5$ (SEQ ID NO: 48) | SEQ ID NO: 79 |
| ΔN2, D93L | IgG1 Fc_knob (SEQ ID NO: 42) | $(G4S)_5$ (SEQ ID NO: 48) | SEQ ID NO: 80 |
| ΔN2, D93N | IgG1 Fc_knob (SEQ ID NO: 42) | $(G4S)_5$ (SEQ ID NO: 48) | SEQ ID NO: 81 |
| ΔN2, D93Q | IgG1 Fc_knob (SEQ ID NO: 42) | $(G4S)_5$ (SEQ ID NO: 48) | SEQ ID NO: 82 |
| ΔN2, Q60L | IgG1 Fc_knob (SEQ ID NO: 42) | $(G4S)_5$ (SEQ ID NO: 48) | SEQ ID NO: 83 |
| ΔN2, Q60N | IgG1 Fc_knob (SEQ ID NO: 42) | $(G4S)_5$ (SEQ ID NO: 48) | SEQ ID NO: 84 |
| ΔN2, S64K | IgG1 Fc_knob (SEQ ID NO: 42) | $(G4S)_5$ (SEQ ID NO: 48) | SEQ ID NO: 54 |
| ΔN2, S64Q | IgG1 Fc_knob (SEQ ID NO: 42) | $(G4S)_5$ (SEQ ID NO: 48) | SEQ ID NO: 85 |
| ΔN2, T92S | IgG1 Fc_knob (SEQ ID NO: 42) | $(G4S)_5$ (SEQ ID NO: 48) | SEQ ID NO: 86 |
| ΔN2, T92E | IgG1 Fc_knob (SEQ ID NO: 42) | $(G4S)_5$ (SEQ ID NO: 48) | SEQ ID NO: 87 |
| ΔN2, S97N | IgG1 Fc_knob (SEQ ID NO: 42) | $(G4S)_5$ (SEQ ID NO: 48) | SEQ ID NO: 88 |
| ΔN2, S97Q | IgG1 Fc_knob (SEQ ID NO: 42) | $(G4S)_5$ (SEQ ID NO: 48) | SEQ ID NO: 89 |

TABLE 1-continued

| Changes in sequence of GDF15 | Fusion carrier | Linker sequence | SEQ ID NO of fusion protein |
|---|---|---|---|
| ΔN2, Y101F | IgG1 Fc_knob (SEQ ID NO: 42) | $(G4S)_5$ (SEQ ID NO: 48) | SEQ ID NO: 90 |
| ΔN2, Y101Q | IgG1 Fc_knob (SEQ ID NO: 42) | $(G4S)_5$ (SEQ ID NO: 48) | SEQ ID NO: 91 |

Specifically, to produce a first polypeptide (FM series) having a structure of Fc_knob-$(G4S)_5$-GDF15 variant and a second polypeptide having Fc_hole structure, gene cloning was conducted using pcDNA3.3 (Invitrogen) expression vector that includes a gene encoding a first polypeptide consisting of any one amino acid sequence of SEQ ID NOs: 49, 60, 65, and 69 to 90 and a gene encoding a second polypeptide consisting of the amino acid sequence of SEQ ID NO: 43. Here, nucleotide sequences encoding the amino acid sequences of SEQ ID NOs: 43, 49, 60, 65, and 69 to 90 were synthesized by making a request to Macrogen, Inc.

Example 1.2: Expression and Purification of Long-Acting GDF15 Fusion Protein (Dimer)

The pcDNA3.3 expression vector cloned in Example 1.1 was transiently transfected into ExpiCHO cell line (Invitrogen). Then, on Day 8, the cell culture was harvested and purified. To purify the first polypeptide and the second polypeptide in the harvest cell culture fluid (HCCF), affinity purification using Protein A resin was performed.

Specifically, the HCCF was loaded onto MabSelect SuRe Protein A resin (GE Healthcare) equilibrated with 1×PBS (pH 7.4), to induce binding. After completion of the binding between the first polypeptide and the second polypeptide, the MabSelect SuRe Protein A resin was washed with 1×PBS (pH 7.4). Then, elution was performed using 0.1 M glycine (pH 3.0) solution, to obtain a final substance.

The first polypeptide and the second polypeptide were neutralized to a level of about pH 8.0 using 1 M Tris-HCl solution. The first polypeptide and the second polypeptide were completely dimerized through knob-in-hole interaction, and this was designated "long-acting GDF15 fusion protein". Two molecules of the long-acting GDF15 fusion protein were dimerized again through GDF15-GDF15 interaction, and this was designated "fusion protein dimer".

Example 2: Measurement of Activity of Long-Acting GDF15 Fusion Protein (Dimer)

Using a fusion protein that includes mature GDF15 consisting of the amino acid sequence of SEQ ID NO: 49, as a control, the long-acting GDF15 fusion proteins produced in Example 1 were compared in terms of GDF15 activity. The GDF15 activity was measured using a BRIGHT-GLO™ luciferase assay kit (Promega) and human embryonic kidney 293 (HEK293) cell line overexpressing GFRAL/RET/SRE-luc.

Specifically, $1\times10^5$ HEK293 cells overexpressing GFRAL/RET/SRE-luc were dispensed into each well of a 96-well-plate in DMEM medium containing 10% FBS, and then incubated for 24 hours at 37° C. and 5% $CO_2$. After 24 hours, each medium in the 96-well-plate was replaced with 50 μl of serum-free medium, and incubated for 4 hours at 37° C. and 5% $CO_2$.

In addition, each of the long-acting GDF15 fusion proteins produced in Example 1 was prepared by 3-fold serial dilution starting from a concentration of 2000 nM using serum-free medium. Then, 50 μl of the long-acting GDF15 fusion protein dilution was added to each well that contains 50 μl of the replaced serum-free medium and the GFRAL/RET/SRE-luc cell line, so that the actual concentration was obtained by 3-fold serial dilution starting from 1000 nM. Then, reaction was allowed to proceed for 4 hours at 37° C. and 5% $CO_2$. After 4 hours, each well was treated with 100 μl of BRIGHT-GLO™ solution, which had been prepared by adding BRIGHT-GLO™ buffer to BRIGHT-GLO™ substrate, and reaction was allowed to proceed for 1 minute at room temperature.

Thereafter, relative light unit (RLU) values were measured with a microplate reader (Perkin Elmer, Wallac Victor X5) capable of measuring luminescence. The results are shown in Table 2 below. Here, two improved long-acting GDF15 fusion proteins were selected based on in vitro GDF15 activity ($E_{max}$ of 100%) of the fusion protein (FWT+Fc_hole) including mature GDF15, which was a control.

TABLE 2

| Changes in sequence of GDF15 in long-acting GDF15 fusion protein: | $E_{max}$ (%) [relative to FWT 100%] | $EC_{50}$ (nM) |
|---|---|---|
| ΔN2: FWT + Fc_hole | 100.0 | 7.0 |
| ΔN2, N56C, D103C: FM4 + Fc_hole | 133.3 | 3.4 |
| ΔN2, W32F | 51.3 | 19.4 |
| ΔN2, W32H | Not active | Not active |
| ΔN2, W32Y | Not active | Not active |
| ΔN2, Q51H | 90.8 | 24.1 |
| ΔN2, Q51L | 88.6 | 15.2 |
| ΔN2, Q51E | 41.9 | 44.2 |
| ΔN2, Q51N | 87.8 | 14.2 |
| ΔN2, Q90H | 73.2 | 43.4 |
| ΔN2, Q90E | 10.5 | 9.3 |
| ΔN2, Q90K | Not active | Not active |
| ΔN2, D93E | 87.6 | 6.5 |
| ΔN2, D93L | 59.1 | 9.0 |
| ΔN2, D93N | 99.6 | 22.6 |
| ΔN2, D93Q | Not active | Not active |
| ΔN2, Q60L | 96.3 | 11.9 |
| ΔN2, Q60N | 43.5 | 7.0 |
| ΔN2, S64K: FM5 + Fc_hole | 147.2 | 7.7 |
| ΔN2, S64Q | 100.0 | 7.9 |
| ΔN2, T92S | 112.0 | 14.9 |
| ΔN2, T92E | 12.3 | 1.1 |
| ΔN2, S97N | 100.2 | 5.6 |
| ΔN2, S97Q | 117.6 | 9.2 |
| ΔN2, Y101F | 37.5 | 31.8 |
| ΔN2, Y101Q | 16.3 | 12.9 |

As a result, the two selected long-acting GDF15 fusion proteins were a long-acting GDF15 fusion protein (hereinafter referred to as FM4+Fc_hole) having the mutations ΔN2, N56C, and D103C, and a long-acting GDF15 fusion protein (hereinafter referred to as FM5+Fc_hole) having the mutations ΔN2 and S64K; and their in vitro GDF15 activity ($E_{max}$) was measured to be 133.3% and 147.2%, respectively. From these results, it was identified that the FM4+Fc_hole and the FM5+Fc_hole had improved in vitro GDF15 activity.

Example 3: Measurement of Activity of Long-Acting GDF15 Fusion Protein (Dimer: FM4+Fc_Hole)

In GDF15-GDF15 interaction between the long-acting GDF15 fusion proteins, it was identified in Example 2 that the FM4+Fc_hole, to which an additional disulfide bond was introduced, had improved in vitro GDF15 activity. On the basis of these results, to identify importance of the disulfide bond, long-acting GDF15 fusion proteins, which were based on the FM4+Fc_hole and in which asparagine (N), which is the amino acid at position 56 in mature GDF15, and/or aspartic acid (D), which is the amino acid at position 103 in mature GDF15, was substituted with another amino acid, were additionally designed as shown in Table 3 below, and produced in the same manner as in Example 1. Then, in vitro GDF15 activity was evaluated in the same manner as in Example 2.

TABLE 3

| Designation of substance (SEQ ID NO) | Changes in sequence of GDF15 in long-acting GDF15 fusion protein | $E_{max}$ (%) [relative to FWT 100%] | $EC_{50}$ (nM) |
|---|---|---|---|
| FWT + Fc_hole (SEQ ID NOs: 49 and 43) | ΔN2 | 100.0 | 5.4 |
| FM4 + Fc_hole (SEQ ID NOs: 65 and 43) | ΔN2, N56C, D103C | 140.1 | 3.6 |
| FM4-1 + Fc_hole (SEQ ID NOs: 66 and 43) | ΔN2, N56S, D103S | 86.4 | 8.9 |
| FM4-2 + Fc_hole (SEQ ID NOs: 64 and 43) | ΔN2, D103L | 109.7 | 10.6 |
| FM4-3 + Fc_hole (SEQ ID NOs: 53 and 43) | ΔN2, N56L | 34.3 | 140.1 |

As a result, as shown in Table 3, it was identified that only the FM4+Fc_hole improved in vitro GDF15 activity ($E_{max}$) as compared with the FWT+Fc_hole (FIG. 1). From these results, it was identified that introduction of cysteine and resultant introduction of a disulfide bond played an important role in improving in vitro GDF15 activity of the FM4+Fc_hole.

Example 4: Measurement of Activity of Long-Acting GDF15 Fusion Protein (Dimer: FM5+Fc_Hole)

It was identified in Example 2 that the FM5+Fc_hole, which is an S64K variant of GDF15, had improved in vitro GDF15 activity. On the basis of these results, long-acting GDF15 fusion proteins, which were based on the FM5+Fc_hole and in which serine (S), which is the amino acid at position 64 in mature GDF15 was substituted with another amino acid, were additionally designed as shown in Table 4 below, and produced in the same manner as in Example 1. Then, in vitro GDF15 activity was evaluated in the same manner as in Example 2.

TABLE 4

| Designation of substance (SEQ ID NO) | Changes in sequence of GDF15 in long-acting GDF15 fusion protein | $E_{max}$ (%) [relative to FWT 100%] | $EC_{50}$ (nM) |
|---|---|---|---|
| FWT + Fc_hole (SEQ ID NOs: 49 and 43) | ΔN2 | 100.0 | 7.3 |
| FM9 + Fc_hole (SEQ ID NOs: 57 and 43) | ΔN2, S64R | 123.2 | 5.0 |
| FM13 + Fc_hole (SEQ ID NOs: 60 and 43) | ΔN2, S64N | 93.3 | 9.6 |
| FM14 + Fc_hole (SEQ ID NOs: 61 and 43) | ΔN2, S64D | 48.2 | 7.9 |
| FM15 + Fc_hole (SEQ ID NOs: 62 and 43) | ΔN2, S64E | 41.0 | 33.6 |
| FM16 + Fc_hole (SEQ ID NOs: 63 and 43) | ΔN2, S64L | 74.7 | 17.6 |

As a result, as shown in Table 4, it was identified that only the FM9+Fc_hole had improved in vitro GDF15 activity ($E_{max}$) as compared with FWT (FIG. 2).

Example 5: Measurement of Binding Affinity of Long-Acting GDF15 Fusion Proteins (Dimers: FM4+Fc_Hole, FM5+Fc_Hole, and FM9+Fc_Hole)

The FM4+Fc_hole, the FM5+Fc_hole, and the FM9+Fc_hole, having improved in vitro GDF15 activity, in Examples 3 and 4 were compared in terms of binding affinity for GFRAL and RET which are GDF15 receptors. To measure binding affinity for the GDF15 receptors, a cell-based enzyme-linked immunosorbent assay (ELISA) was performed using the HEK293 cell line overexpressing GFRAL and RET.

Specifically, $1\times10^5$ HEK293 cells overexpressing GFRAL/RET/SRE-luc were dispensed into each well of a 96-well-plate in DMEM medium containing 10% FBS, and then incubated for 24 hours at 37° C. and 5% $CO_2$. After 24 hours, the medium was removed from each well of the 96-well-plate. Then, each medium was treated with 4% paraformaldehyde and reaction was allowed to proceed for 20 minutes at room temperature. Paraformaldehyde was removed therefrom. Treatment with 0.6% hydrogen peroxide solution was performed, and reaction was allowed to proceed again for 20 minutes. Then, treatment with 3% bovine serum albumin (BSA)-phosphate buffered saline with Tween 20 (PBST) buffer was performed, and blocking was allowed to proceed for 2 hours.

In addition, the FM4+Fc_hole, the FM5+Fc_hole, or the FM9+Fc_hole was subjected to 2-fold serial dilution, starting from 200 μg/mL, using PBS buffer containing 1% BSA. 100 μl of the FM4+Fc_hole, the FM5+Fc_hole, or the FM9+Fc_hole, each of which was diluted in various concentrations, was applied to a 96-well-plate containing a GFRAL/RET-overexpressing cell line, and reaction was allowed to proceed for 2 hours at room temperature. Then, each well was treated with horseradish peroxidase (HRP)-conjugated anti-human IgG-Fc antibody (Jackson ImmunoResearch #109-035-098), and then developed with 3,3,5,5-tetramethylbenzidine (TMB) buffer (Bio-Rad #172-1066).

Each well was treated with 100 μl of TMB solution, and reaction was allowed to proceed for 10 minutes at room temperature. Then, the reaction was stopped using a 2N sulfuric acid ($H_2SO_4$) reagent. Then, absorbance was measured at 450 nm with a microplate reader (Perkin Elmer, Wallac Victor X5) to evaluate binding capacity, to the GDF15 receptors, of the GDF15 variant in the long-acting GDF15 fusion protein (dimer).

As a result, as illustrated in FIG. 4, as compared with the FWT+Fc_hole as a control, the FM9+Fc_hole showed remarkably superior binding affinity for the GDF15 receptors, and the FM4+Fc_hole and the FM5+Fc_hole also showed high binding affinity for the GDF15 receptors.

Example 6: Purity Improvement after Purification for Long-Acting GDF15 Fusion Protein (Dimer)

To improve purification yield, purity, and the like of each long-acting GDF15 fusion protein at the time of producing the same, N-linked glycans were introduced at various positions in GDF15. Presence of N-linked glycans in the GDF15 sequence is known to increase retention time of the corresponding protein in the endoplasmic reticulum and Golgi apparatus during a process of protein secretion, thereby minimizing misfolded products and helping protein expression. Increased retention time has a beneficial effect on folding kinetics and can result in significantly improved heterodimeric (Fc/Fc) knob-in-hole assembly and recovery from mammalian tissue culture.

Evaluation of purity improvement after purification for a substance, obtained by introducing N-linked glycans into a long-acting GDF15 fusion protein, as compared with a dimer of the fusion protein FWT+Fc_hole as a control, was performed in terms of correctly-assembled fusion protein dimer purity using size-exclusion chromatography analysis.

Specifically, long-acting GDF15 fusion proteins, in which N-linked glycans were introduced at various positions in GDF15, were additionally designed. In this regard, variants having increased correctly-assembled fusion protein dimer purity, which was obtained in a case where the variants were produced and subjected to first-step purification in the same manner as in Example 1, as compared with a dimer of the fusion protein FWT+Fc_hole, are shown in Table 6.

TABLE 6

| Designation of substance (SEQ ID NO) | Changes in sequence of GDF15 in long-acting GDF15 fusion protein | Purity after first-step purification (Intact %) |
|---|---|---|
| FWT + Fc_hole (SEQ ID NOs: 49 and 43) | ΔN2 | 50.9 |
| FM1 + Fc_hole (SEQ ID NOs: 50 and 43) | ΔN3, WS insertion, G4N, D5S, H6T | 80.2 |
| FM2 + Fc_hole (SEQ ID NOs: 51 and 43) | ΔN3, G4N, D5S, H6T | 73.0 |
| FM3 + Fc_hole (SEQ ID NOs: 52 and 43) | ΔN2, R21N | 86.3 |
| FM10 + Fc_hole (SEQ ID NOs: 58 and 43) | ΔN3, WS insertion, G4N, D5S, H6T, S64R | 65.2 |
| FM11 + Fc_hole (SEQ ID NOs: 59 and 43) | ΔN3, G4N, D5S, H6T, S64R | 70.3 |
| FM12 + Fc_hole (SEQ ID NOs: 68 and 43) | ΔN2, R21N, S64R | 82.8 |
| B13a/B13b (see sequences in U.S. Pat. No. 9,920,118) | ΔN2, D5T | 75.8 |

As a result, it was identified that the FWT+Fc_hole had correctly-assembled fusion protein dimer purity after first-step purification of 50.9%, whereas the FM1+Fc_hole, the FM2+Fc_hole, the FM3+Fc_hole, the FM10+Fc_hole, the FM11+Fc_hole, and the FM12+Fc_hole, in each of which N-linked glycans were introduced into GDF15, had improved, correctly-assembled fusion protein dimer purity of 80.2%, 73.0%, 86.3%, 65.2%, and 70.3%, respectively.

In addition, the NGM Biopharmaceuticals, Inc.'s fusion protein dimer (B13a/B13b (into which N-linked glycans are introduced) in U.S. Pat. No. 9,920,118 was measured to have purity of 75.8%.

Example 7: Evaluation of Activity of Long-Acting GDF15 Fusion Proteins (Dimers: FM10+Fc_Hole, FM11+Fc_Hole, and FM12+Fc_Hole)

Using the FM1+Fc_hole, the FM2+Fc_hole, and the FM3+Fc_hole, in each of which N-linked glycans were introduced at various positions in GDF15, as controls, the FM10+Fc_hole, the FM11+Fc_hole, and the FM12+Fc_hole were evaluated, in terms of GDF15 activity, in the same manner as in Example 2. The results are shown in Table 7.

TABLE 7

| Designation of substance (SEQ ID NO) | Changes in sequence of GDF15 in long-acting GDF15 fusion protein | $E_{max}$ (%) | $EC_{50}$ (nM) |
|---|---|---|---|
| FM1 + Fc_hole (SEQ ID NOs: 50 and 43) | ΔN3, WS insertion, G4N, D5S, H6T | 100.0 | 1.7 |
| FM2 + Fc_hole (SEQ ID NOs: 51 and 43) | ΔN3, G4N, D5S, H6T | 100.0 | 3.9 |
| FM3 + Fc_hole (SEQ ID NOs: 52 and 43) | ΔN2, R21N | 100.0 | 3.3 |
| FM10 + Fc_hole (SEQ ID NOs: 58 and 43) | ΔN3, WS insertion, G4N, D5S, H6T, S64R | 267.0 | 2.3 |
| FM11 + Fc_hole (SEQ ID NOs: 59 and 43) | ΔN3, G4N, D5S, H6T, S64R | 269.5 | 2.9 |
| FM12 + Fc_hole (SEQ ID NOs: 68 and 43) | ΔN2, R21N, S64R | 221.4 | 5.9 |

As a result, as shown in Table 7, it was identified that the FM10+Fc_hole, the FM11+Fc_hole, and the FM12+Fc_hole had improved GDF15 activity ($E_{max}$) as compared with the FM1+Fc_hole, the FM2+Fc_hole, and the FM3+Fc_hole (FIGS. 5 to 7).

Example 8: Measurement of Binding Affinity of Long-Acting GDF15 Fusion Proteins (Dimers: FM10+Fc_Hole and FM11+Fc_Hole)

Binding affinity of the FM10+Fc_hole or the FM11+Fc_hole for the GDF15 receptors, GFRAL and RET, were compared and evaluated in the same manner as in Example 5. As a result, as illustrated in FIG. 6, remarkably superior affinity for the GDF15 receptors was measured in the FM10+Fc_hole and the FM11+Fc_hole as compared with the FWT+Fc_hole as a control (FIG. 8).

Example 9: Production of Long-Acting GDF15 Fusion Proteins (Dimers: FM6+Fc_Hole, FM7+Fc_Hole, and FM8+Fc_Hole)

Based on the results of Examples 1 to 8, long-acting GDF15 fusion proteins, in which the amino acids at positions 21 and/or 64 were substituted and N-linked glycans were introduced at various positions in GDF15, were additionally designed. In this regard, variants having increased correctly-assembled fusion protein dimer purity, which was obtained in a case where the variants were produced and subjected to first-step purification in the same manner as in Example 1, as compared with a dimer of the fusion protein FWT+Fc_hole, are shown in Table 8.

TABLE 8

| Designation of substance (SEQ ID NO) | Changes in sequence of GDF15 in long-acting GDF15 fusion protein | Purity after first-step purification (Intact %) |
|---|---|---|
| FWT + Fc_hole (SEQ ID NOs: 49 and 43) | ΔN2 | 50.9 |
| FM6 + Fc_hole (SEQ ID NOs: 55 and 43) | ΔN3, WS insertion, G4N, D5S, H6T, S64K | 66.4 |
| FM7 + Fc_hole (SEQ ID NOs: 56 and 43) | ΔN3, G4N, D5S, H6T, S64K | N/A |

TABLE 8-continued

| Designation of substance (SEQ ID NO) | Changes in sequence of GDF15 in long-acting GDF15 fusion protein | Purity after first-step purification (Intact %) |
|---|---|---|
| FM8 + Fc_hole (SEQ ID NOs: 67 and 43) | ΔN2, R21N, S64K | N/A |

Example 10: Optimization of Fusion Carrier and Linker for Long-Acting GDF15 Fusion Proteins In order to conduct optimization studies of a fusion carrier and a linker for the two variants (FM9+Fc_hole and FM11+Fc_hole) showing excellent activity and purity improvement after purification, long-acting GDF15 fusion proteins, in which fusion carriers (SEQ ID NOs: 46 and 47) and various linkers (SEQ ID NOs: 92, 93, 94, 95, 96, and 97) were introduced into respective GDF15 sequences to minimize an effector function, were additionally designed and are shown in Table 9.

TABLE 9

| Designation of substance (SEQ ID NO) | Changes in sequence of GDF15 | Fusion carrier | Linker sequence |
|---|---|---|---|
| FM9-1 + Fc_hole (SEQ ID NOs: 98 and 47) | ΔN2, S64R (SEQ ID NO: 28) | IgG1 Fc_knob (SEQ ID NO: 46) IgG1 Fc_hole (SEQ ID NO: 47) | GS(G4S)$_3$ (SEQ ID NO: 92) |
| FM9-2 + Fc_hole (SEQ ID NOs: 99 and 47) | ΔN2, S64R (SEQ ID NO: 28) | IgG1 Fc_knob (SEQ ID NO: 46) IgG1 Fc_hole (SEQ ID NO: 47) | GS(G4S)$_5$ (SEQ ID NO: 93) |
| FM9-3 + Fc_hole (SEQ ID NOs: 100 and 47) | ΔN2, S64R (SEQ ID NO: 28) | IgG1 Fc_knob (SEQ ID NO: 46) IgG1 Fc_hole (SEQ ID NO: 47) | GS(G4S)$_7$ (SEQ ID NO: 94) |
| FM9-4 + Fc_hole (SEQ ID NOs: 101 and 47) | ΔN2, S64R (SEQ ID NO: 28) | IgG1 Fc_knob (SEQ ID NO: 46) IgG1 Fc_hole (SEQ ID NO: 47) | GS(EEEA)$_6$ (SEQ ID NO: 95) |
| FM9-5 + Fc_hole (SEQ ID NOs: 102 and 47) | ΔN2, S64R (SEQ ID NO: 28) | IgG1 Fc_knob (SEQ ID NO: 46) IgG1 Fc_hole (SEQ ID NO: 47) | GSGGSS(PT)$_{10}$ (SEQ ID NO: 96) |
| FM9-6 + Fc_hole (SEQ ID NOs: 103 and 47) | ΔN2, S64R (SEQ ID NO: 28) | IgG1 Fc_knob (SEQ ID NO: 46) IgG1 Fc_hole (SEQ ID NO: 47) | GS(EAAAK)$_5$ (SEQ ID NO: 97) |
| FM11-1 + Fc_hole (SEQ ID NOs: 104 and 47) | ΔN3, G4N, D5S, H6T, S64R (SEQ ID NO: 30) | IgG1 Fc_knob (SEQ ID NO: 46) IgG1 Fc_hole (SEQ ID NO: 47) | GS(G4S)$_3$ (SEQ ID NO: 92) |
| FM11-2 + Fc_hole (SEQ ID NOs: 105 and 47) | ΔN3, G4N, D5S, H6T, S64R (SEQ ID NO: 30) | IgG1 Fc_knob (SEQ ID NO: 46) IgG1 Fc_hole (SEQ ID NO: 47) | GS(G4S)$_5$ (SEQ ID NO: 93) |
| FM11-3 + Fc_hole (SEQ ID NOs: 106 and 47) | ΔN3, G4N, D5S, H6T, S64R (SEQ ID NO: 30) | IgG1 Fc_knob (SEQ ID NO: 46) IgG1 Fc_hole (SEQ ID NO: 47) | GS(G4S)$_7$ (SEQ ID NO: 94) |
| FM11-4 + Fc_hole (SEQ ID NOs: 107 and 47) | ΔN3, G4N, D5S, H6T, S64R (SEQ ID NO: 30) | IgG1 Fc_knob (SEQ ID NO: 46) IgG1 Fc_hole (SEQ ID NO: 47) | GS(EEEA)$_6$ (SEQ ID NO: 95) |
| FM11-5 + Fc_hole (SEQ ID NOs: 108 and 47) | ΔN3, G4N, D5S, H6T, S64R (SEQ ID NO: 30) | IgG1 Fc_knob (SEQ ID NO: 46) IgG1 Fc_hole (SEQ ID NO: 47) | GSGGSS(PT)$_{10}$ (SEQ ID NO: 96) |
| FM11-6 + Fc_hole (SEQ ID NOs: 109 and 47) | ΔN3, G4N, D5S, H6T, S64R (SEQ ID NO: 30) | IgG1 Fc_knob (SEQ ID NO: 46) IgG1 Fc_hole (SEQ ID NO: 47) | GS(EAAAK)$_5$ (SEQ ID NO: 97) |

Example 10.1: Expression and Purification of Optimized Long-Acting GDF15 Fusion Proteins (Dimers)

The optimized long-acting GDF15 fusion proteins as shown in Table 9 were produced and subjected to first-step purification in the same manner as in Example 1. To obtain a high-purity long-acting GDF15 fusion protein, a pool obtained by completing the first-step purification was subjected to second-step ion exchange (IEX) purification using anion exchange (AEX) resin and cation exchange (CEX) resin.

Specifically, for the anion exchange (AEX), the pool that had undergone the first step was loaded onto POROS HQ™ 50 μM Strong Anion Exchange Resin (Thermo Fisher Scientific) equilibrated with 1×PBS (pH 7.4), to induce binding. After completion of the binding between the first polypeptide and the second polypeptide, the POROS HQ™ 50 μM Strong Anion Exchange Resin was washed with 1×PBS (pH 7.4), and then elution was performed by concentration gradient using 50 mM Tris-HCl (pH 8.0) solution with 1 M sodium chloride, to obtain a final substance. Fractions meeting a criterion for purity of 95% or higher were pooled using size exclusion chromatography analysis.

In addition, for the cation exchange (CEX), the pool that had undergone the first step was subjected to pH adjustment depending on isoelectric points, and then loaded onto POROS XS™ Strong Cation Exchange Resin (Thermo Fisher Scientific) equilibrated with 20 mM sodium phosphate (pH 6.5) solution, to induce binding. After completion of the binding between the first polypeptide and the second polypeptide, the POROS XS™ Strong Cation Exchange Resin was washed with 20 mM sodium phosphate (pH 6.5) solution, and then elution was performed by concentration gradient using 20 mM sodium phosphate (pH 6.5) solution with 1 M sodium chloride, to obtain a final substance. Fractions meeting a criterion for purity of 95% or higher were pooled using size exclusion chromatography analysis.

Example 10.2: Evaluation of Activity of Optimized Long-Acting GDF15 Fusion Proteins (Dimers)

The two variants (FM9+Fc_hole and FM11+Fc_hole) showing excellent activity and purity improvement after purification were compared and evaluated in terms of activity depending on linker type and length. Activity of the respective long-acting GDF15 fusion proteins was evaluated in the same manner as in Example 2, and the results are shown in Table 10. Here, the long-acting GDF15 fusion proteins were compared, in terms of activity depending on GDF15 sequence, and linker type and length, based on in vitro GDF15 activity ($E_{max}$ of 100%) of the FM9-6+ Fc_hole.

TABLE 10

| Designation of substance (SEQ ID NO) | Changes in sequence of GDF15 | Fusion carrier | Linker sequence | $E_{max}$ (%) | $EC_{50}$ (nM) |
|---|---|---|---|---|---|
| FM9-1 + Fc_hole (SEQ ID NOs: 98 and 47) | ΔN2, S64R (SEQ ID NO: 28) | IgG1 Fc_knob (SEQ ID NO: 46) IgG1 Fc_hole (SEQ ID NO: 47) | $GS(G4S)_3$ (SEQ ID NO: 92) | 97.6 | 9.0 |
| FM9-2 + Fc_hole (SEQ ID NOs: 99 and 47) | ΔN2, S64R (SEQ ID NO: 28) | IgG1 Fc_knob (SEQ ID NO: 46) IgG1 Fc_hole (SEQ ID NO: 47) | $GS(G4S)_5$ (SEQ ID NO: 93) | 110.8 | 9.5 |
| FM9-3 + Fc_hole (SEQ ID NOs: 100 and 47) | ΔN2, S64R (SEQ ID NO: 28) | IgG1 Fc_knob (SEQ ID NO: 46) IgG1 Fc_hole (SEQ ID NO: 47) | $GS(G4S)_7$ (SEQ ID NO: 94) | 95.6 | 9.3 |
| FM9-4 + Fc_hole (SEQ ID NOs: 101 and 47) | ΔN2, S64R (SEQ ID NO: 28) | IgG1 Fc_knob (SEQ ID NO: 46) IgG1 Fc_hole (SEQ ID NO: 47) | $GS(EEEA)_6$ (SEQ ID NO: 95) | 127.6 | 23.6 |
| FM9-5 + Fc_hole (SEQ ID NOs: 102 and 47) | ΔN2, S64R (SEQ ID NO: 28) | IgG1 Fc_knob (SEQ ID NO: 46) IgG1 Fc_hole (SEQ ID NO: 47) | $GSGGSS(PT)_{10}$ (SEQ ID NO: 96) | 100.0 | 5.3 |
| FM9-6 + Fc_hole (SEQ ID NOs: 103 and 47) | ΔN2, S64R (SEQ ID NO: 28) | IgG1 Fc_knob (SEQ ID NO: 46) IgG1 Fc_hole (SEQ ID NO: 47) | $GS(EAAAK)_6$ (SEQ ID NO: 97) | 100.0 | 6.3 |
| FM11-1 + Fc_hole (SEQ ID NOs: 104 and 47) | ΔN3, G4N, D5S, H6T, S64R (SEQ ID NO: 30) | IgG1 Fc_knob (SEQ ID NO: 46) IgG1 Fc_hole (SEQ ID NO: 47) | $GS(G4S)_3$ (SEQ ID NO: 92) | 65.6 | 9.7 |
| FM11-2 + Fc_hole (SEQ ID NOs: 105 and 47) | ΔN3, G4N, D5S, H6T, S64R (SEQ ID NO: 30) | IgG1 Fc_knob (SEQ ID NO: 46) IgG1 Fc_hole (SEQ ID NO: 47) | $GS(G4S)_5$ (SEQ ID NO: 93) | 79.4 | 7.7 |
| FM11-3 + Fc_hole (SEQ ID NOs: 106 | ΔN3, G4N, D5S, H6T, S64R | IgG1 Fc_knob (SEQ ID NO: 46) | $GS(G4S)_7$ (SEQ ID NO: 94) | 81.0 | 7.8 |

TABLE 10-continued

| Designation of substance (SEQ ID NO) | Changes in sequence of GDF15 | Fusion carrier | Linker sequence | $E_{max}$ (%) | $EC_{50}$ (nM) |
|---|---|---|---|---|---|
| and 47) | (SEQ ID NO: 30) | IgG1 Fc_hole (SEQ ID NO: 47) | | | |
| FM11-4 + Fc_hole (SEQ ID NOs: 107 and 47) | ΔN3, G4N, D5S, H6T, S64R (SEQ ID NO: 30) | IgG1 Fc_knob (SEQ ID NO: 46) IgG1 Fc_hole (SEQ ID NO: 47) | $GS(EEEA)_6$ (SEQ ID NO: 95) | 104.8 | 45.4 |
| FM11-5 + Fc_hole (SEQ ID NOs: 108 and 47) | ΔN3, G4N, D5S, H6T, S64R (SEQ ID NO: 30) | IgG1 Fc_knob (SEQ ID NO: 46) IgG1 Fc_hole (SEQ ID NO: 47) | $GSGGSS(PT)_{10}$ (SEQ ID NO: 96) | 68.2 | 5.1 |
| FM11-6 + Fc_hole (SEQ ID NOs: 109 and 47) | ΔN3, G4N, D5S, H6T, S64R (SEQ ID NO: 30) | IgG1 Fc_knob (SEQ ID NO: 46) IgG1 Fc_hole (SEQ ID NO: 47) | $GS(EAAAK)_5$ (SEQ ID NO: 97) | 80.3 | 6.8 |

As a result, as shown in Table 10, it was identified that the respective long-acting GDF15 fusion proteins exhibited similar activity except those in which the linker $GS(EEEA)_6$ (SEQ ID NO: 95) was used, and the long-acting GDF15 fusion proteins (FM9-4+Fc_hole and FM11-4+Fc_hole), in which linker $GS(EEEA)_6$ (SEQ ID NO: 95) was used, exhibited relatively low $EC_{50}$ value and high $E_{max}$ value (FIGS. 9 and 10).

Example 10.3: Pharmacokinetic Evaluation of Optimized Long-Acting GDF15 Fusion Proteins (Dimers)

On the day of drug treatment, six-week-old male C57BL/6 mice purchased from Orient BIO (Korea) were divided into groups (n=3 per blood collection time point) so that each group had a similar average value of body weight, and then the FM9-4+Fc_hole, the FM9-6+Fc_hole, the FM11-4+Fc_hole, and the FM11-6+Fc_hole were respectively administered subcutaneously once at a dose of 1 mg/kg. Blood samples were respectively collected 4, 24, 48, 72, 96, 120, 168, and 240 hours after the administration. A concentration of each long-acting GDF15 fusion protein (dimer) in mouse blood was measured using an immunoassay method. Based on the measured concentration values, pharmacokinetic parameter results were calculated for the respective long-acting GDF15 fusion proteins (dimers) and are shown in Table 11 below.

TABLE 11

| Designation of substance (SEQ ID NO) | $C_{max}$ (ng/mL) | $T_{max}$ (hr) | CL/F (mL/hr/kg) | Vd/F (mL/kg) | $AUC_{last}$ (ng · hr/mL) | $T_{1/2,\ app}$ (hr) |
|---|---|---|---|---|---|---|
| FM9-4 + Fc_hole (SEQ ID NOs: 101 and 47) | 8421.37 | 24 | 1.30 | 69.31 | 750497.02 | 36.84 |
| FM9-6 + Fc_hole (SEQ ID NOs: 103 and 47) | 7581.92 | 24 | 0.91 | 111.02 | 939308.72 | 84.28 |
| FM11-4 + Fc_hole (SEQ ID NOs: 107 and 47) | 7200.02 | 24 | 1.41 | 82.63 | 690213.08 | 40.61 |
| FM11-6 + Fc_hole (SEQ ID NOs: 109 and 47) | 1547.77 | 24 | 8.43 | 314.10 | 116433.94 | 25.84 |

Example 10.4: Evaluation of Anti-Obesity Effect of Optimized Long-Acting GDF15 Fusion Proteins (Dimers), Depending on Different Linker Types, in Diet-Induced Obese (DIO) Mice by Repeated Administration Diet-induced obese (DIO) mice which have been induced by feeding a high-fat diet in mice, and are characterized by obesity, hyperglycemia, and insulin resistance. The DIO mice (Taconic, USA) which had been fed a high fat diet (60 kcal % fat, Research Diets, Cat #D12492, USA) in C57BL/6N mice for 8 weeks were purchased from Raon Bio (Animal Inc., Republic of Korea). After the arrival, these animals were additionally fed by the high-fat diet (60% fat) for 5 weeks, and then used in this study. On the day before the dosing start, the animals were divided into groups (n=6 per group) based on mean body weight of individual mice, and then FM9-4+Fc_hole, FM9-6+Fc_hole, FM11-4+Fc_hole, and FM11-6+Fc_hole were administered subcutaneously at 2-day interval (Q2D) for a total of 4 weeks at a dose of 10 nmol/kg, respectively. As reference articles, B13a/B13b (U.S. Pat. No. 9,920,118) at 10 nmol/kg and semaglutide at 30 nmol/kg were administered subcutaneously at 2-day interval (Q2D) for a total of 4 weeks. For vehicle treatment, Dulbecco's phosphate buffered saline (DPBS; Gibco, USA) was administered subcutaneously at 2-day interval (Q2D). Body weight was measured every two days from the first day of drug treatment to Day 28, and the results were shown in Table 12 below.

TABLE 12

| Group | Dose (nmol/kg) | Change of body weight (%) vs. Day 0 Maximal efficacy | Efficacy on Day 27 |
|---|---|---|---|
| Vehicle | — | — | 4.44 |
| FM9-4 + Fc_hole (SEQ ID NOs: 101 and 47) | 10 | −20.67 (on Day 27) | −20.67 |
| FM9-6 + Fc_hole (SEQ ID NOs: 103 and 47) | 10 | −19.93 (on Day 27) | −19.93 |
| FM11-4 + Fc_hole (SEQ ID NOs: 107 and 47) | 10 | −22.11 (on Day 27) | −22.11 |
| FM11-6 + Fc_hole (SEQ ID NOs: 109 and 47) | 10 | −11.63 (on Day 22) | −9.93 |
| B13a/B13b | 10 | −6.18 (on Day 8) | 0.60 |
| Semaglutide | 30 | −19.20 (on Day 22) | −16.41 |

As a result, it was confirmed that all test articles with different linker types (FM9-4+Fc_hole, FM9-6+Fc_hole, FM11-4+Fc_hole, and FM11-6+Fc_hole) demonstrated a marked body weight loss effect, compared to B13a/B13b of 10 nmol/kg, as a reference drug. In addition, three test articles, FM9-4+Fc_hole, FM9-6+Fc_hole, and FM11-4+Fc_hole, showed a body weight reduction effect similar to semaglutide, 30 nmol/kg-treated group (FIG. 11).

Example 10.5: Evaluation of Anti-Obesity Effect of Optimized Long-Acting GDF15 Fusion Proteins (Dimers) in Diet-Induced Obese Mice by Single Administration Male C57BL/6N mice at 6-week-old were purchased from Orient Bio (via Hallym Lab. Animal Inc., Republic of Korea). After the arrival, C57BL/6N mice were induced DIO by feeding with a high-fat diet (60 kcal % fat, Research Diets, Cat #D12492, USA) for a total of 13 weeks. On the day before the dosing start, the animals were divided into groups (n=6 per group) based on mean body weight of individual mice, and then FM9-6+Fc_hole of 1, 3, 10, and 30 nmol/kg was administered subcutaneously once. As a reference article, semaglutide of 30 nmol/kg was administered subcutaneously once. For vehicle treatment, Dulbecco's phosphate buffered saline (DPBS; Gibco, USA) was administered subcutaneously. A body weight was measured daily from the day of drug treatment to Day 42, and the results are shown in Table 13 below.

TABLE 13

| Group | Dose (nmol/kg) | Change of body weight (%) vs. Day 0 Maximal efficacy | Efficacy on Day 38 |
|---|---|---|---|
| Vehicle | — | — | 10.02 |
| FM9-6 + Fc_hole | 1 | −6.54 (on Day 10) | 3.10 |
| FM9-6 + Fc_hole | 3 | −9.74 (on Day 15) | 3.23 |
| FM9-6 + Fc_hole | 10 | −13.08 (on Day 18) | 0.63 |
| FM9-6 + Fc_hole | 30 | −14.39 (on Day 18) | −5.51 |
| Semaglutide | 30 | −8.38 (on Day 2) | 7.33 |

As a result, in terms of body weight loss effect by single administration, the semaglutide, 30 nmol/kg treated group, as a reference article, demonstrated a pharmacologic effect lasting for 2 days, whereas the single administration of FM9-6+Fc_hole of 1, 3, 10, and 30 nmol/kg was confirmed that anti-obesity effect lasted for 10 days, 15 days, 18 days, and 18 days, respectively for each doses (FIG. 12).

Example 10.6: Evaluation of Anti-Obesity Effect of Optimized Long-Acting GDF15 Fusion Proteins (Dimers) in Ob/Ob Mice by Repeated Administration ob/ob mice are genetically deficient in leptin gene and are characterized by hyperglycemia, insulin resistance, hyperorexia, and obesity. Male ob/ob mice at 5-week-old (Jackson Laboratory, USA) were purchased from Raon Bio (Animal Inc., Republic of Korea). The mice were acclimatized for 4 weeks with normal chow diet (Teklad Certified Irradiated Global 18% Protein Rodent Diet, 2918C, Harlan Co., USA) and drug treatment was initiated at 9-week-old. On the day before the dosing start, the animals were divided into groups (n=6 per group) based on mean body weight and random blood glucose via tail vein of individual mice. Then, the FM9-6+Fc_hole of 0.1, 1, and 3 nmol/kg, and semaglutide of 10 nmol/kg were administered subcutaneously at 3-day interval (Q3D) a total of 10 times, and body weight and food intake were measured every day or every 3 days during experimental period (Day 1-Day 29), respectively. For vehicle treatment, Dulbecco's phosphate buffered saline (DPBS; Gibco, USA) was administered.

TABLE 14

| Group | Dose (nmol/kg) | Change of body weight (%) vs. ob/ob control Maximal efficacy | Efficacy on Day 29 |
|---|---|---|---|
| Vehicle | — | — | — |
| FM9-6 + Fc_hole | 0.1 | −10.58 (on Day 28) | −9.98 |
| FM9-6 + Fc_hole | 1 | −21.49 (on Day 29) | −21.49 |
| FM9-6 + Fc_hole | 3 | −19.99 (on Day 29) | −19.99 |
| Semaglutide | 10 | −10.04 (on Day 25) | −6.88 |

As a result, it was confirmed that FM9-6+Fc_hole manifested body weight loss effect in a dose-dependent manner. FM9-6+Fc_hole, 0.1 nmol/kg treated group showed significant reduction in body weight similar to semaglutide, 10 nmol/kg treated group. FM9-6+Fc_hole of 1 nmol/kg or more demonstrated the maximal efficacy in ob/ob mice (FIG. 13).

The invention claimed is:

1. A growth differentiation factor-15 (GDF15) variant represented by Formula (I):

N-terminal extension domain-core domain (I)

in Formula (I),

- is a bond;

the N-terminal extension domain is a polypeptide consisting of any one amino acid sequence of SEQ ID NOs: 3 to 5; and the core domain is a polypeptide of SEQ ID NO: 20, or a polypeptide of SEQ ID NO: 20 with a modification(s), wherein the modification(s) consists of any one of the following (1) to (6):

(1) substitution of arginine (R) at position 15 with asparagine (N) with respect to SEQ ID NO: 20;

(2) substitution of asparagine (N) at position 50 to with leucine (L) with respect to SEQ ID NO: 20;

(3) substitution of serine(S) at position 58 with one of lysine (K), arginine (R), asparagine (N), aspartic acid (D), glutamic acid (E), cysteine (C), or leucine (L) with respect to SEQ ID NO: 20;

(4) substitution of aspartic acid (D) at position 97 with leucine (L) with respect to SEQ ID NO: 20;

(5) substitution of asparagine (N) at position 50 to with cysteine (C) or serine(S) and substitution of aspartic acid (D) at position 97 with cysteine (C) or serine(S), with respect to SEQ ID NO: 20; or (6) substitution of arginine (R) at position 15 with asparagine (N) and substitution of serine(S) at position 58 with lysine (K) or arginine (R), with respect to SEQ ID NO: 20.

2. The GDF15 variant of claim 1, wherein the core domain consists of any one amino acid sequence selected from SEQ ID NOs: 6 to 19.

3. The GDF15 variant of claim 1, wherein the GDF15 variant includes the N-terminal extension domain consisting of the amino acid sequence of SEQ ID NO: 3 and the core domain consisting of the amino acid sequence of SEQ ID NO: 8, 9, or 20.

4. The GDF15 variant of claim 1, wherein the GDF15 variant includes the N-terminal extension domain consisting of the amino acid sequence of SEQ ID NO: 4 and the core domain consisting of the amino acid sequence of SEQ ID NO: 8, 9, or 20.

5. The GDF15 variant of claim 1, wherein the GDF15 variant includes the N-terminal extension domain consisting of the amino acid sequence of SEQ ID NO: 5 and the core domain consisting of any one amino acid sequence selected from the group consisting of SEQ ID NO: 6 to 19.

6. The GDF15 variant of claim 1, wherein the GDF15 variant consists of any one amino acid sequence selected from the group consisting of SEQ ID NOs: 21 to 39.

7. A long-acting growth differentiation factor-15 (GDF15) fusion protein, in which the GDF15 variant of claim 1 is bound to human IgG Fc or a variant thereof, wherein the human IgG Fc or the variant thereof comprises:

a first polypeptide comprising any one amino acid sequence selected from the group consisting of SEQ ID NOs: 42, 44, and 46; and a second polypeptide comprising any one amino acid sequence selected from the group consisting of SEQ ID NOs: 43, 45, and 47, and wherein the C-terminus of the first polypeptide of the IgG Fc or the variant thereof or the C-terminus of the second polypeptide of the IgG Fc or a variant thereof, is bound to the N-terminus of the GDF15 variant.

8. The long-acting GDF15 fusion protein of claim 7, wherein the GDF15 variant is bound to the IgG Fc or the variant thereof via a linker.

9. The long-acting GDF15 fusion protein of claim 8, wherein the linker is (G4S)n, GS(G4S)n, GS(EEEA)n, (EEEA)n, GS(EAAAK)n, (EAAAK)n, or GSGGSS(PT)n, where n is an integer of 1 to 10.

10. The long-acting GDF15 fusion protein of claim 9, wherein the linker is

```
                                    (SEQ ID NO: 48)
GGGGSGGGGSGGGGSGGGGSGGGGS,

                                    (SEQ ID NO: 92)
GSGGGGSGGGGSGGGGS,

                                    (SEQ ID NO: 93)
GSGGGGSGGGGSGGGGSGGGGSGGGGS,

                                    (SEQ ID NO: 94)
GSGGGGSGGGGSGGGGSGGGGSGGGGSGGGGSGGGGS,

                                    (SEQ ID NO: 95)
GSEEEAEEEAEEEAEEEAEEEAEEEA,

                                    (SEQ ID NO: 96)
GSGGSSPTPTPTPTPTPTPTPTPT,
or

                                    (SEQ ID NO: 97)
GSEAAAKEAAAKEAAAKEAAAKEAAAK.
```

11. The long-acting GDF15 fusion protein of claim 7, wherein the GDF15 variant comprises at least one N-linked glycan.

12. The long-acting GDF15 fusion protein of claim 7, wherein the GDF15 variant comprises any one amino acid sequence selected from the group consisting of SEQ ID NOs: 21 to 39.

13. A fusion protein dimer, comprising:

two of the long-acting GDF15 fusion protein of claim 7.

14. An isolated nucleic acid molecule, encoding the GDF15 variant of claim 1, or a long-acting GDF15 fusion protein in which the GDF15 variant of claim 1 is bound to human IgG Fc or a variant thereof, wherein the human IgG Fc or the variant thereof comprises:

a first polypeptide comprising any one amino acid sequence selected from the group consisting of SEQ ID NOs: 42, 44, and 46; and a second polypeptide comprising any one amino acid sequence selected from the group consisting of SEQ ID NOs: 43, 45, and 47, and wherein the C-terminus of the first polypeptide of the IgG Fc or the variant thereof or the C-terminus of the second polypeptide of the IgG Fc or a variant thereof, is bound to the N-terminus of the GDF15 variant.

15. An expression vector, comprising:

the nucleic acid molecule of claim 14.

16. A host cell, comprising:

the expression vector of claim 15.

17. A pharmaceutical composition comprising as an active ingredient:

(a) the GDF15 variant of claim 1, (b) a long-acting GDF15 fusion protein in which the GDF15 variant of claim 1 is bound to human IgG Fc or a variant thereof, wherein the human IgG Fc or the variant thereof comprises:

a first polypeptide comprising any one amino acid sequence selected from the group consisting of SEQ ID NOs: 42, 44, and 46; and a second polypeptide comprising any one amino acid sequence selected from the group consisting of SEQ ID NOs: 43, 45, and 47, and wherein the C-terminus of the first polypeptide of the IgG Fc or the variant thereof or the C-terminus of the second polypeptide of the IgG Fc or a variant thereof, is bound to the N-terminus of the GDF15 variant, or (c) a fusion protein dimer comprising two of the long-acting GDF15 fusion protein of (b).

18. A method for treating diabetes, obesity, dyslipidemia, or metabolic syndrome in an individual in need thereof, comprising:

a step of administering, to the individual, an effective amount of (a) the GDF15 variant of claim 1, (b) a long-acting GDF15 fusion protein in which the GDF15 variant of claim 1 is bound to human IgG Fc or a variant thereof, wherein the human IgG Fc or the variant thereof comprises:

a first polypeptide comprising any one amino acid sequence selected from the group consisting of SEQ ID NOs: 42, 44, and 46; and a second polypeptide comprising any one amino acid sequence selected from the group consisting of SEQ ID NOs: 43, 45, and 47, and wherein the C-terminus of the first polypeptide of the IgG Fc or the variant thereof or the C-terminus of the second polypeptide of the IgG Fc or a variant thereof, is bound to the N-terminus of the GDF15 variant, or (c) a fusion protein dimer comprising two of the long-acting GDF15 fusion protein of (b).

19. The long-acting GDF15 fusion protein of claim 12, wherein the GDF15 variant is bound to the IgG Fc or the variant thereof via a linker, said linker being

```
                                    (SEQ ID NO: 48)
GGGGSGGGGSGGGGSGGGGSGGGGS,

                                    (SEQ ID NO: 92)
GSGGGGSGGGGSGGGGS,

                                    (SEQ ID NO: 93)
GSGGGGSGGGGSGGGGSGGGGSGGGGS,

                                    (SEQ ID NO: 94)
GSGGGGSGGGGSGGGGSGGGGSGGGGSGGGGSGGGGS,

                                    (SEQ ID NO: 95)
GSEEEAEEEAEEEAEEEAEEEAEEEA,

                                    (SEQ ID NO: 96)
GSGGSSPTPTPTPTPTPTPTPTPT,
or

                                    (SEQ ID NO: 97)
GSEAAAKEAAAKEAAAKEAAAKEAAAK.
```

20. The long-acting GDF15 fusion protein of claim 19, wherein the GDF variant comprises the amino acid sequence of SEQ ID NO: 28 or 30;

the first polypeptide of the IgG Fc of the variant thereof comprises the sequence of SEQ ID NO: 46;

the second polypeptide of the IgG Fc of the variant thereof comprises the sequence of SEQ ID NO: 47; and the linker consists of the sequence of SEQ ID NO: 95 or 97.

21. The long-acting GDF15 fusion protein of claim 19, wherein the long-acting GDF15 fusion protein comprises the amino acid sequence of SEQ ID NO: 98, 99, 100, 101, 102, 103, 104, 105, 106, 107, 108, or 109.

22. A complex comprising the growth differentiation factor-15 (GDF15) variant of claim 1 and an IgG Fc, said complex being represented by the following formula (II):

$$\text{IgG Fc-(L)}_m\text{-N-terminal extension domain-core domain} \quad \text{(II)}$$

wherein m is an integer of 0 or 1,

L is a linker selected from the group consisting of SEQ ID NOs: 48, 92, 93, 94, 95, 96, and 97, IgG Fc comprises the amino acid sequence of SEQ ID NOs: 42, 44, or 46, and N-terminal extension domain and core domain are as defined in claim 1.

23. The complex of claim 22, wherein the N-terminal extension domain-core domain comprises any one amino acid sequence selected from the group consisting of SEQ ID NOs: 21 to 39.

24. The complex of claim 22, wherein the complex comprises any one amino acid sequence selected from the group consisting of SEQ ID NOs: 50-91 and 98-109.

* * * * *